(12) United States Patent
Schinazi et al.

(10) Patent No.: US 11,859,014 B2
(45) Date of Patent: Jan. 2, 2024

(54) PEPTIDOMIMETICS FOR THE TREATMENT OF NOROVIRUS INFECTION

(71) Applicant: EMORY UNIVERSITY, Atlanta, GA (US)

(72) Inventors: Raymond F Schinazi, Miami, FL (US); Franck Amblard, Atlanta, GA (US); Ladislau Kovari, Detroit, MI (US); Peng Liu, Atlanta, GA (US); Shaoman Zhou, Atlanta, GA (US); Benjamin D Kuiper, Detroit, MI (US); BRadley J Keusch, Detroit, MI (US)

(73) Assignee: EMORY UNIVERSITY, Atlanta, GA (US)

( * ) Notice: Subject to any disclaimer, the term of this patent is extended or adjusted under 35 U.S.C. 154(b) by 20 days.

(21) Appl. No.: 17/329,670

(22) Filed: May 25, 2021

(65) Prior Publication Data
US 2021/0395300 A1 Dec. 23, 2021

Related U.S. Application Data

(63) Continuation of application No. 16/301,168, filed as application No. PCT/US2017/032600 on May 15, 2017, now Pat. No. 11,021,513.

(60) Provisional application No. 62/335,962, filed on May 13, 2016.

(51) Int. Cl.
| | |
|---|---|
| C07K 5/06 | (2006.01) |
| C07K 5/065 | (2006.01) |
| A61P 31/14 | (2006.01) |
| A61K 38/05 | (2006.01) |
| A61K 45/06 | (2006.01) |

(52) U.S. Cl.
CPC .......... *C07K 5/06078* (2013.01); *A61K 38/05* (2013.01); *A61K 45/06* (2013.01); *A61P 31/14* (2018.01)

(58) Field of Classification Search
CPC ............ C07K 5/06078; C07K 5/06191; C07K 5/06017; A61P 31/14; A61P 31/12; A61K 38/05; A61K 45/06; A61K 31/4025; A61K 31/45; A61K 31/497; A61K 31/5377; A61K 31/4015
See application file for complete search history.

(56) References Cited

U.S. PATENT DOCUMENTS

2005/0143319 A1* 6/2005 Yang .................... C07D 207/26
514/79

FOREIGN PATENT DOCUMENTS

WO WO-2013049382 A2 * 4/2013 ......... A61K 31/4015

OTHER PUBLICATIONS

Prior et al.(Bioorganic & Medicinal Chemistry Letters, 2013, 23(23), 6317-6320) (Year: 2013).*

* cited by examiner

*Primary Examiner* — Sudhakar Katakam
(74) *Attorney, Agent, or Firm* — David S. Bradin; Maynard Nexsen PC

(57) ABSTRACT

The present invention is directed to compounds, compositions and methods for preventing, treating or curing Norovirus infection in human subjects or other animal hosts.

16 Claims, No Drawings
Specification includes a Sequence Listing.

PEPTIDOMIMETICS FOR THE TREATMENT OF NOROVIRUS INFECTION

CROSS REFERENCE TO RELATED APPLICATIONS

The present application is a continuation of U.S. Ser. No. 16/301,168, filed on Nov. 13, 2018, which claims priority under 35 U.S.C. 371 to PCT Application No. PCT/US2017/032600, filed May 15, 2017, which in turn claims priority to U.S. Provisional Application No. 62/335,962, filed May 13, 2016. The disclosures of each of these documents is hereby incorporated by reference in its entirety.

FIELD OF THE INVENTION

The present invention is directed to compounds, methods and compositions for preventing, treating and/or curing Norovirus (NoV) infections. More specifically, the invention describes specifically modified peptidomimetics, pharmaceutically acceptable salts, or other derivatives thereof, and the use thereof in the treatment of NoV infections.

BACKGROUND OF THE INVENTION

NoV are the leading cause of gastroenteritis worldwide. Annually in the United States, 21 million infections and 71,000 hospitalizations are caused by human NoV infections. Worldwide, an estimated 287 million people are infected annually, with 200,000 of these cases resulting in fatalities. The risk for long-term or fatal infections is higher in developing countries, children, the elderly, and immunocompromised patients.

The clinical course of NoV illness includes exposure (person-to-person contact, contaminated food or water, contaminated surfaces, vomitus droplets), incubation period (24 to 48 hr), acute signs/symptoms (~48 hours; diarrhea, vomiting, abdominal cramps, nausea, fever, and headache), and outcome, typically self-limiting; the risk is increased in infants, young children, elderly, and immunocompromised.

Currently, neither a vaccine nor any pharmacologic treatment for NoV infection is approved for use.

Accordingly, it would be advantageous to provide new antiviral agents, compositions including these agents, and methods of treatment using these agents to treat NoV and prevent the emergence of drug-resistant NoV. The present invention provides such agents, compositions and methods.

SUMMARY OF THE INVENTION

The present invention provides compounds, methods and compositions for preventing, treating and/or curing NoV infection in a host, or reducing the activity of NoV in the host. The methods involve administering a therapeutically or prophylactically-effective amount of at least one compound as described herein to treat, cure or prevent an infection by, or an amount sufficient to reduce the biological activity of, a NoV infection.

The pharmaceutical compositions include one or more of the compounds described herein, in combination with a pharmaceutically acceptable carrier or excipient, for treating a host infected with NoV. These compounds can be used in combination with nucleoside and non-nucleoside inhibitors of NoV. The formulations can further include at least one other therapeutic agent. In addition, the present invention includes processes for preparing such compounds.

In another embodiment, the compounds described herein are used for treating infections caused by Sapporo virus (human), Gastroenteritis, Jena virus (cattle), Murine norovirus (mouse), Fulminant organ dysfunction, Pistoia virus (lion), Hemorrhagic enteritis, Canine norovirus (dog), Swine43 (pig), Porcine enteric calicivirus (pig), Mink enteric calicivirus (mink), Rabbit hemorrhagic disease virus (rabbit), European brown hare syndrome virus (hare), Bovine enteric calicivirus/Newbury-1 virus (cattle), Bovine enteric calicivirus/Nebraska virus (cattle), Feline calicivirus (cat), Feline calicivirus-VS (cat), San Miguel sea lion virus (sea lion), Canine calicivirus No. 48 (dog), Tulane virus (monkey), St. Valerian virus/AB90 (pig), and Bayern virus (chicken).

In one embodiment, the compounds have the following formula:

(I)

or a pharmaceutically acceptable salt or prodrug thereof, wherein:
$R^5$ is selected from $R^2$, $R^{2'}$, $R^{10}$, $R^{10'}$, $R^{11}$ and $R^{11'}$ are, independently, hydrogen, $CF_3$, $C_{1-6}$ alkyl, $C_{1-6}$ haloalkyl, or $C_{2-6}$ alkenyl, $R^{12}$ and $R^{12'}$ are, independently, $C_{1-6}$ alkyl, $C_{1-6}$ haloalkyl, or $C_{2-6}$ alkenyl, $R^{12}$ and $R^{12'}$ can come together to form an optionally substituted $C_{3-7}$ ring, optionally containing an N, O, or S;

$R^8$ is, independently, optionally substituted $C_{1-6}$ alkyl, $C_{1-6}$ haloalkyl, $C_{2-6}$ alkenyl, aryl, or arylalkyl;

m, n, p and r are independently 0, 1, 2, 3, 4 or 5;

q is 1, 2, 3, 4 or 5

X is independently selected from a bond, O or NH,

Y is independently Cl, F, I or Br, $R^{12}$ is hydrogen, $CF_3$, $CO_2R'$, $S(O)_2R'$, $S(O)_2N(R')_2$, $P(O)(OR')_2$, $C_{2-6}$ alkenyl, $C_{2-6}$ alkynyl, $C_{3-6}$ alkoxyalkyl, $C_{1-6}$ alkyl, arylalkoxycarbonyl, $C_{1-6}$ haloalkyl, heterocyclylalkyl, or $C_{1-6}$ hydroxyalkyl;

$R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl, or $R^6$ and $R^{6'}$, together with the carbon to which they are attached, form a carbonyl;

Each R' is, independently, H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, the R' groups, and other optionally substituted groups, can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, or phosphonate;

two R' residing on the same carbon or nitrogen atom can come together to form a $C_{3-6}$ ring optionally containing an N, O, or S;

$R^6$ and $R^{6'}$ can come together to form an optionally substituted double bond, a $C_{3-6}$ ring optionally containing an N, O, or S;

$R^7$ and $R^{7'}$ are, independently, hydrogen, $CF_3$, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

$R^7$ and $R^{7'}$ can come together to form an optionally substituted double bond or a $C_{3-6}$ ring optionally containing an N, O, or S;

$R^4$ and $R^3$ are, independently, optionally substituted $C_{1-6}$ alkyl, $C_{1-6}$ haloalkyl, $C_{2-8}$ alkoxyalkyl, arylalkyl, heteroarylalkyl, or —$CH_2$—$R^{4'}$, $R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring; and $R^1$ is optionally substituted aryl, heteroaryl, aryloxy, heteroaryloxy, arylalkoxy, or heteroarlalkoxy, wherein the term "optionally substituted" applies to each member of this group.

In another embodiment, the compounds have the following formula:

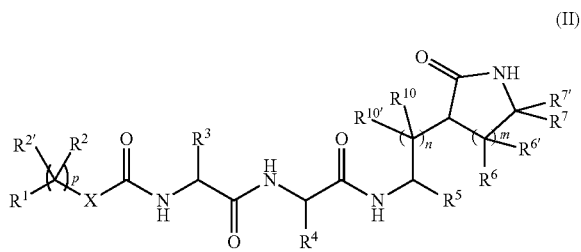

(II)

or a pharmaceutically acceptable salt or prodrug thereof, wherein:

$R^5$ is

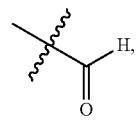

ketoamides, bisulfite salts,

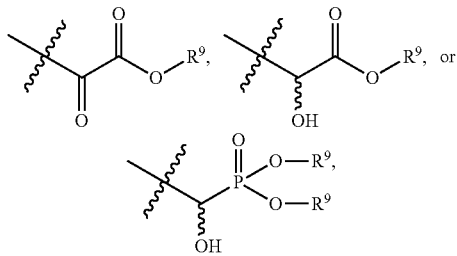

$R^9$ is, independently, optionally substituted $C_{1-6}$ alkyl, $C_{1-6}$ haloalkyl, aryl, heteroaryl, arylalkyl, or heteroarylalkyl, $R^4$ and $R^3$ are, independently, optionally substituted $C_{1-6}$ alkyl, $C_{1-6}$ haloalkyl, $C_{2-8}$ alkoxyalkyl, arylalkyl, heteroarylalkyl, or —$CH_2$—$R^{4'}$, $R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

$R^1$ is optionally substituted aryl, heteroaryl, aryloxy, heteroaryloxy, arylalkoxy, or heteroarlalkoxy, wherein the term "optionally substituted" applies to each member of this group, $R^2$, $R^{2'}$, $R^{10}$ and $R^{10'}$ are, independently, hydrogen, $CF_3$, $C_{1-6}$ alkyl, $C_{1-6}$ haloalkyl, or $C_{2-6}$ alkenyl, X is, independently, a bond, O or NH, m, n, and p are, independently, 0, 1, 2, 3, 4 or 5;

when n and m are not 1: $R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl; or $R^6$ and $R^{6'}$, together with the carbon to which they are attached, form a carbonyl, Each R' is, independently, H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, the R' groups can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, or phosphonate; two R' residing on the same carbon or nitrogen atom can come together to form a $C_{3-6}$ ring optionally containing a N, O, or S heteroatom; $R^6$ and $R^{6'}$ can come together to form an optionally substituted double bond or a $C_{3-6}$ ring optionally containing a N, O, or S heteroatom; $R^7$ and $R^{7'}$ are, independently, hydrogen, $CF_3$, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl; $R^7$ and $R^{7'}$ can come together to form an optionally substituted double bond or a $C_{3-6}$ ring optionally containing a N, O, or S heteroatom; and when n and m are 1, at least one or $R^2$, $R^6$, $R^{6'}$, $R^7$ and $R^{7'}$ is not hydrogen.

In yet another embodiment, the compounds have the following formula:

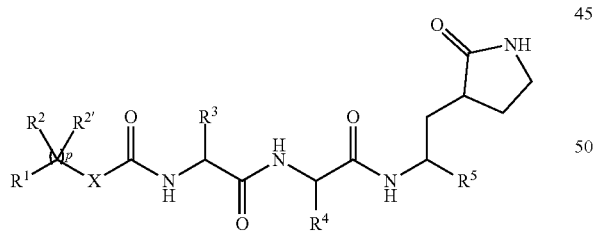

(III)

or a pharmaceutically acceptable salt or prodrug thereof, wherein:

$R^5$ is

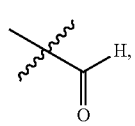

ketoamides, bisulfite salts,

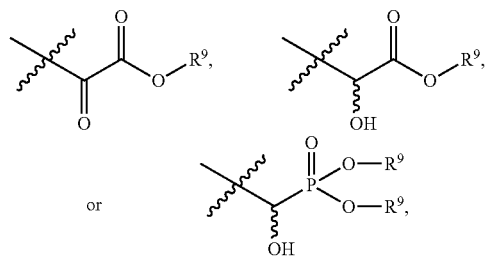

$R^9$ is, independently, optionally substituted $C_{1-6}$ alkyl, $C_{1-6}$ haloalkyl, aryl, heteroaryl, arylalkyl, or heteroarylalkyl, $R^2$ and $R^{2'}$ are, independently, hydrogen, $CF_3$, $C_{1-6}$ alkyl, $C_{1-6}$ haloalkyl, or $C_{2-6}$ alkenyl, $R^3$ is, independently, optionally substituted $C_{1-6}$ alkyl, $C_{1-6}$ haloalkyl, $C_{2-9}$ alkoxyalkyl, arylalkyl, heteroarylalkyl, or —$CH_2$—$R^{4'}$ $R^4$ is, independently, optionally substituted $C_{1-6}$ haloalkyl, $C_{2-8}$ alkoxyalkyl, heteroarylalkyl, or —$CH_2$—$R^{4'}$.

$R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

$R^1$ is optionally substituted aryl, heteroaryl, aryloxy, heteroaryloxy, arylalkoxy, or heteroarlalkoxy, p is 0, 1, 2, 3, 4 or 5; and X is a bond, O or NH.

In still another embodiment, the compounds have the following formula:

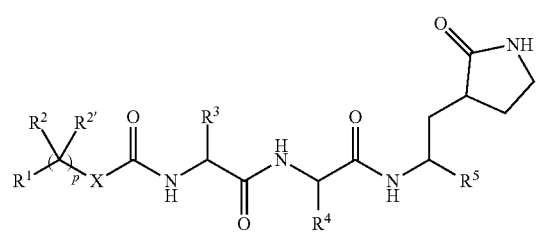

(IV)

or a pharmaceutically acceptable salt or prodrug thereof, wherein:

$R^5$ is

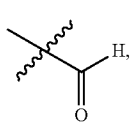

ketoamides, bisulfite salts,

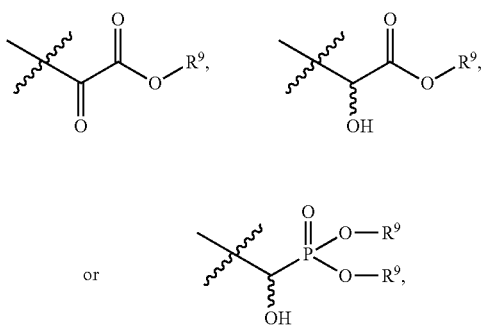

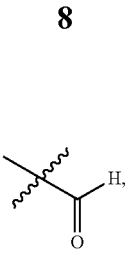

ketoamides, bisulfite salts,

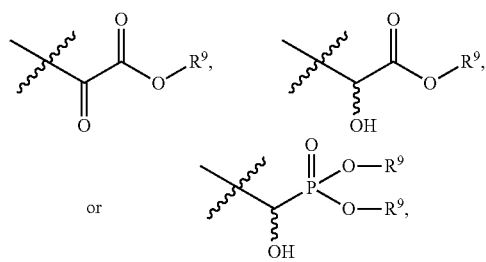

wherein a ketoamide has the formula —C(O)C(O)NHR$^x$, where R$^x$ is a branched or unbranched alkyl, cycloalkyl, or arylalkyl, and an α-hydroxyphosphonate of the formula —CH(O)(P=O)(OR$^y$)$_2$, where each R$^y$ is H, a substituted or unsubstituted alkyl, aryl, or arylalkyl, and a bisulfite has the formula —H(OH)SO$_3^-$, and the salt is any pharmaceutically acceptable salt, R$^9$ is, independently, optionally substituted C$_{1-6}$ alkyl, C$_{1-6}$ haloalkyl, aryl, heteroaryl, arylalkyl, or heteroarylalkyl, R$^4$ is optionally substituted C$_{1-6}$ alkyl, cycloalkyl, aryl, arylakyl, alkenyl, alkynyl, or a natural amino acid side chain, R$^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

R$^1$ is optionally substituted aryl, heteroaryl, aryloxy, heteroaryloxy, arylalkoxy, or heteroarlalkoxy, p is 0, 1, 2, 3, 4 or 5;

X is, independently, a bond, O or NH,

R$^3$ is, independently, optionally substituted C$_{1-6}$ haloalkyl, C$_{2-8}$ alkoxyalkyl, heteroarylalkyl, or —CH$_2$—R$^{4'}$, and R$^2$ and R$^{2'}$ are, independently, hydrogen, CF$_3$, C$_{1-6}$ alkyl, C$_{1-6}$ haloalkyl, or C$_{2-6}$ alkenyl.

In still another embodiment, the compounds have the following formula:

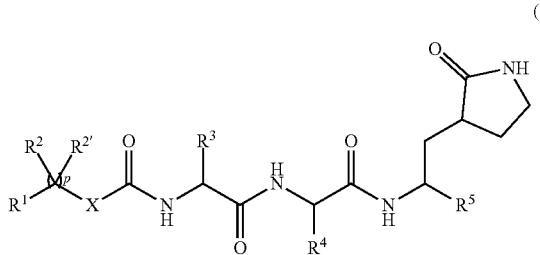

(V)

or a pharmaceutically acceptable salt or prodrug thereof, wherein:

R$^5$ is ketoamides, bisulfite salts,

R$^9$ is, independently, optionally substituted C$_{1-6}$ alkyl, C$_{1-6}$ haloalkyl, aryl, heteroaryl, arylalkyl, or heteroarylalkyl, R$^4$ is optionally substituted C$_{1-6}$ alkyl, cycloalkyl, aryl, arylakyl, alkenyl, alkynyl, or a natural amino acid side chain, R$^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

R$^1$ is optionally substituted aryl, heteroaryl, aryloxy, heteroaryloxy, arylalkoxy, or heteroarlalkoxy, p is 0, 1, 2, 3, 4 or 5;

X is, independently, a bond, O or NH,

R$^3$ is, independently, optionally substituted C$_{1-6}$ haloalkyl, C$_{2-8}$ alkoxyalkyl, heteroarylalkyl, or —CH$_2$—R, R$^2$ and R$^{2'}$ are, independently, CF$_3$, C$_{1-6}$ alkyl, C$_{1-6}$ haloalkyl, or C$_{2-6}$ alkenyl.

In still another embodiment, the compounds have the following formula:

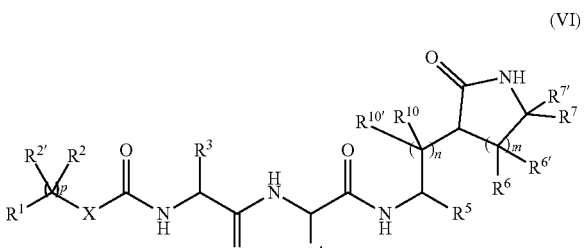

(VI)

or a pharmaceutically acceptable salt or prodrug thereof, wherein:

R$^1$ is optionally substituted aryl, heteroaryl, aryloxy, heteroaryloxy, arylalkoxy, or heteroarylalkoxy, R$^2$ and R$^{2'}$ are, independently, H, —NH$_2$, —NH-carboxybenzyl (i.e., —NHCBz), CF$_3$, C$_{1-6}$ alkyl, C$_{1-6}$ haloalkyl, or C$_2$, alkenyl, where the —NH$_2$ can optionally be protected with an amine protecting group.

R$^3$ is, independently, optionally substituted C$_{1-6}$ haloalkyl, C$_{2-6}$ alkoxyalkyl, heteroarylalkyl, or —CH$_2$—R$^{4'}$, R$^4$ is optionally substituted C$_{1-6}$ alkyl, cycloalkyl, aryl, arylakyl, alkylaryl, alkenyl, alkynyl, or a natural amino acid side chain, R$^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

R$^5$ is an acrylamide (—C(R$^2$)=C(R$^2$)—, C$_{1-6}$-haloalkyl, C$_{1-6}$ hydroxyalkyl, C$_{1-6}$-alkyl sulfonate, aryl sulfonate, heteroaryl sulfonate, C$_{1-6}$-alkyl sulfoxide, or C$_{1-6}$-ketoalkyl, wherein the alkyl moiety on any of these groups can be substituted with an epoxide (on two adjacent carbons), CN, OH, halo, keto, —CF$_3$, R$^6$ and R$^{6'}$ are, independently, hydrogen, halogen, CF$_3$, hydroxy, N(R')S(O)$_2$R', S(O)$_2$R', S(O)$_2$N(R')$_2$, C$_{1-6}$ alkoxy, C$_{2-6}$ alkenyl, cyano, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl, or R$^6$ and R$^{6'}$, together with the carbon to which they are attached, form a carbonyl;

R$^6$ and R$^{6'}$ can come together to form an optionally substituted double bond, a C$_{3-6}$ ring optionally containing an N, O, or S;

R$^7$ and R$^{7'}$ are, independently, hydrogen, CF$_3$, N(R')S(O)$_2$R', S(O)$_2$R', S(O)$_2$N(R')$_2$, C$_{1-6}$ alkoxy, C$_{2-6}$ alkenyl, cyano, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl;

R$^9$ is, independently, optionally substituted C$_{1-6}$ alkyl, C$_{1-6}$ haloalkyl, aryl, heteroaryl, arylalkyl, or heteroarylalkyl, R$^{10}$ and R$^{10'}$ are, independently, hydrogen, CF$_3$, C$_{1-6}$ alkyl, C$_{1-6}$ haloalkyl, or C$_{2-6}$ alkenyl, m, n and p are independently 0, 1, 2, 3, 4 or 5; and X is, independently, a bond, O or NH.

A subset of these compounds has the following formula:

(VIa)

Individual compounds include the following:

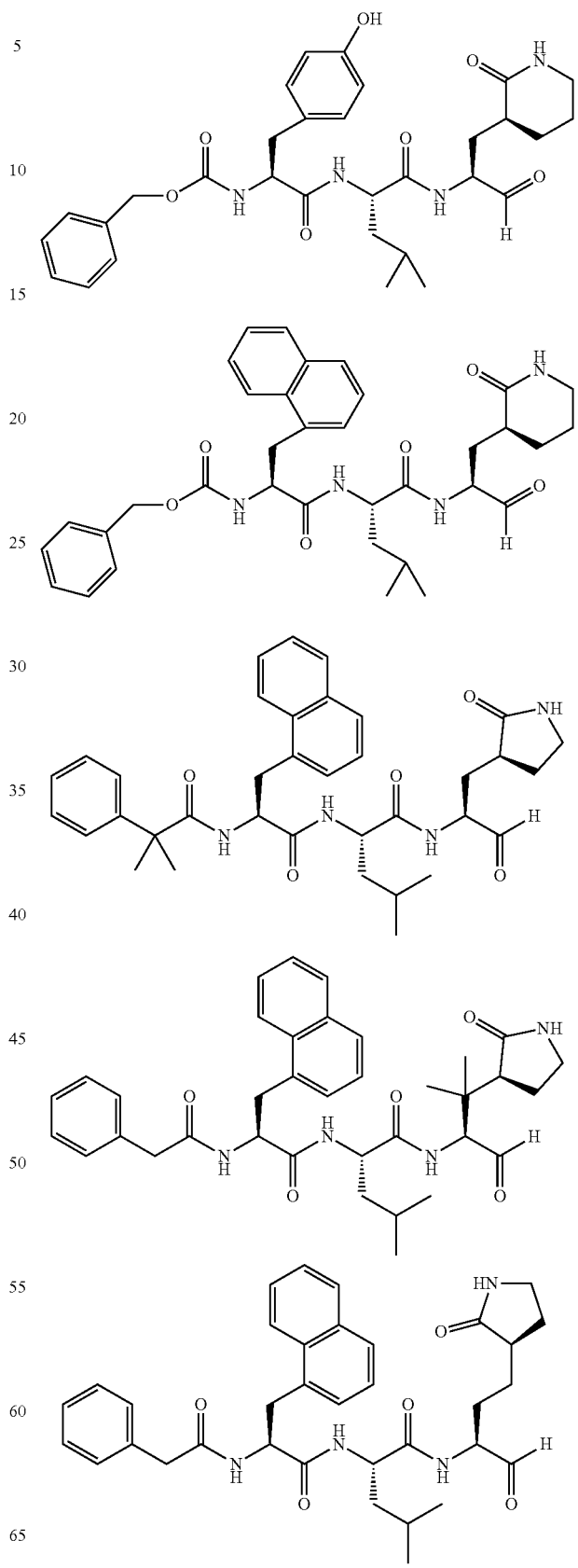

11
-continued
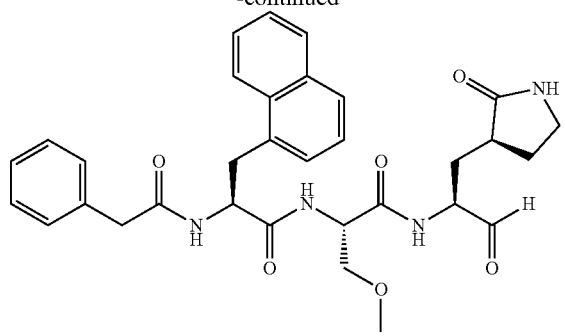
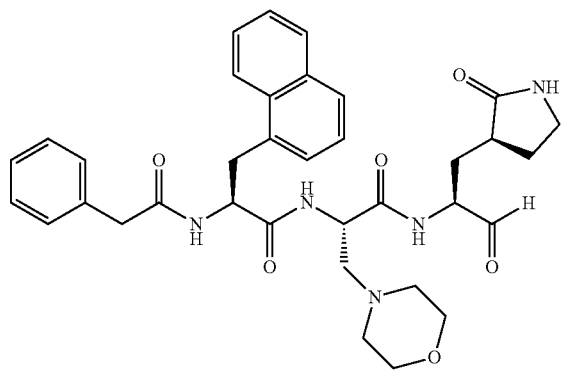
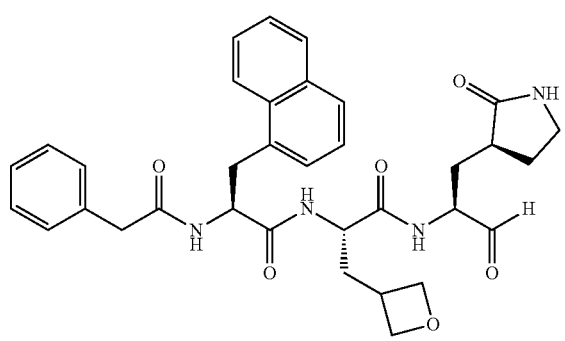
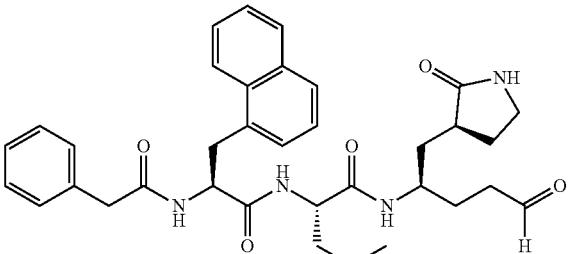
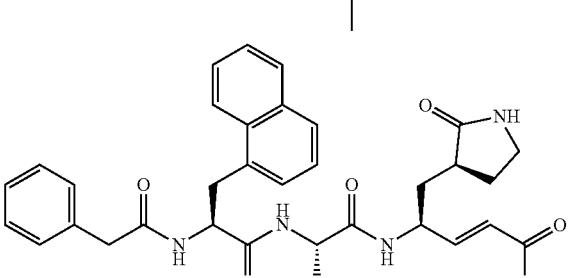
12
-continued
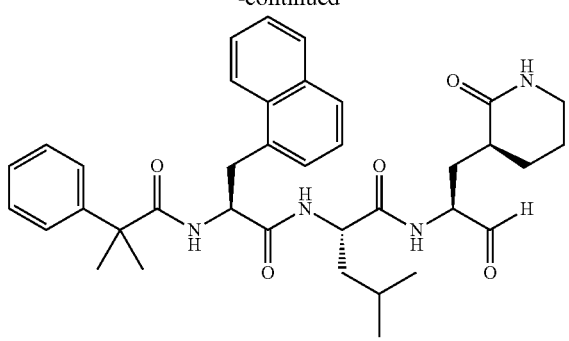
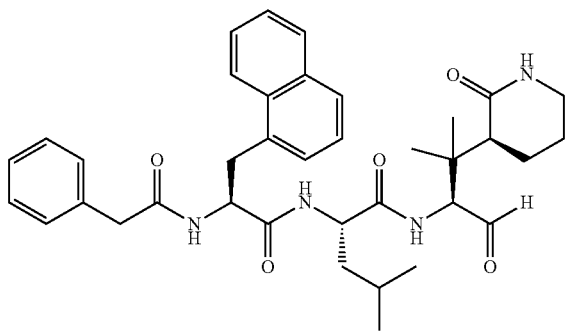
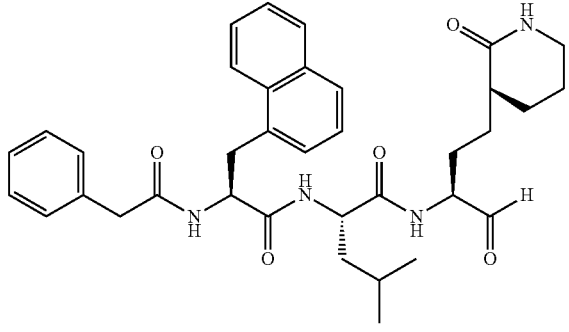
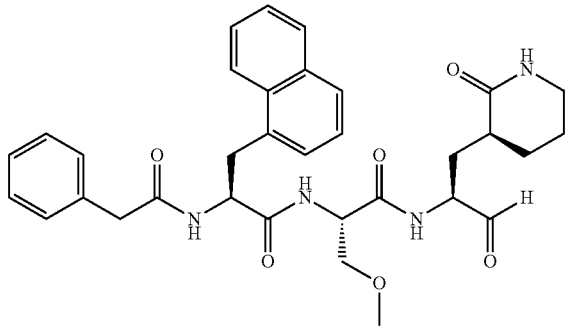
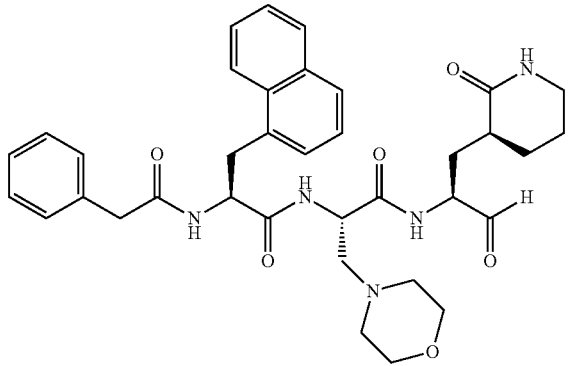

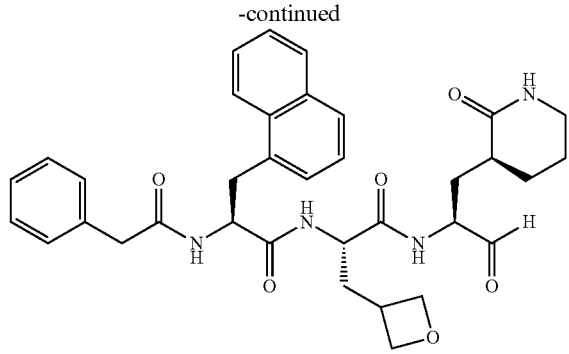
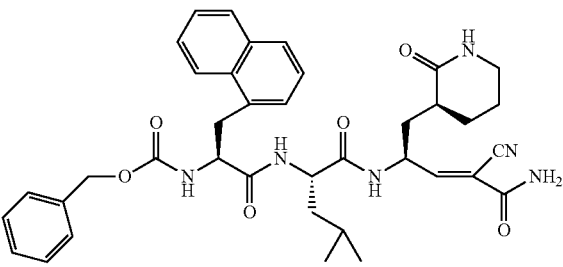
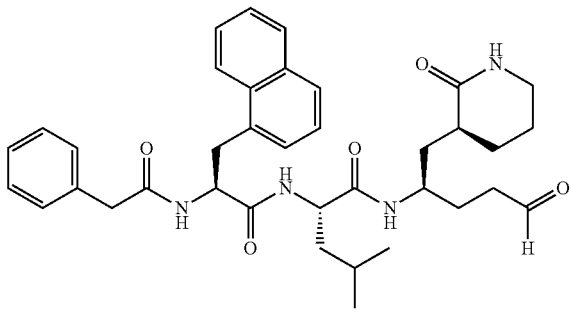
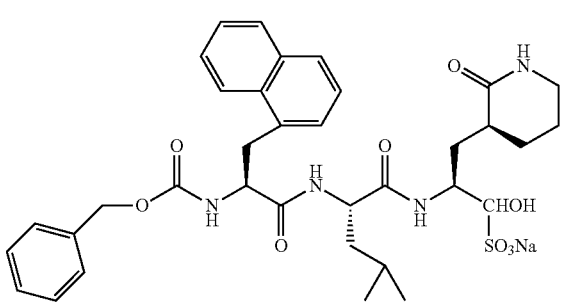
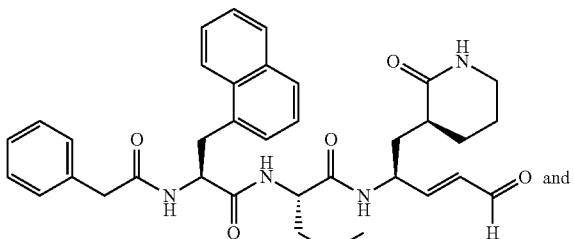
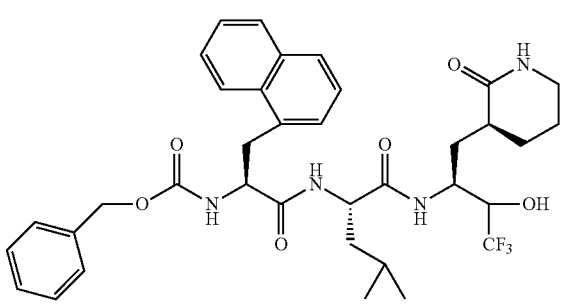
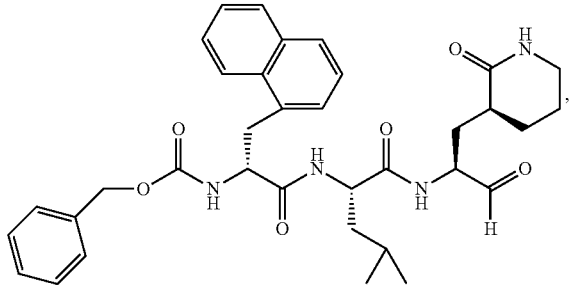
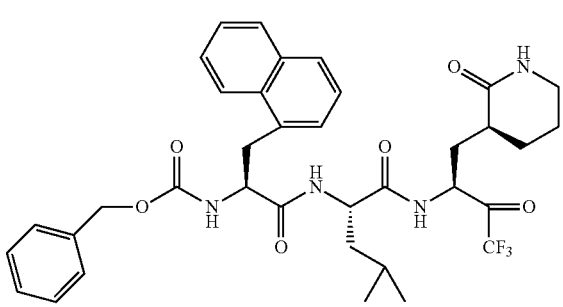
and pharmaceutically acceptable salts or prodrugs thereof. Additional compounds include the following:
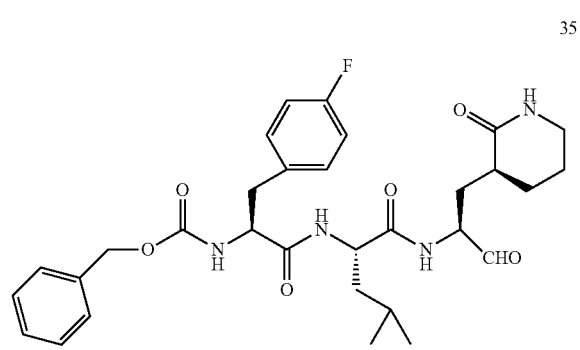
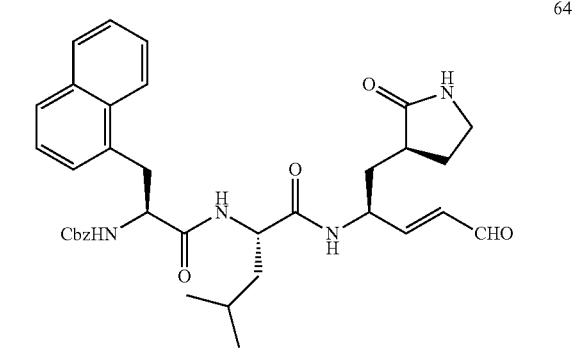

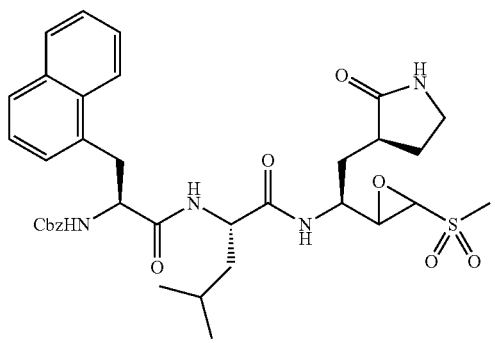

67

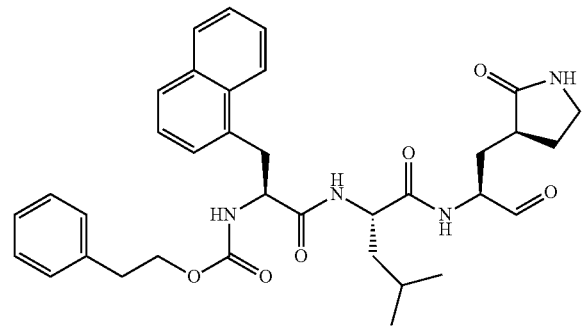

74

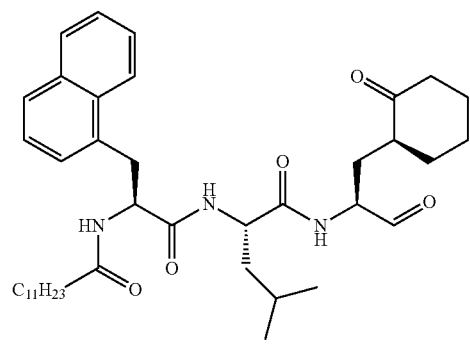

79

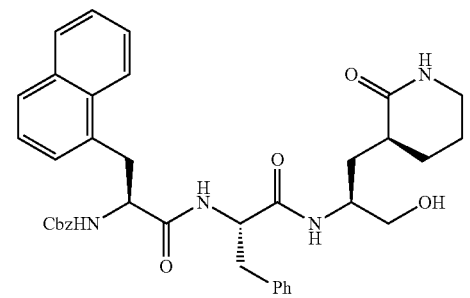

83

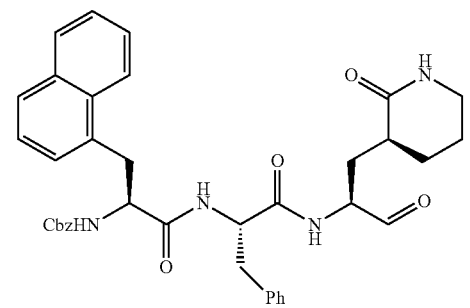

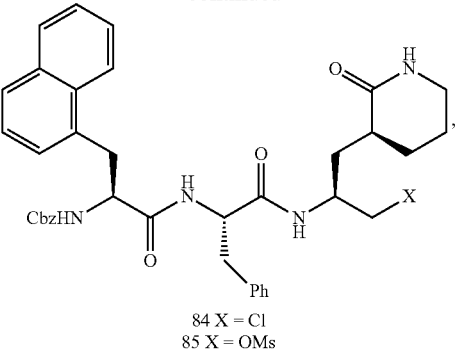

84 X = Cl
85 X = OMs and pharmaceutically acceptable salts and prodrugs thereof. Preferred compounds include the following:

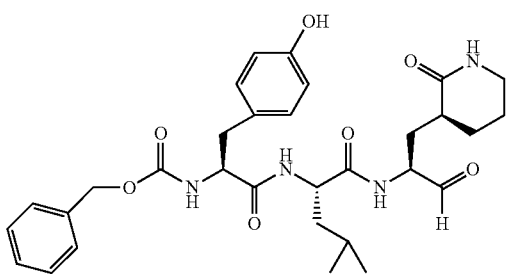

and

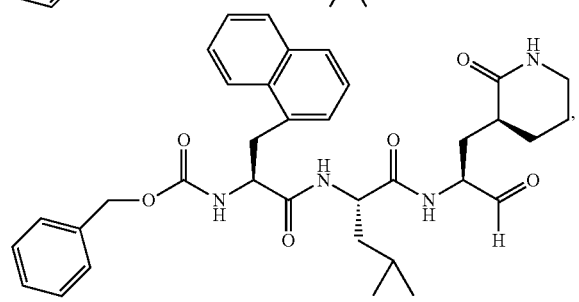

82 and pharmaceutically acceptable salts or prodrugs thereof.

DETAILED DESCRIPTION

In one embodiment, compounds and compositions useful in treating, preventing, or curing norovirus (NoV) infection are disclosed. Methods for treating, preventing, or curing NoV infection are also disclosed. In other embodiments, compounds for treating, preventing, or curing infections caused by Sapporo virus (human), Gastroenteritis, Jena virus (cattle), Murine norovirus (mouse), Fulminant organ dysfunction, Pistoia virus (lion), Hemorrhagic enteritis, Canine norovirus (dog), Swine43 (pig), Porcine enteric calicivirus (pig), Mink enteric calicivirus (mink), Rabbit hemorrhagic disease virus (rabbit), European brown hare syndrome virus (hare), Bovine enteric calicivirus/Newbury-1 virus (cattle), Bovine enteric calicivirus/Nebraska virus (cattle), Feline calicivirus (cat), Feline calicivirus-VS (cat), San Miguel sea lion virus (sea lion), Canine calicivirus No. 48 (dog), Tulane virus (monkey), St. Valerian virus/AB90 (pig), and Bayern virus (chicken) are disclosed.

The compounds described herein show inhibitory activity against NoV in cell-based assays. Therefore, the compounds can be used to treat or prevent a NoV in a host, or reduce the biological activity of the virus. The host can be a mammal, and in particular, a human, infected with NoV. The methods involve administering an effective amount of one or more of the compounds described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight, and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

As used herein, a "bridged alkyl" refers to a bicyclo- or tricyclo alkane, for example, a 2:1:1 bicyclohexane.

As used herein, a "spiro alkyl" refers to two rings that are attached at a single (quaternary) carbon atom.

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moieties. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups, including protecting groups for amines, are known to those skilled in the art of organic synthesis, and are described, for example, in Greene et al., Protective Groups in Organic Synthesis, supra. Specific examples include Carbobenzyloxy (Cbz), tosylate (Ts), nosylate, brosylate, mesylate, -tert-butoxycarbonyl (t-boc or boc), p-Methoxybenzyl carbonyl (Moz or MeOZ), 9-Fluorenylmethyloxycarbonyl (FMOC), Acetyl (Ac), Benzoyl (Bz), Benzyl (Bn), Carbamate, p-Methoxybenzyl (PMB), 3,4-Dimethoxybenzyl (DMPM), p-methoxyphenyl (PMP), Tosyl (Ts), Troc (trichloroethyl chloroformate), and other sulfonamides (such as Nosyl, mesyl, triflyl, and Nps).

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from the group consisting of straight, branched, or cyclic alkyl or lower alkyl, alkoxyalkyl, including, but not limited to methoxymethyl, aralkyl, including, but not limited to, benzyl, aryloxyalkyl, such as phenoxymethyl, aryl, including, but not limited to, phenyl, optionally substituted with halogen (F, Cl, Br, or I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituents selected from the group consisting of halogen, haloalkyl, alkyl, alkoxy, hydroxy, carboxyl derivatives, amido, amino, alkylamino, and dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human being. Veterinary applications, in certain indications, however, are clearly contemplated by the present invention (such as for use in treating chimpanzees).

The term "peptide" refers to a natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester) compound which, upon administration to a patient, provides the compound. Pharmaceutically-acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art.

The term "pharmaceutically acceptable salt or prodrug" is used throughout the specification to describe any pharmaceutically acceptable form (such as an ester) compound which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

II. Active Compounds

NoV is composed of small, icosahedral, non-enveloped viruses, from the Caliciviridae family, that have a linear, positive-sense, single-stranded RNA genome.

The virus particles are thought to attach to protein receptors via carbohydrate attachment factors (histo-blood group antigens). After entry and uncoating, translation occurs using cellular translation factors and the viral protease (PR) cleaves the synthesized polyprotein. The replication complex is then formed and the genome is replicated by the RNA-dependent RNA-polymerase (RdRp). The newly synthesized genomes are finally translated or are packaged into new virions to exit the cell.

The compounds described herein are active as NoV protease inhibitors. The NoV protease is also known as cysteine protease or thiol protease, containing a catalytic triad consisting of His30, Glu54, and Cys139.

In one embodiment, the compounds have the following formula:

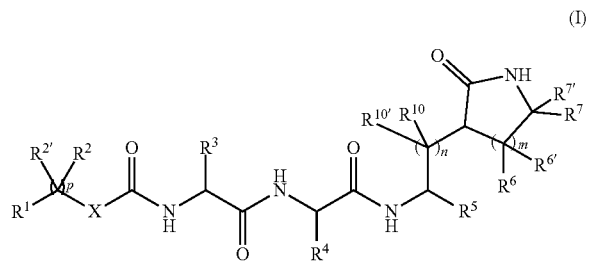

(I)

or a pharmaceutically acceptable salt or prodrug thereof, wherein:
$R^5$ is selected from

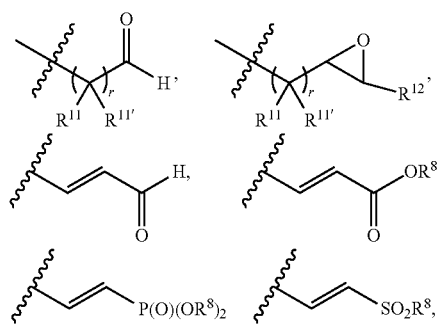

-continued

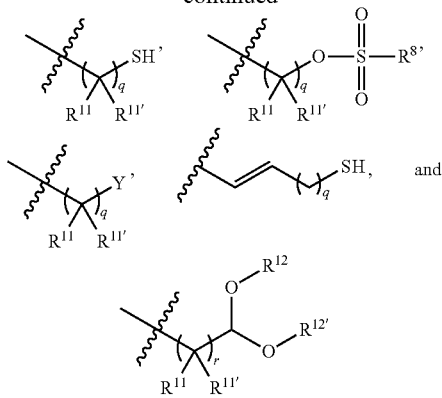

$R^2$, $R^{2'}$, $R^{10}$, $R^{10'}$, $R^{11}$ and $R^{11'}$ are, independently, hydrogen, $CF_3$, $C_{1-6}$ alkyl, $C_{1-6}$ haloalkyl, or $C_{2-6}$ alkenyl,
$R^{12}$ and $R^{12'}$ are, independently, $C_{1-6}$ alkyl, $C_{1-6}$ haloalkyl, or $C_{2-6}$ alkenyl,
$R^{12}$ and $R^{12'}$ can come together to form an optionally substituted $C_{3-7}$ ring, optionally containing an N, O, or S;
$R^8$ is, independently, optionally substituted $C_{1-6}$ alkyl, $C_{1-6}$ haloalkyl, $C_{2-6}$ alkenyl, aryl, or arylalkyl;
m, n, p and r are independently 0, 1, 2, 3, 4 or 5;
q is 1, 2, 3, 4 or 5
X is independently selected from a bond, O or NH,
Y is independently Cl, F, I or Br,
$R^{12}$ is hydrogen, $CF_3$, $CO_2R'$, $S(O)_2R'$, $S(O)_2N(R')_2$, $P(O)(OR')_2$, $C_{2-6}$ alkenyl, $C_{2-6}$ alkynyl, $C_{3-6}$ alkoxyalkyl, $C_{1-6}$ alkyl, arylalkoxycarbonyl, $C_{1-6}$ haloalkyl, heterocyclylalkyl, or $C_{1-6}$ hydroxyalkyl;
$R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl, or $R^6$ and $R^{6'}$, together with the carbon to which they are attached, form a carbonyl;
Each R' is, independently, H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl,
the R' groups, and other optionally substituted groups, can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, or phosphonate;
two R' residing on the same carbon or nitrogen atom can come together to form a $C_{3-6}$ ring optionally containing an N, O, or S;
$R^6$ and $R^{6'}$ can come together to form an optionally substituted double bond, a $C_{3-6}$ ring optionally containing an N, O, or S;
$R^7$ and $R^{7'}$ are, independently, hydrogen, $CF_3$, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl;

R$^7$ and R$^{7'}$ can come together to form an optionally substituted double bond or a C$_{3-6}$ ring optionally containing an N, O, or S;

R$^4$ and R$^3$ are, independently, optionally substituted C$_{1-6}$ alkyl, C$_{1-6}$ haloalkyl, C$_{2-8}$ alkoxyalkyl, arylalkyl, heteroarylalkyl, or —CH$_2$—R$^{4'}$.

R$^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring; and R$^1$ is optionally substituted aryl, heteroaryl, aryloxy, heteroaryloxy, arylalkoxy, or heteroarlalkoxy.

In another embodiment, the compounds have the following formula:

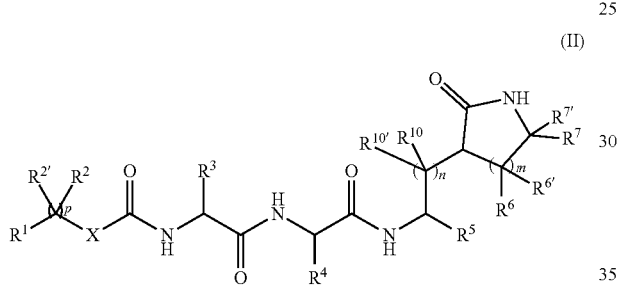

(II)

or a pharmaceutically acceptable salt or prodrug thereof, wherein:

R$^5$ is

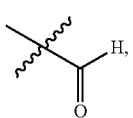

ketoamides, bisulfite salts,

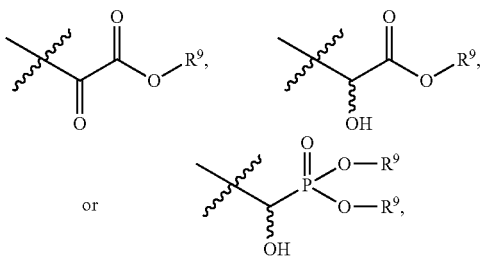

or

R$^9$ is, independently, optionally substituted C$_{1-6}$ alkyl, C$_{1-6}$ haloalkyl, aryl, heteroaryl, arylalkyl, or heteroarylalkyl, R$^4$ and R$^3$ are, independently, optionally substituted C$_{1-6}$ alkyl, C$_{1-6}$ haloalkyl, C$_{2-8}$ alkoxyalkyl, arylalkyl, heteroarylalkyl, or —CH$_2$—R$^{4'}$, R$^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

R$^1$ is optionally substituted aryl, heteroaryl, aryloxy, heteroaryloxy, arylalkoxy, or heteroarlalkoxy, R$^2$, R$^{2'}$, R$^{10}$ and R$^{10'}$ are, independently, hydrogen, CF$_3$, C$_{1-6}$ alkyl, C$_{1-6}$ haloalkyl, or C$_{2-6}$ alkenyl, X is, independently, a bond, O or NH, m, n, and p are, independently, 0, 1, 2, 3, 4 or 5;

when n and m are not 1: R$^6$ and R$^{6'}$ are, independently, hydrogen, halogen, CF$_3$, hydroxy, N(R')S(O)$_2$R', S(O)$_2$R', S(O)$_2$N(R')$_2$, C$_{1-6}$ alkoxy, C$_{2-6}$ alkenyl, cyano, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl; or R$^6$ and R$^{6'}$, together with the carbon to which they are attached, form a carbonyl, Each R' is, independently, H, C$_{1-6}$ alkyl, C$_{1-6}$ haloalkyl, C$_{1-6}$ alkoxy, C$_{2-6}$ alkenyl, C$_{2-6}$ alkynyl, C$_{3-6}$ cycloalkyl, aryl, heteroaryl, alkylaryl, or arylalkyl, the R' groups can optionally be substituted with one or more substituents, which substituents are, independently, halo, C$_{1-6}$ haloalkyl, C$_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, or phosphonate;

two R' residing on the same carbon or nitrogen atom can come together to form a C$_{3-6}$ ring optionally containing a N, O, or S heteroatom;

R$^6$ and R$^{6'}$ can come together to form an optionally substituted double bond or a C$_{3-6}$ ring optionally containing a N, O, or S heteroatom;

R$^7$ and R$^{7'}$ are, independently, hydrogen, CF$_3$, N(R')S(O)$_2$R', S(O)$_2$R', S(O)$_2$N(R')$_2$, C$_{1-6}$ alkoxy, C$_{2-6}$ alkenyl, cyano, C$_{2-6}$ alkynyl, C$_{3-6}$ alkoxyalkyl, alkoxycarbonyl, alkoxycarbonylalkyl, C$_{1-6}$ alkyl, arylalkoxycarbonyl, carboxy, C$_{1-6}$ haloalkyl, heterocyclylalkyl, or C$_{1-6}$ hydroxyalkyl; R$^7$ and R$^{7'}$ can come together to form an optionally substituted double bond or a C$_{3-6}$ ring optionally containing a N, O, or S heteroatom; and when n and m are 1, at least one or R$^2$, R$^6$, R$^{6'}$, R$^7$ and R$^{7'}$ is not hydrogen.

In yet another embodiment, the compounds have the following formula:

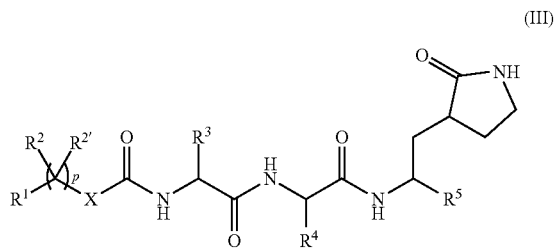

(III)

or a pharmaceutically acceptable salt or prodrug thereof, wherein:
R⁵ is

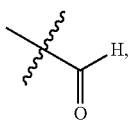

ketoamides, bisulfite salts,

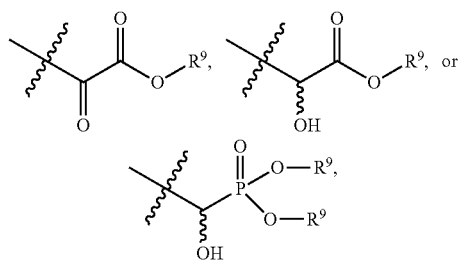

R⁹ is, independently, optionally substituted $C_{1-6}$ alkyl, $C_{1-6}$ haloalkyl, aryl, heteroaryl, arylalkyl, or heteroarylalkyl, R² and R²' are, independently, hydrogen, $CF_3$, $C_{1-6}$ alkyl, $C_{1-6}$ haloalkyl, or $C_{2-6}$ alkenyl, R³ is, independently, optionally substituted $C_{1-6}$ alkyl, $C_{1-6}$ haloalkyl, $C_{2-8}$ alkoxyalkyl, arylalkyl, heteroarylalkyl, or —CH₂—R⁴'.

R⁴ is, independently, optionally substituted $C_{1-6}$ haloalkyl, $C_{2-8}$ alkoxyalkyl, heteroarylalkyl, or —CH₂—R⁴', R⁴' is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

R¹ is optionally substituted aryl, heteroaryl, aryloxy, heteroaryloxy, arylalkoxy, or heteroarlalkoxy, p is 0, 1, 2, 3, 4 or 5; and X is a bond, O or NH.

In still another embodiment, the compounds have the following formula:

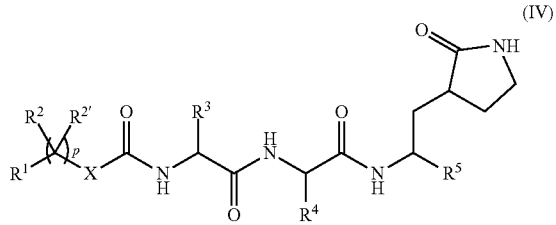

(IV)

or a pharmaceutically acceptable salt or prodrug thereof, wherein:
R⁵ is

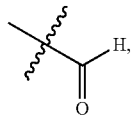

ketoamides, bisulfite salts,

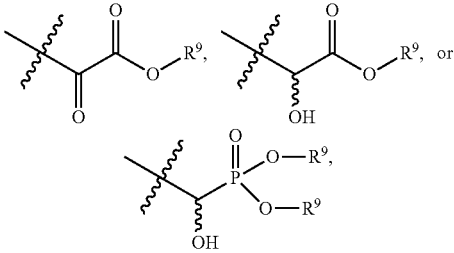

wherein a ketoamide has the formula —C(O)C(O)NHRˣ, where Rˣ is a branched or unbranched alkyl, cycloalkyl, or arylalkyl, and an α-hydroxyphosphonate of the formula —CH(O)(P=O)(ORʸ)₂, where each Rʸ is H, a substituted or unsubstituted alkyl, aryl, or arylalkyl, and a bisulfite has the formula —H(OH)SO₃⁻, and the salt is any pharmaceutically acceptable salt, R⁹ is, independently, optionally substituted $C_{1-6}$ alkyl, $C_{1-6}$ haloalkyl, aryl, heteroaryl, arylalkyl, or heteroarylalkyl, R⁴ is optionally substituted $C_{1-6}$ alkyl, cycloalkyl, aryl, arylalkyl, alkenyl, alkynyl, or a natural amino acid side chain, R⁴' is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

R¹ is optionally substituted aryl, heteroaryl, aryloxy, heteroaryloxy, arylalkoxy, or heteroarlalkoxy, p is 0, 1, 2, 3, 4 or 5;

X is, independently, a bond, O or NH,

R³ is, independently, optionally substituted $C_{1-6}$ haloalkyl, $C_{2-8}$ alkoxyalkyl, heteroarylalkyl, or —CH₂—R⁴*, and R² and R²' are, independently, hydrogen, $CF_3$, $C_{1-6}$ alkyl, $C_{1-6}$ haloalkyl, or $C_{2-6}$ alkenyl.

In still another embodiment, the compounds have the following formula:

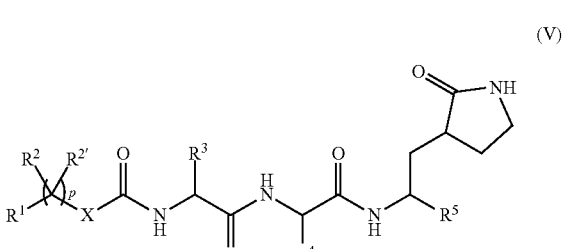

(V)

or a pharmaceutically acceptable salt or prodrug thereof, wherein:

$R^5$ is

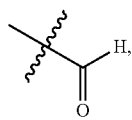

ketoamides, bisulfite salts,

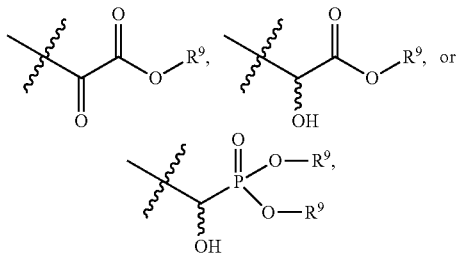

$R^9$ is, independently, optionally substituted $C_{1-6}$ alkyl, $C_{1-6}$ haloalkyl, aryl, heteroaryl, arylalkyl, or heteroarylalkyl, $R^4$ is optionally substituted $C_{1-6}$ alkyl, cycloalkyl, aryl, arylakyl, alkenyl, alkynyl, or a natural amino acid side chain, $R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

$R^1$ is optionally substituted aryl, heteroaryl, aryloxy, heteroaryloxy, arylalkoxy, or heteroarlalkoxy, p is 0, 1, 2, 3, 4 or 5;

X is, independently, a bond, O or NH, $R^3$ is, independently, optionally substituted $C_{1-6}$ haloalkyl, $C_{2-8}$ alkoxyalkyl, heteroarylalkyl, or —$CH_2$—$R^{4'}$, $R^2$ and $R^{2'}$ are, independently, $CF_3$, $C_{1-6}$ alkyl, $C_{1-6}$ haloalkyl, or $C_{2-6}$ alkenyl.

In still another embodiment, the compounds have the following formula:

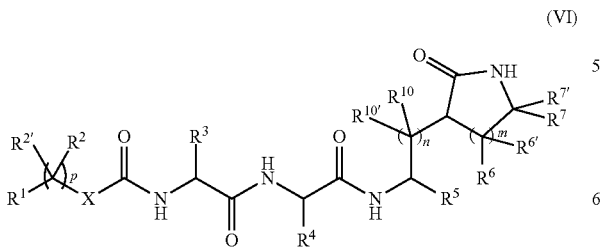

or a pharmaceutically acceptable salt or prodrug thereof, wherein:

$R^1$ is optionally substituted aryl, heteroaryl, aryloxy, heteroaryloxy, arylalkoxy, or heteroarylalkoxy, $R^2$ and $R^{2'}$ are, independently, H, —$NH_2$, —NH-carboxybenzyl (i.e., —NHCBz), $CF_3$, $C_{1-6}$ alkyl, $C_{1-6}$ haloalkyl, or $C_{2-6}$ alkenyl, where the —$NH_2$ can optionally be protected with an amine protecting group.

$R^3$ is, independently, optionally substituted $C_{1-6}$ haloalkyl, $C_{2-8}$ alkoxyalkyl, heteroarylalkyl, or —$CH_2$—$R^{4'}$, $R^4$ is optionally substituted $C_{1-6}$ alkyl, cycloalkyl, aryl, arylakyl, alkylaryl, alkenyl, alkynyl, or a natural amino acid side chain, $R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring;

$R^5$ is an acrylamide (—$C(R^2)$=$C(R^2)$—, $C_{1-6}$-haloalkyl, $C_{1-6}$ hydroxyalkyl, $C_{1-6}$-alkyl sulfonate, aryl sulfonate, heteroaryl sulfonate, $C_{1-6}$-alkyl sulfoxide, or $C_{1-6}$-ketoalkyl, wherein the alkyl moiety on any of these groups can be substituted with an epoxide (on two adjacent carbons), CN, OH, halo, keto, —$CF_3$, $R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl, or $R^6$ and $R^{6'}$, together with the carbon to which they are attached, form a carbonyl;

$R^6$ and $R^{6'}$ can come together to form an optionally substituted double bond, a $C_{3-6}$ ring optionally containing an N, O, or S;

$R^7$ and $R^{7'}$ are, independently, hydrogen, $CF_3$, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

$R^9$ is, independently, optionally substituted $C_{1-6}$ alkyl, $C_{1-6}$ haloalkyl, aryl, heteroaryl, arylalkyl, or heteroarylalkyl, $R^{10}$ and $R^{10'}$ are, independently, hydrogen, $CF_3$, $C_{1-6}$ alkyl, $C_{1-6}$ haloalkyl, or $C_{2-6}$ alkenyl, m, n and p are independently 0, 1, 2, 3, 4 or 5; and X is, independently, a bond, O or NH, and pharmaceutically acceptable salts and prodrugs thereof.

A subset of these compounds has the following formula:

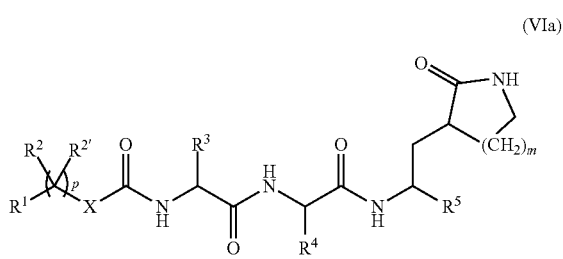

Individual compounds include the following:
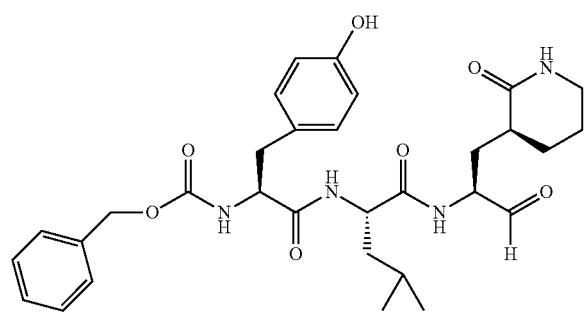
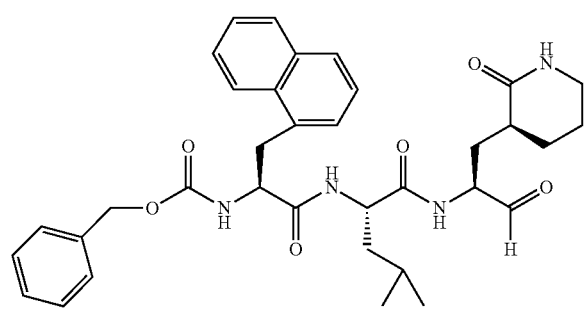
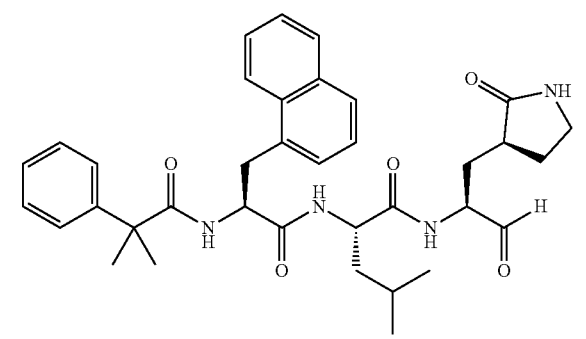
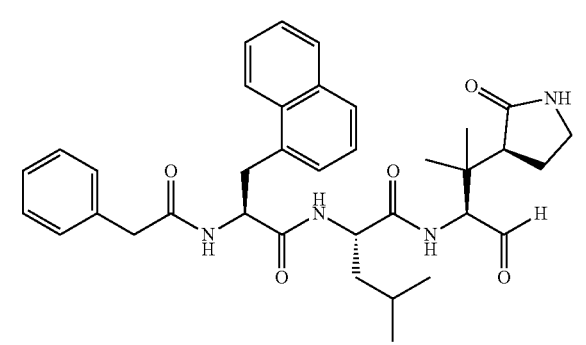
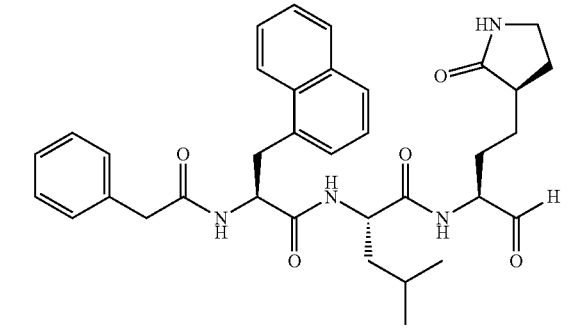
-continued
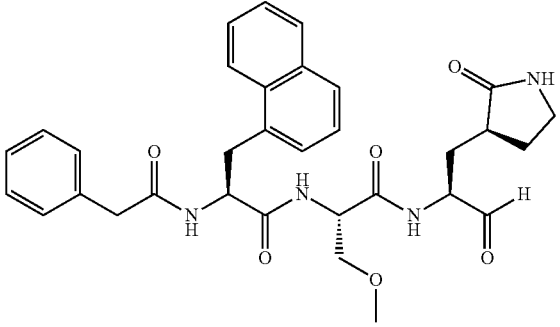
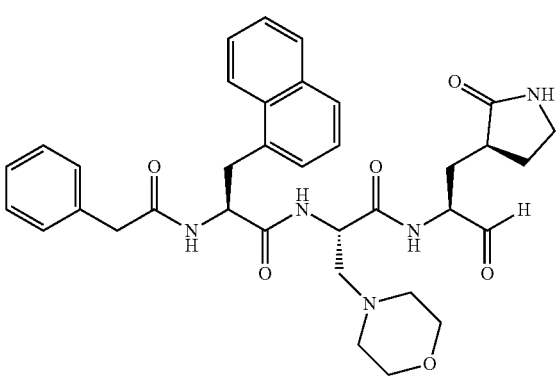
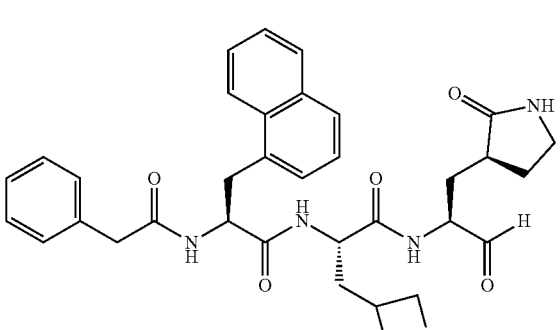
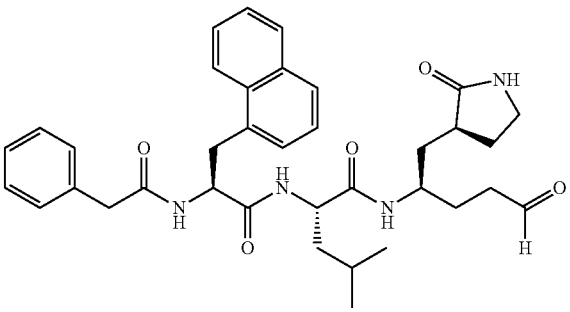
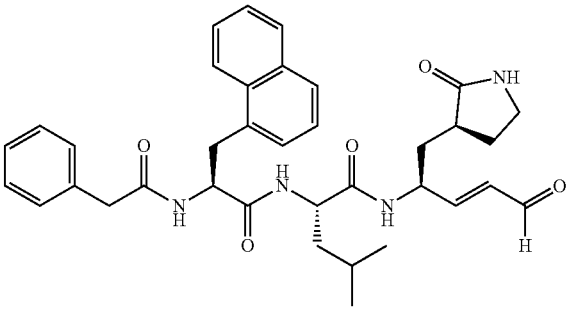

31
-continued
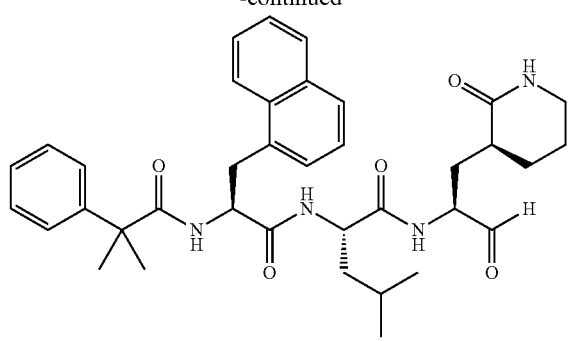
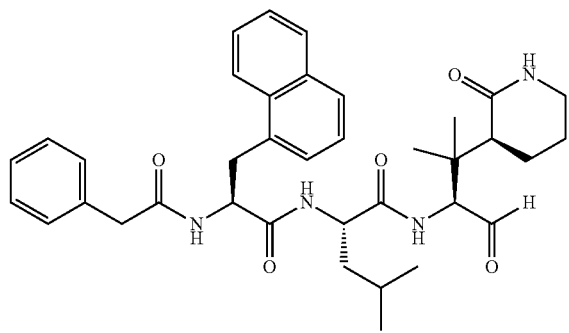
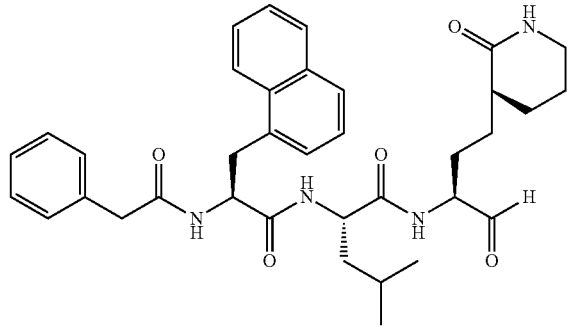
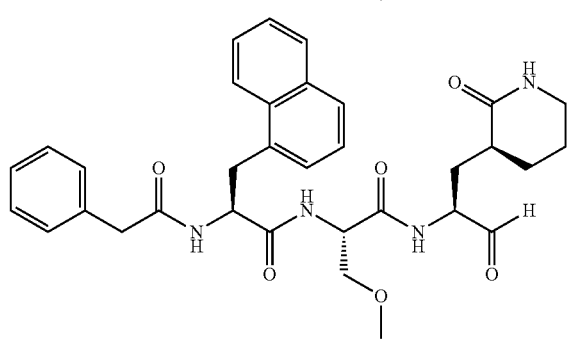
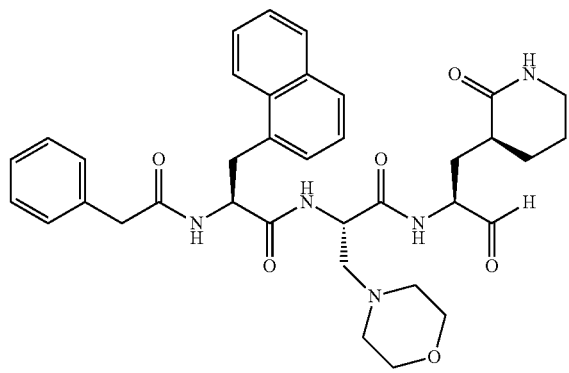
32
-continued
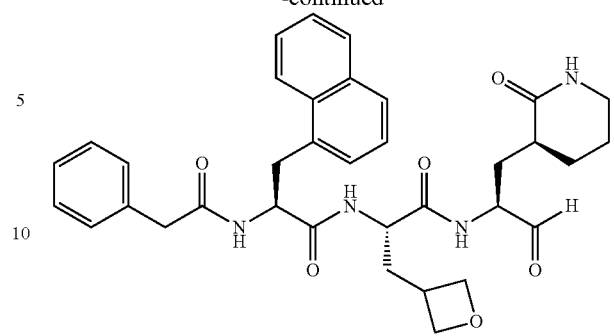
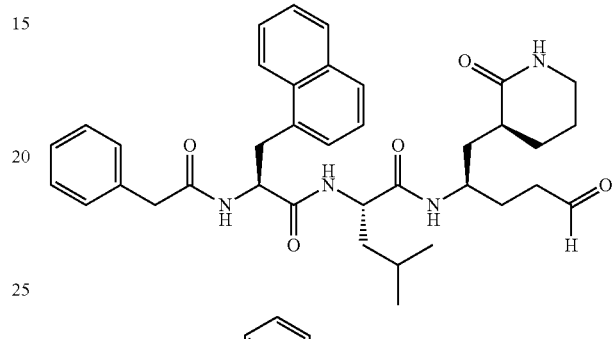
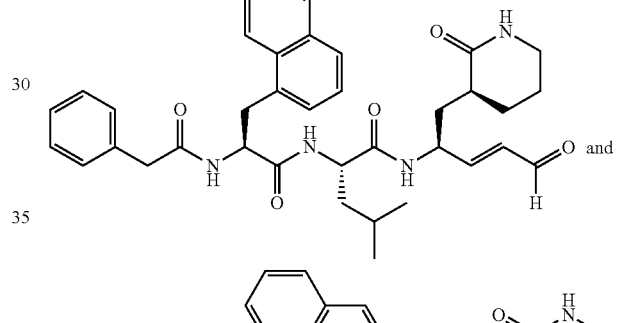 and
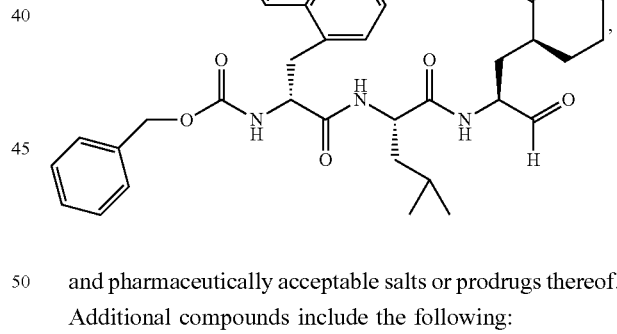
and pharmaceutically acceptable salts or prodrugs thereof.
Additional compounds include the following:
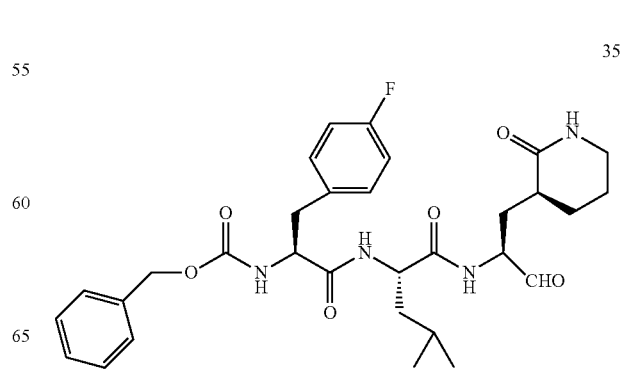

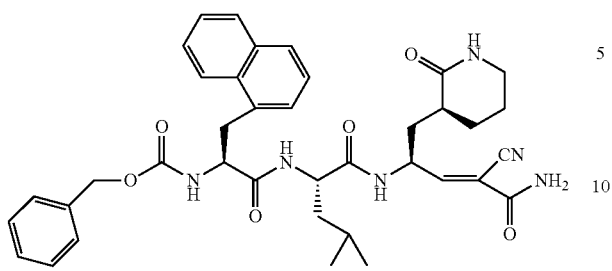
36
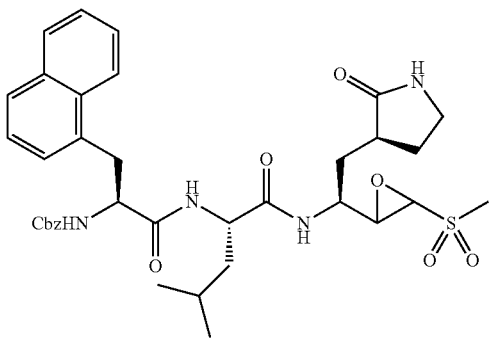
67
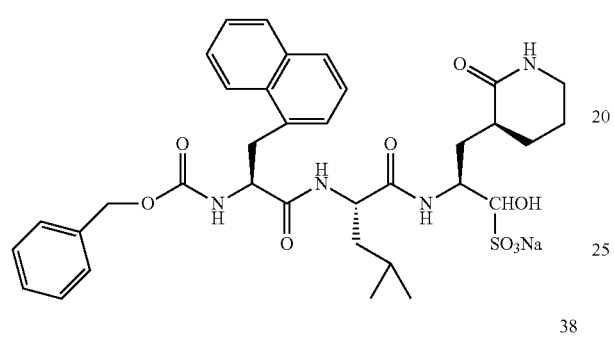
37
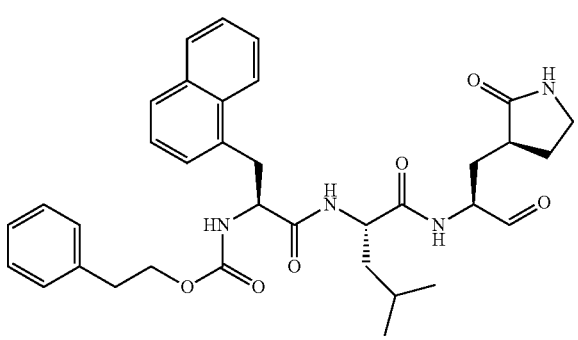
74
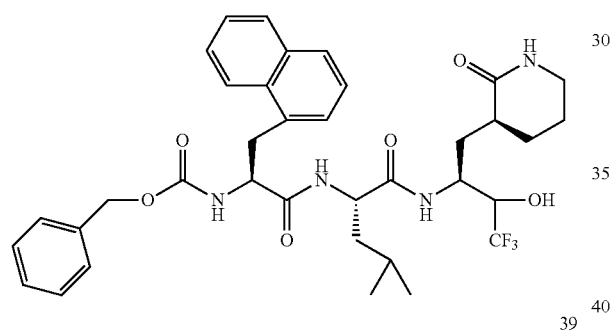
38
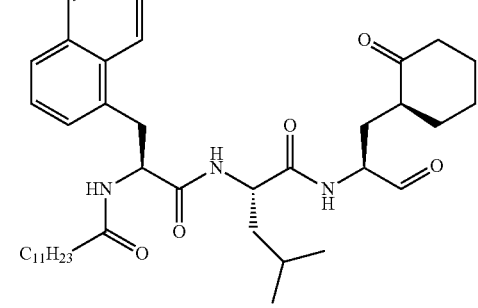
79
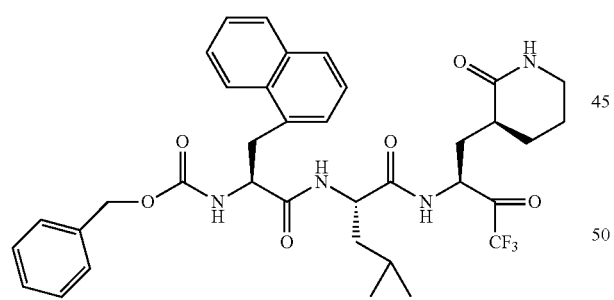
39
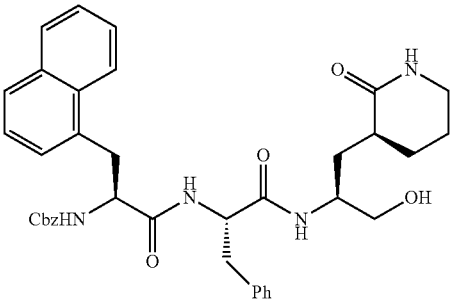
82
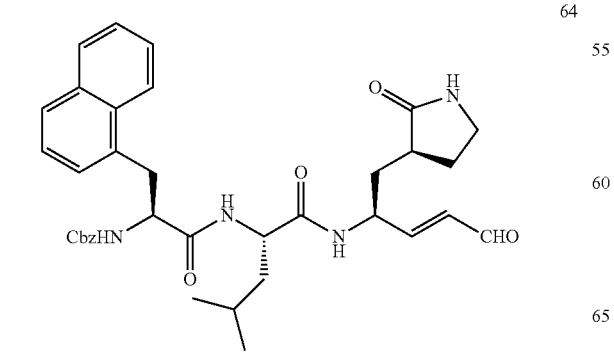
64
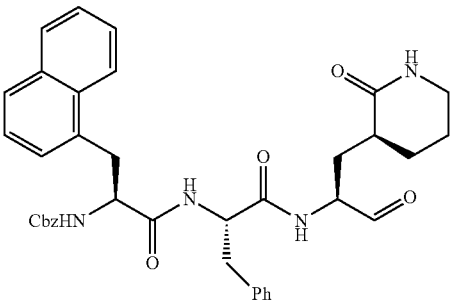
83

-continued

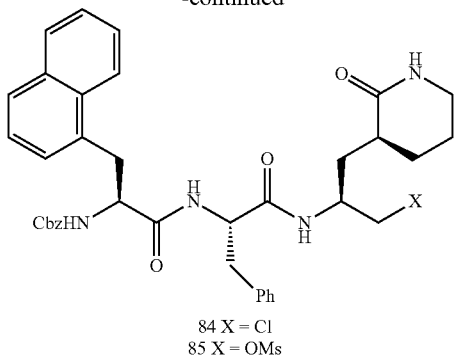

84 X = Cl
85 X = OMs

Preferred compounds include the following:

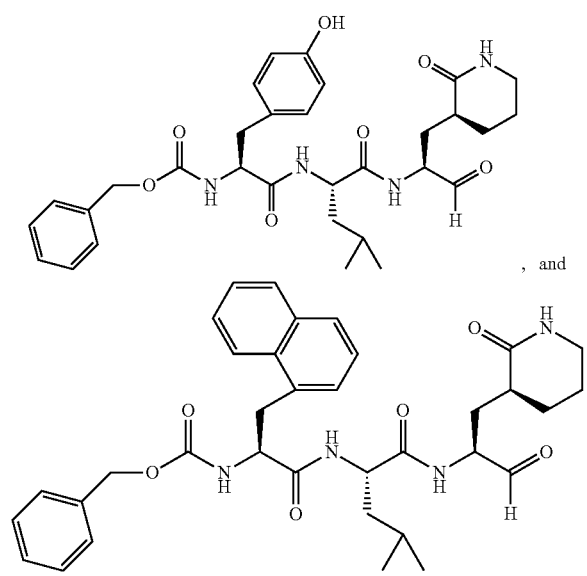

, and and pharmaceutically acceptable salts or prodrugs thereof.

III Stereoisomerism and Polymorphism

The compounds described herein can have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts. For certain transdermal applications, it can be preferred to use fatty acid salts of the compounds described herein. The fatty acid salts can help penetrate the stratum corneum. Examples of suitable salts include salts of the compounds with stearic acid, oleic acid, lineoleic acid, palmitic acid, caprylic acid, and capric acid.

Pharmaceutically acceptable salts can be obtained using standard procedures well known in the art, for example by reacting a sufficiently basic compound such as an amine with a suitable acid, affording a physiologically acceptable anion. In those cases where a compound includes multiple amine groups, the salts can be formed with any number of the amine groups. Alkali metal (e.g., sodium, potassium or lithium) or alkaline earth metal (e.g., calcium) salts of carboxylic acids can also be made.

A prodrug is a pharmacological substance that is administered in an inactive (or significantly less active) form and subsequently metabolized in vivo to an active metabolite. Getting more drug to the desired target at a lower dose is often the rationale behind the use of a prodrug and is generally attributed to better absorption, distribution, metabolism, and/or excretion (ADME) properties. Prodrugs are usually designed to improve oral bioavailability, with poor absorption from the gastrointestinal tract usually being the limiting factor. Additionally, the use of a prodrug strategy can increase the selectivity of the drug for its intended target thus reducing the potential for off target effects.

V. Isotopes

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. In other embodiments are examples of isotopes that are incorporated into the present compounds including isotopes of hydrogen, carbon, nitrogen, oxygen, fluorine and chlorine, such as, for example, $^2H$, $^3H$, $^{13}C$, $^{14}C$, $^{15}N$, $^{18}O$, $^{17}O$, $^{35}S$, $^{18}F$, $^{36}Cl$, respectively. Certain isotopically-labeled compounds described herein, for example those into which radioactive isotopes such as $^2H$ are incorporated, are useful in drug and/or substrate tissue distribution assays. Further, in some embodiments, substitution with isotopes such as deuterium, i.e., $^2H$, can affords certain therapeutic advantages resulting from greater metabolic stability, such as, for example, increased in vivo half-life or reduced dosage requirements.

VI. Methods of Treatment

The compounds described herein can be used to prevent, treat or cure Norovirus (NoV) infections.

Hosts, including but not limited to humans infected with NoV, or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, transdermally, subcutaneously, or topically, in liquid or solid form.

VII. Combination of Alternation Therapy

In one embodiment, the compounds of the invention can be employed together with at least one other antiviral agent, selected from the group consisting of polymerase inhibitors, anti-NoV nucleosides and their prodrugs, viral entry inhibitor, viral maturation inhibitor, and agents of distinct or unknown mechanism.

For example, when used to treat or prevent NoV infection, the active compound or its prodrug or pharmaceutically acceptable salt can be administered in combination or alternation with another anti-NoV agent including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

| Norovirus Therapies | | |
|---|---|---|
| FAMILY/ DRUG NAME | MECHANISM | COMPANY |
| CC-1845 | Polymerase inhibitor | Cocrystal Pharma |
| Zofran | Anti-emetic | Novartis |
| Immodium | Anti-diarrheal | Johnson and Johnson |
| Favipiravir | Viral polymerase, induces lethal mutagenesis | Toyama Chemical |
| Ribavirin | Viral polymerase, induces lethal mutagenesis | Kadmon Pharmaceuticals, LLC (RibaPak ®) |
| rupintrivir | Viral protease inhibitor; irreversible inhibitor of active site | Agouron Pharmaceuticals, Inc. |
| WP1130 | Small-molecule inhibitor of cellular deubiquitinases, Indirect activation of the unfolded protein response | Cayman Chemical |
| 2'-C-methylcytidine | Viral polymerase inhibitor | Cocrystal Pharma |
| IFN-λ specific inhibitors | Induces an antiviral state in the host cells | |
| Suramin (Germanin) | Non-nucleoside polymerase inhibitor | Bayer |
| NF203 | Non-nucleoside polymerase inhibitor | |
| PPNDS | Non-nucleoside polymerase inhibitor | Santa Cruz Biotechnology |

Structures for PPNDS and WP1130 are provided below:

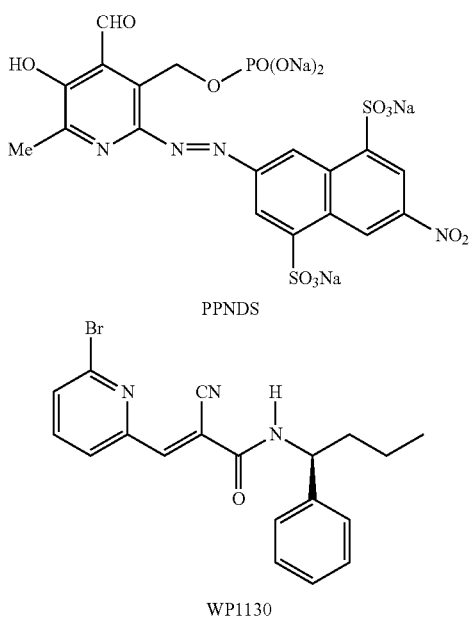

PPNDS

WP1130

VI. Pharmaceutical Compositions

Hosts, including but not limited to humans, infected with NoV can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 600 mg, preferably 70 to 600 mg of active ingredient per unit dosage form. An oral dosage of 1-400 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral, although for certain patients a sterile injectable form can be given sc, ip or iv. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

Transdermal Formulations

In some embodiments, the compositions are present in the form of transdermal formulations, such as that used in the FDA-approved agonist rotigitine transdermal (Neupro patch). Another suitable formulation is that described in U.S. Publication No. 20080050424, entitled "Transdermal Therapeutic System for Treating Parkinsonism." This formulation includes a silicone or acrylate-based adhesive, and can include an additive having increased solubility for the active substance, in an amount effective to increase dissolving capacity of the matrix for the active substance.

The transdermal formulations can be single-phase matrices that include a backing layer, an active substance-containing self-adhesive matrix, and a protective film to be removed prior to use. More complicated embodiments contain multiple-layer matrices that may also contain non-adhesive layers and control membranes. If a polyacrylate adhesive is used, it can be crosslinked with multivalent metal ions such as zinc, calcium, aluminum, or titanium ions, such as aluminum acetylacetonate and titanium acetylacetonate.

When silicone adhesives are used, they are typically polydimethylsiloxanes. However, other organic residues such as, for example, ethyl groups or phenyl groups may in principle be present instead of the methyl groups. Because the active compounds are amines, it may be advantageous to use amine-resistant adhesives. Representative amine-resistant adhesives are described, for example, in EP 0 180 377.

Representative acrylate-based polymer adhesives include acrylic acid, acrylamide, hexylacrylate, 2-ethylhexylacrylate, hydroxyethylacrylate, octylacrylate, butylacrylate, methylacrylate, glycidylacrylate, methacrylic acid, methacrylamide, hexylmethacrylate, 2-ethylhexylmethacrylate, octylmethacrylate, methylmethacrylate, glycidylmethacrylate, vinylacetate, vinylpyrrolidone, and combinations thereof.

The adhesive must have a suitable dissolving capacity for the active substance, and the active substance most be able to move within the matrix, and be able to cross through the contact surface to the skin. Those of skill in the art can readily formulate a transdermal formulation with appropriate transdermal transport of the active substance.

Certain pharmaceutically acceptable salts tend to be more preferred for use in transdermal formulations, because they can help the active substance pass the barrier of the stratum corneum. Examples include fatty acid salts, such as stearic acid and oleic acid salts. Oleate and stearate salts are relatively lipophilic, and can even act as a permeation enhancer in the skin.

Permeation enhancers can also be used. Representative permeation enhancers include fatty alcohols, fatty acids, fatty acid esters, fatty acid amides, glycerol or its fatty acid esters, N-methylpyrrolidone, terpenes such as limonene, alpha-pinene, alpha-terpineol, carvone, carveol, limonene oxide, pinene oxide, and 1,8-eucalyptol.

The patches can generally be prepared by dissolving or suspending the active agent in ethanol or in another suitable organic solvent, then adding the adhesive solution with stirring. Additional auxiliary substances can be added either to the adhesive solution, the active substance solution or to the active substance-containing adhesive solution. The solution can then be coated onto a suitable sheet, the solvents removed, a backing layer laminated onto the matrix layer, and patches punched out of the total laminate.

Nanoparticulate Compositions

The compounds described herein can also be administered in the form of nanoparticulate compositions.

In one embodiment, the controlled release nanoparticulate formulations comprise a nanoparticulate active agent to be administered and a rate-controlling polymer which functions to prolong the release of the agent following administration. In this embodiment, the compositions can release the active agent, following administration, for a time period ranging from about 2 to about 24 hours or up to 30 days or longer. Representative controlled release formulations including a nanoparticulate form of the active agent are described, for example, in U.S. Pat. No. 8,293,277.

Nanoparticulate compositions comprise particles of the active agents described herein, having a non-crosslinked surface stabilizer adsorbed onto, or associated with, their surface.

The average particle size of the nanoparticulates is typically less than about 800 nm, more typically less than about 600 nm, still more typically less than about 400 nm, less than about 300 nm, less than about 250 nm, less than about 100 nm, or less than about 50 nm. In one aspect of this embodiment, at least 50% of the particles of active agent have an average particle size of less than about 800, 600, 400, 300, 250, 100, or 50 nm, respectively, when measured by light scattering techniques.

A variety of surface stabilizers are typically used with nanoparticulate compositions to prevent the particles from clumping or aggregating. Representative surface stabilizers are selected from the group consisting of gelatin, lecithin, dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidal silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethyl-cellulose phthalate, noncrystalline cellulose, magnesium aluminum silicate, triethanolamine, polyvinyl alcohol, polyvinylpyrrolidone, tyloxapol, poloxamers, poloxamines, poloxamine 908, dialkylesters of sodium sulfosuccinic acid, sodium lauryl sulfate, an alkyl aryl polyether sulfonate, a mixture of sucrose stearate and sucrose distearate, p-isononylphenoxypoly-(glycidol), SA9OHCO, decanoyl-N-methylglucamide, n-decyl-D-glucopyranoside, n-decyl-D-maltopyranoside, n-dodecyl-D-glucopyranoside, n-dodecyl-D-maltoside, heptanoyl-N-methylglucamide, n-heptyl-D-glucopyranoside, n-heptyl-D-thioglucoside, n-hexyl-D-glucopyranoside, nonanoyl-N-methylglucamide, n-nonyl-D-glucopyranoside, octanoyl-N-methylglucamide, n-octyl-D-glucopyranoside, and octyl-D-thioglucopyranoside. Lysozymes can also be used as surface stabilizers for nanoparticulate compositions. Certain nanoparticles such as poly(lactic-co-glycolic acid)

(PLGA)-nanoparticles are known to target the liver when given by intravenous (IV) or subcutaneously (SQ).

In one embodiment, the nanoparticles or other drug delivery vehicles are targeted to the liver. One such type of liver-targeted drug delivery vehicle is described in Park, et al., Mol Imaging. February 2011; 10(1): 69-77, and uses Glypican-3 (GPC3) as a molecular target. Park taught using this target for hepatocellular carcinoma (HCC), a primary liver cancer frequently caused by chronic persistent hepatitis.

In one aspect of this embodiment, this drug delivery vehicle is also used to target therapeutics to the liver to treat viral infections. Further, since the compounds described herein have anti-cancer uses, this type of system can target the compounds to the liver and treat liver cancers. GPC3 is a heparan sulfate proteoglycan that is not expressed in normal adult tissues, but significantly over-expressed in up to 80% of human HCC's. GPC3 can be targeted, for example, using antibody-mediated targeting and binding (See Hsu, et al., Cancer Res. 1997; 57:5179-84).

Another type of drug delivery system for targeting the liver is described in U.S. Pat. No. 7,304,045. The '045 patent discloses a dual-particle tumor or cancer targeting system that includes a first ligand-mediated targeting nanoparticle conjugated with galactosamine, with the ligand being on a target cell. The first nanoparticle includes poly(γ-glutamic acid)/poly(lactide) block copolymers and n antiviral compound, which in this case is a compound described herein, and in the '045 patent, was gancyclovir. A second nanoparticle includes poly(γ-glutamic acid)/poly(lactide) block copolymers, an endothelial cell-specific promoter, and a (herpes-simplex-virus)-(thymidine kinase) gene constructed plasmid, and provides enhanced permeability and retention-mediated targeting. The first and said second nanoparticles are mixed in a solution configured for delivering to the liver. When the disorder to be treated is a liver tumor or cancer, the delivery can be directly to, or adjacent to, the liver tumor or cancer.

Representative rate controlling polymers into which the nanoparticles can be formulated include chitosan, polyethylene oxide (PEO), polyvinyl acetate phthalate, gum arabic, agar, guar gum, cereal gums, dextran, casein, gelatin, pectin, carrageenan, waxes, shellac, hydrogenated vegetable oils, polyvinylpyrrolidone, hydroxypropyl cellulose (HPC), hydroxyethyl cellulose (HEC), hydroxypropyl methylcellulose (HPMC), sodium carboxymethylcellulose (CMC), poly(ethylene) oxide, alkyl cellulose, ethyl cellulose, methyl cellulose, carboxymethyl cellulose, hydrophilic cellulose derivatives, polyethylene glycol, polyvinylpyrrolidone, cellulose acetate, cellulose acetate butyrate, cellulose acetate phthalate, cellulose acetate trimellitate, polyvinyl acetate phthalate, hydroxypropylmethyl cellulose phthalate, hydroxypropylmethyl cellulose acetate succinate, polyvinyl acetaldiethylamino acetate, poly(alkylmethacrylate), poly(vinyl acetate), polymers derived from acrylic or methacrylic acid and their respective esters, and copolymers derived from acrylic or methacrylic acid and their respective esters.

Methods of making nanoparticulate compositions are described, for example, in U.S. Pat. Nos. 5,518,187 and 5,862,999, both for "Method of Grinding Pharmaceutical Substances;" U.S. Pat. No. 5,718,388, for "Continuous Method of Grinding Pharmaceutical Substances;" and U.S. Pat. No. 5,510,118 for "Process of Preparing Therapeutic Compositions Containing Nanoparticles."

Nanoparticulate compositions are also described, for example, in U.S. Pat. No. 5,298,262 for "Use of Ionic Cloud Point Modifiers to Prevent Particle Aggregation During Sterilization;" U.S. Pat. No. 5,302,401 for "Method to Reduce Particle Size Growth During Lyophilization;" U.S. Pat. No. 5,318,767 for "X-Ray Contrast Compositions Useful in Medical Imaging;" U.S. Pat. No. 5,326,552 for "Novel Formulation For Nanoparticulate X-Ray Blood Pool Contrast Agents Using High Molecular Weight Non-ionic Surfactants;" U.S. Pat. No. 5,328,404 for "Method of X-Ray Imaging Using Iodinated Aromatic Propanedioates;" U.S. Pat. No. 5,336,507 for "Use of Charged Phospholipids to Reduce Nanoparticle Aggregation;" U.S. Pat. No. 5,340,564 for Formulations Comprising Olin 10-G to Prevent Particle Aggregation and Increase Stability;" U.S. Pat. No. 5,346,702 for "Use of Non-Ionic Cloud Point Modifiers to Minimize Nanoparticulate Aggregation During Sterilization;" U.S. Pat. No. 5,349,957 for "Preparation and Magnetic Properties of Very Small Magnetic-Dextran Particles;" U.S. Pat. No. 5,352,459 for "Use of Purified Surface Modifiers to Prevent Particle Aggregation During Sterilization;" U.S. Pat. Nos. 5,399,363 and 5,494,683, both for "Surface Modified Anticancer Nanoparticles;" U.S. Pat. No. 5,401,492 for "Water Insoluble Non-Magnetic Manganese Particles as Magnetic Resonance Enhancement Agents;" U.S. Pat. No. 5,429,824 for "Use of Tyloxapol as a Nanoparticulate Stabilizer;" U.S. Pat. No. 5,447,710 for "Method for Making Nanoparticulate X-Ray Blood Pool Contrast Agents Using High Molecular Weight Non-ionic Surfactants;" U.S. Pat. No. 5,451,393 for "X-Ray Contrast Compositions Useful in Medical Imaging;" U.S. Pat. No. 5,466,440 for "Formulations of Oral Gastrointestinal Diagnostic X-Ray Contrast Agents in Combination with Pharmaceutically Acceptable Clays;" U.S. Pat. No. 5,470,583 for "Method of Preparing Nanoparticle Compositions Containing Charged Phospholipids to Reduce Aggregation;" U.S. Pat. No. 5,472,683 for "Nanoparticulate Diagnostic Mixed Carbamic Anhydrides as X-Ray Contrast Agents for Blood Pool and Lymphatic System Imaging;" U.S. Pat. No. 5,500,204 for "Nanoparticulate Diagnostic Dimers as X-Ray Contrast Agents for Blood Pool and Lymphatic System Imaging;" U.S. Pat. No. 5,518,738 for "Nanoparticulate NSAID Formulations;" U.S. Pat. No. 5,521,218 for "Nanoparticulate Tododipamide Derivatives for Use as X-Ray Contrast Agents;" U.S. Pat. No. 5,525,328 for "Nanoparticulate Diagnostic Diatrizoxy Ester X-Ray Contrast Agents for Blood Pool and Lymphatic System Imaging;" U.S. Pat. No. 5,543,133 for "Process of Preparing X-Ray Contrast Compositions Containing Nanoparticles;" U.S. Pat. No. 5,552,160 for "Surface Modified NSAID Nanoparticles;" U.S. Pat. No. 5,560,931 for "Formulations of Compounds as Nanoparticulate Dispersions in Digestible Oils or Fatty Acids;" U.S. Pat. No. 5,565,188 for "Polyalkylene Block Copolymers as Surface Modifiers for Nanoparticles;" U.S. Pat. No. 5,569,448 for "Sulfated Non-ionic Block Copolymer Surfactant as Stabilizer Coatings for Nanoparticle Compositions;" U.S. Pat. No. 5,571,536 for "Formulations of Compounds as Nanoparticulate Dispersions in Digestible Oils or Fatty Acids;" U.S. Pat. No. 5,573,749 for "Nanoparticulate Diagnostic Mixed Carboxylic Anhydrides as X-Ray Contrast Agents for Blood Pool and Lymphatic System Imaging;" U.S. Pat. No. 5,573,750 for "Diagnostic Imaging X-Ray Contrast Agents;" U.S. Pat. No. 5,573,783 for "Redispersible Nanoparticulate Film Matrices With Protective Overcoats;" U.S. Pat. No. 5,580,579 for "Site-specific Adhesion Within the GI Tract Using Nanoparticles Stabilized by High Molecular Weight, Linear Poly (ethylene Oxide) Polymers;" U.S. Pat. No. 5,585,108 for "Formulations of Oral Gastrointestinal Therapeutic Agents in Combination with Pharmaceutically Acceptable Clays;"

U.S. Pat. No. 5,587,143 for "Butylene Oxide-Ethylene Oxide Block Copolymers Surfactants as Stabilizer Coatings for Nanoparticulate Compositions;" U.S. Pat. No. 5,591,456 for "Milled Naproxen with Hydroxypropyl Cellulose as Dispersion Stabilizer;" U.S. Pat. No. 5,593,657 for "Novel Barium Salt Formulations Stabilized by Non-ionic and Anionic Stabilizers;" U.S. Pat. No. 5,622,938 for "Sugar Based Surfactant for Nanocrystals;" U.S. Pat. No. 5,628,981 for "Improved Formulations of Oral Gastrointestinal Diagnostic X-Ray Contrast Agents and Oral Gastrointestinal Therapeutic Agents;" U.S. Pat. No. 5,643,552 for "Nanoparticulate Diagnostic Mixed Carbonic Anhydrides as X-Ray Contrast Agents for Blood Pool and Lymphatic System Imaging;" U.S. Pat. No. 5,718,388 for "Continuous Method of Grinding Pharmaceutical Substances;" U.S. Pat. No. 5,718,919 for "Nanoparticles Containing the R(−)Enantiomer of Ibuprofen;" U.S. Pat. No. 5,747,001 for "Aerosols Containing Beclomethasone Nanoparticle Dispersions;" U.S. Pat. No. 5,834,025 for "Reduction of Intravenously Administered Nanoparticulate Formulation Induced Adverse Physiological Reactions;" U.S. Pat. No. 6,045,829 "Nanocrystalline Formulations of Human Immunodeficiency Virus (HIV) Protease Inhibitors Using Cellulosic Surface Stabilizers;" U.S. Pat. No. 6,068,858 for "Methods of Making Nanocrystalline Formulations of Human Immunodeficiency Virus (HIV) Protease Inhibitors Using Cellulosic Surface Stabilizers;" U.S. Pat. No. 6,153,225 for "Injectable Formulations of Nanoparticulate Naproxen;" U.S. Pat. No. 6,165,506 for "New Solid Dose Form of Nanoparticulate Naproxen;" U.S. Pat. No. 6,221,400 for "Methods of Treating Mammals Using Nanocrystalline Formulations of Human Immunodeficiency Virus (HIV) Protease Inhibitors;" U.S. Pat. No. 6,264,922 for "Nebulized Aerosols Containing Nanoparticle Dispersions;" U.S. Pat. No. 6,267,989 for "Methods for Preventing Crystal Growth and Particle Aggregation in Nanoparticle Compositions;" U.S. Pat. No. 6,270,806 for "Use of PEG-Derivatized Lipids as Surface Stabilizers for Nanoparticulate Compositions;" U.S. Pat. No. 6,316,029 for "Rapidly Disintegrating Solid Oral Dosage Form," U.S. Pat. No. 6,375,986 for "Solid Dose Nanoparticulate Compositions Comprising a Synergistic Combination of a Polymeric Surface Stabilizer and Dioctyl Sodium Sulfosuccinate;" U.S. Pat. No. 6,428,814 for "Bioadhesive nanoparticulate compositions having cationic surface stabilizers;" U.S. Pat. No. 6,431,478 for "Small Scale Mill;" and U.S. Pat. No. 6,432,381 for "Methods for targeting drug delivery to the upper and/or lower gastrointestinal tract," all of which are specifically incorporated by reference. In addition, U.S. Patent Application No. 20020012675 A1, published on Jan. 31, 2002, for "Controlled Release Nanoparticulate Compositions," describes nanoparticulate compositions, and is specifically incorporated by reference.

The nanoparticle formulations including the compounds described herein, and also in the form of a prodrug or a salt, can be used to treat or prevent infections by hepatitis B virus.

Amorphous small particle compositions are described, for example, in U.S. Pat. No. 4,783,484 for "Particulate Composition and Use Thereof as Antimicrobial Agent;" U.S. Pat. No. 4,826,689 for "Method for Making Uniformly Sized Particles from Water-Insoluble Organic Compounds;" U.S. Pat. No. 4,997,454 for "Method for Making Uniformly-Sized Particles From Insoluble Compounds;" U.S. Pat. No. 5,741,522 for "Ultrasmall, Non-aggregated Porous Particles of Uniform Size for Entrapping Gas Bubbles Within and Methods;" and U.S. Pat. No. 5,776,496, for "Ultrasmall Porous Particles for Enhancing Ultrasound Back Scatter."

Controlled Release Formulations

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:

$Boc_2O$ Di-tert-butyl dicarbonate
CbzCl Benzyl chloroformate
CDI N,N'-Carbonyldiimidazole
DCE dichloroethane
DCM Dichloromethane
DIPEA diisopropyl ethyl amine (Hünig's base)
DMSO dimethylsulfoxide
EDC 1-ethyl-3-(3-dimethyl)aminopropyl)carbodiimide hydrochloride
$Et_3N$ Triethylamine
EtOAc ethyl acetate
EtOH ethanol
h hour
HOBt Hydroxybenzotriazole
KOAC Potassium acetate
LiHMDS Lithium bis(trimethylsilyl)amide
M molar
mCPBA meta-Chloroperoxybenzoic acid
MeOH Methanol
$MePPh_3Br$ Methyltriphenylphosphonium bromide
MsCl Methanesulfonyl chloride
min minute
$Py·SO_3$ Sulfur trioxide pyridine complex
rt or RT room temperature
TFA trifluoroacetic acid
THF tetrahydrofuran
TLC Thin layer chromatography
$TMSCF_3$ trimethyl(trifluoromethyl)silane IX. General Methods for Preparing Active Compounds Methods for the facile preparation of active compounds are known in the art and result from the selective combination of known methods. The compounds disclosed herein can be prepared as described in detail below, or by other methods known to those skilled in the art. It will be understood by one of ordinary skill in the art that variations of detail can be made without departing from the spirit and in no way limiting the scope of the present invention.

The various reaction schemes are summarized below.

Scheme 1 is a non-limiting example of the synthesis of active compounds of the present invention, and in particular, a synthetic approach to compound A.

Scheme 2 is a non-limiting example of the synthesis of intermediates of the present invention, and in particular, a synthetic approach to compound XVI, XVIII, XIX and XXI.

Scheme 3 is a non-limiting example of the synthesis of active compounds of the present invention, and in particular, a synthetic approach to compound B-D.

Scheme 4 is a non-limiting example of the synthesis of active compounds of the present invention, and in particular, a synthetic approach to compound E.

Compounds of formula A can be prepared by first reaction of an amino acid derivative of general formula I with an alcohol. Intermediate II can be then N-protected for example, by treatment with $Boc_2O$ in the presence of a base such as $Et_3N$ and then reacted with a compound of general formula IV in presence of a base such as LiHMDS. Cyano derivative of general formula V can be then reduced and finally cyclized to give VII. Intermediate VII can be deprotected for example, in the presence of TFA when Boc was used as a protecting group, and reacted with an amino acid of general formula VIII in the presence of peptide coupling reagents like EDC and HOBt. After deprotection for example, in the presence of TFA when Boc was used as a protecting group, compound of general formula IX can be reacted in presence peptide coupling reagents like EDC and HOBt with compound XII, prepared by reaction of amino acid of general formula X and halogenated reagent XI in the presence of a base such as $NaHCO_3$. Esters of general formula XIII can then be reduced with, for instance, $LiAlH_4$ to give compounds of general formula A.

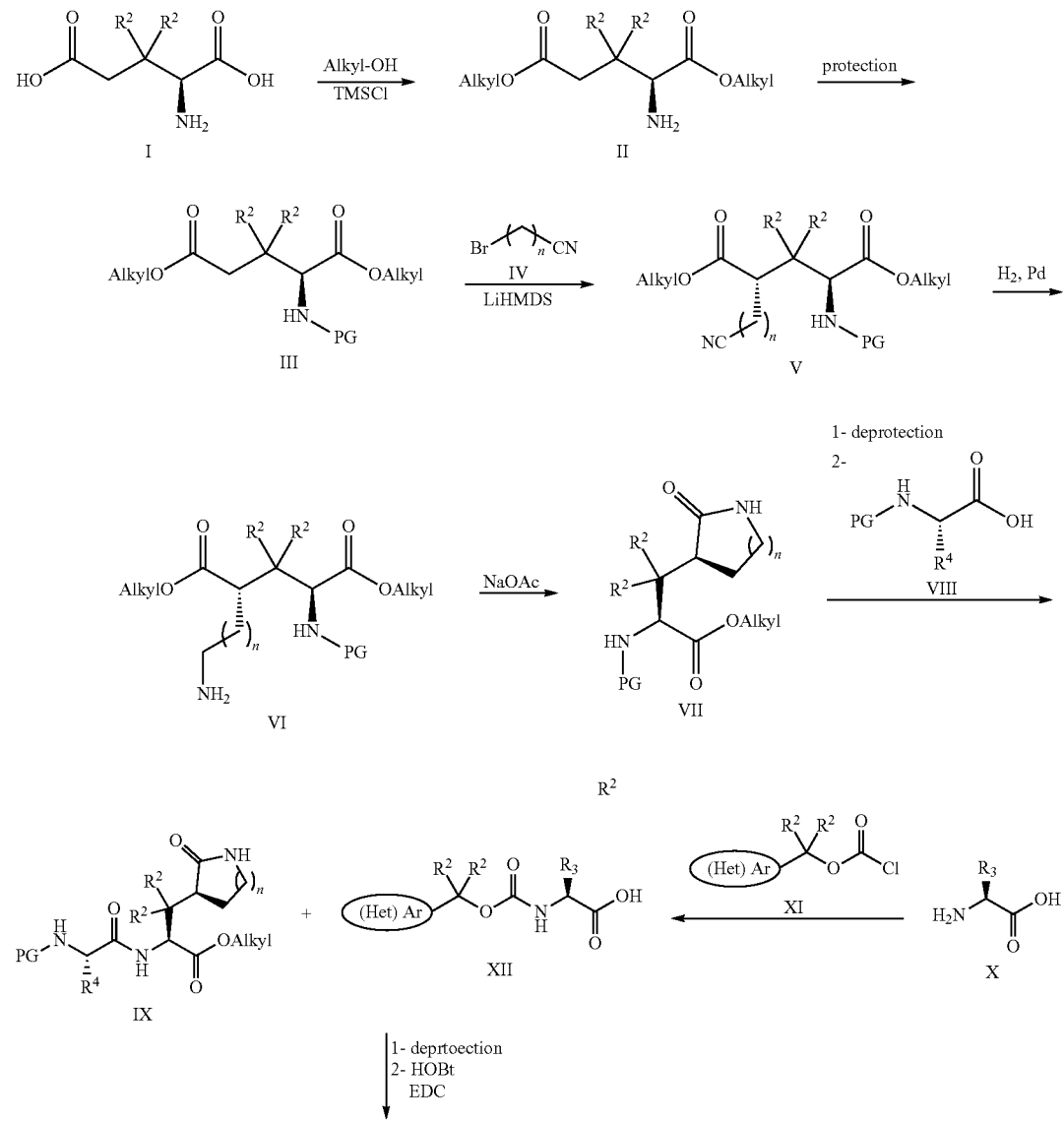

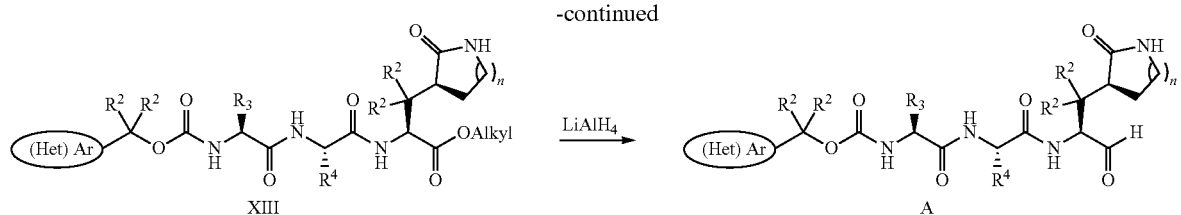
Intermediates of formula XVI, XVIII, XIX and XXI can be prepared by first reduction of compound of general formula VI, with a reducing agent such as for instance LiBH$_4$ followed by oxidation to form aldehyde of general formula XIV and then reaction with either compounds XV, XVII, XX or MePPh$_3$Br.
Scheme 2 A synthetic approach to intermediates XVI, XVIII, XIX and XXI
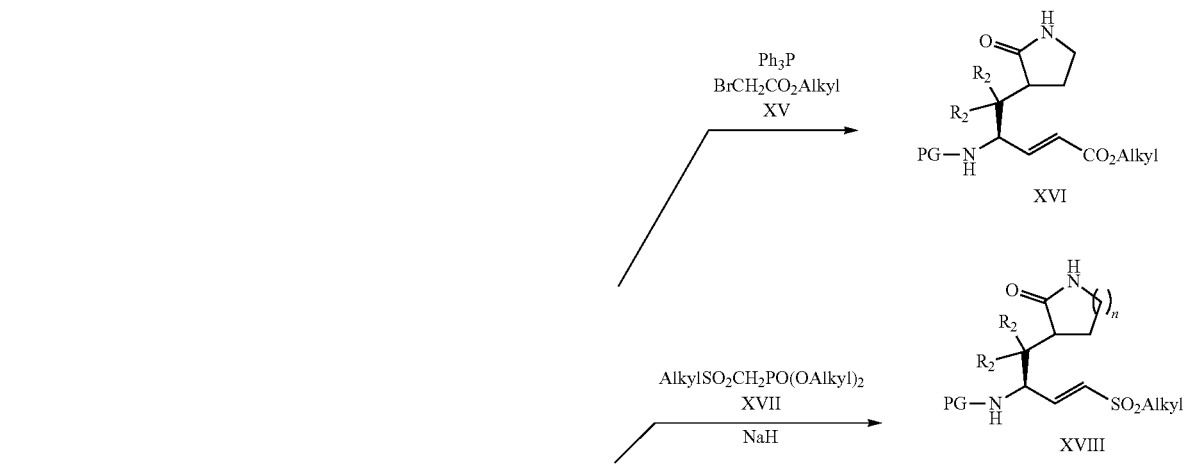
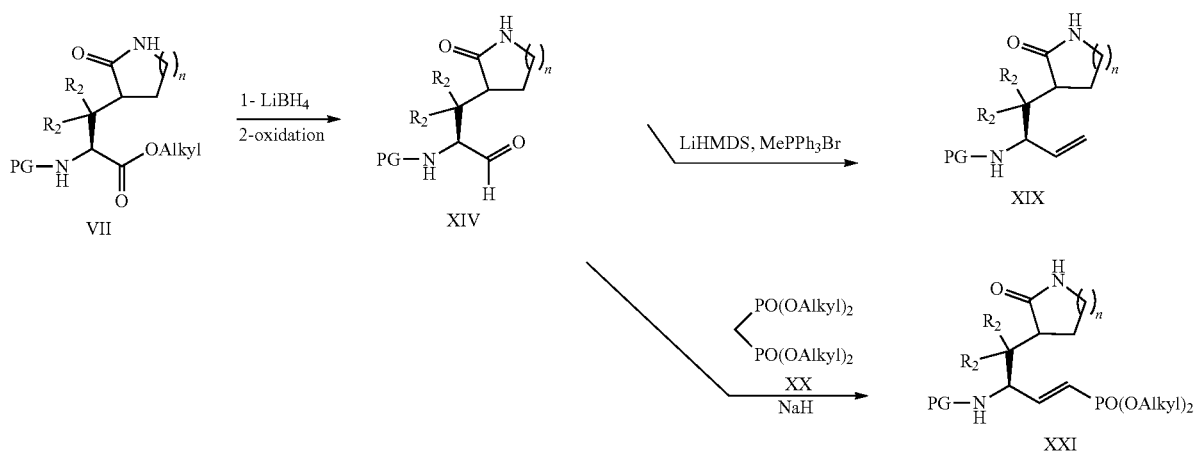

Compounds of formula B-D can be prepared by first deprotection of compound of general formula XVI, XVIII or XXI, for example, in the presence of TFA when Boc was used as a protecting group, and reaction with a carboxylic acid of general formula XII in the presence of peptide coupling reagents like EDC and HOBt.

Scheme 3 A synthetic approach to compounds B-D

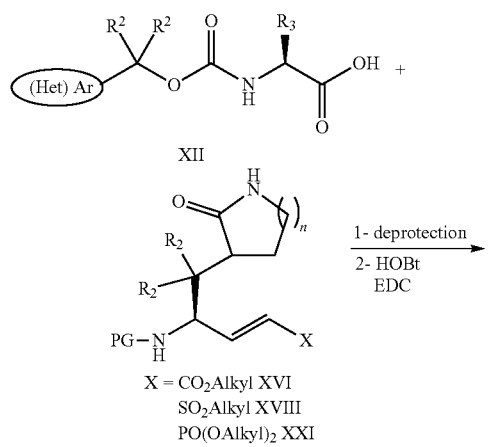

XII

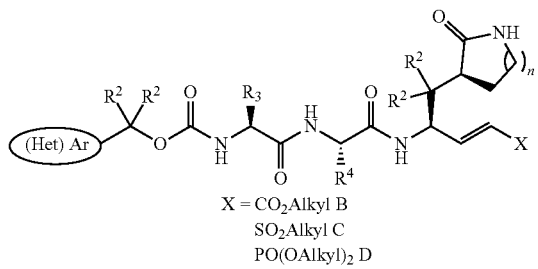

X = $CO_2$Alkyl B
SO$_2$Alkyl C
PO(OAlkyl)$_2$ D

Compounds of formula E can be prepared by first deprotection of compound of general formula XIX, for example, in the presence of TFA when Boc was used as a protecting group; reaction with a carboxylic acid of general formula XII in the presence of peptide coupling reagents like EDC and HOBt and epoxidation using for instance mCPBA.

Scheme 3 A synthetic approach to compounds E

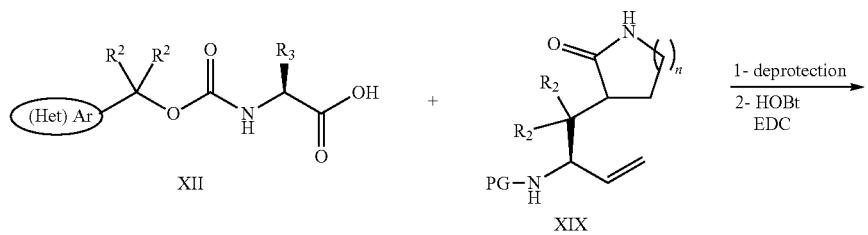

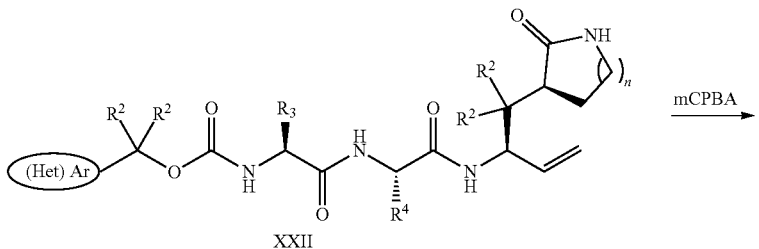

XXII

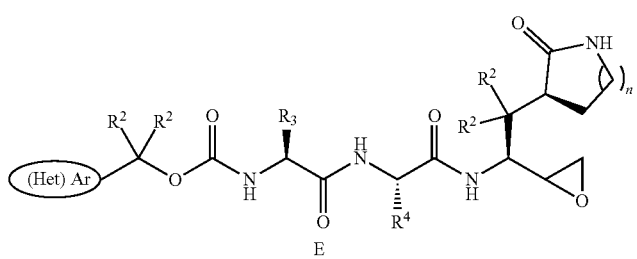

E

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

Anhydrous solvents were purchased from Aldrich Chemical Company, Inc. (Milwaukee, WI) and EMD Chemicals Inc. (Gibbstown, NJ). Reagents were purchased from commercial sources. Unless noted otherwise, the materials used in the examples were obtained from readily available commercial suppliers or synthesized by standard methods known to one skilled in the art of chemical synthesis. $^1$H and $^{13}$C NMR spectra were taken on a Bruker Ascend™ 400 MHz Fourier transform spectrometer at room temperature and reported in ppm downfield from internal tetranmethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Analytic TLC were performed on Sigma-Aldrich® aluminum supported silica gel (25 μm) plates. Column chromatography was carried out on Silica Gel or via reverse-phase high performance liquid chromatography.

Example 1

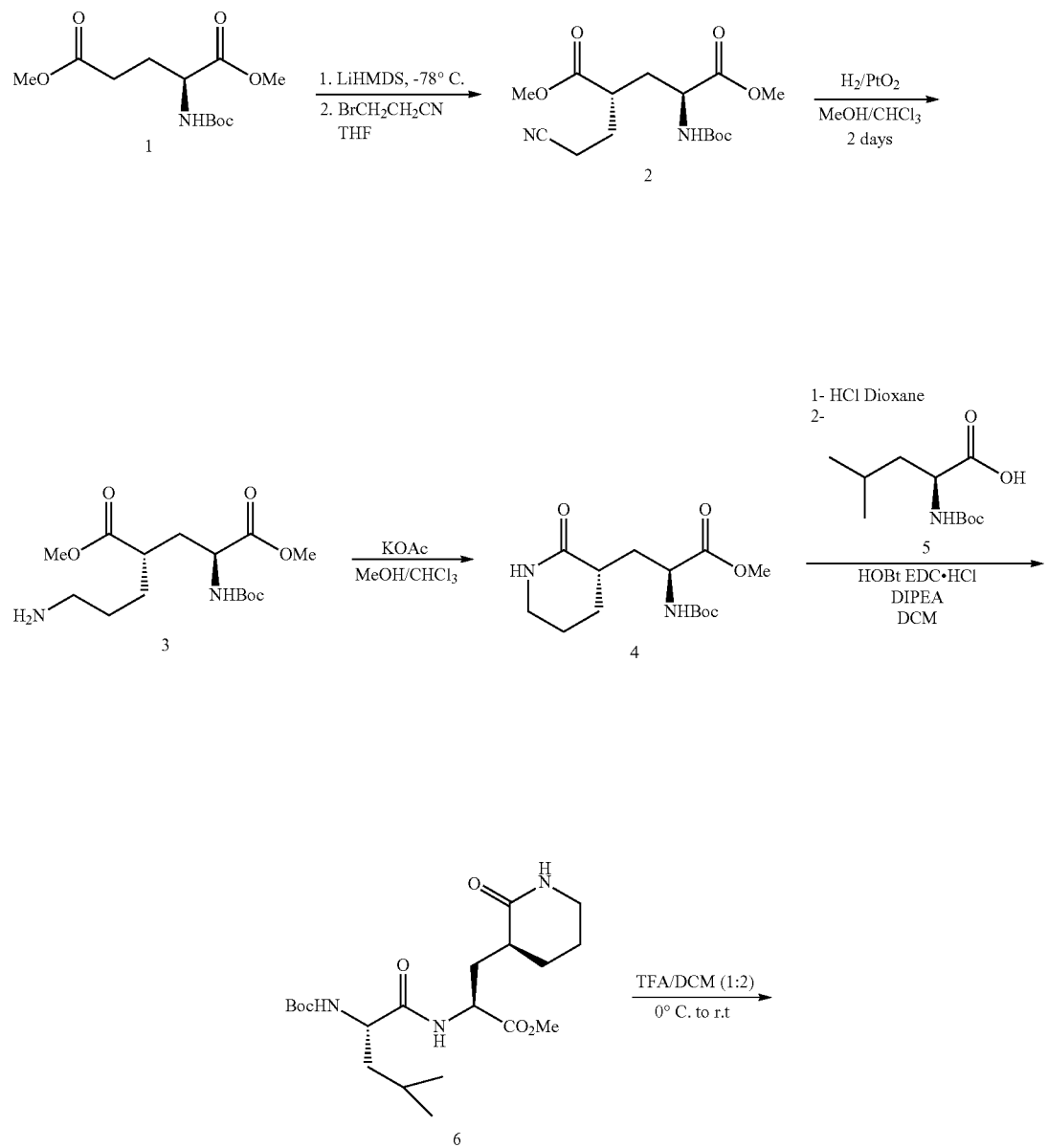

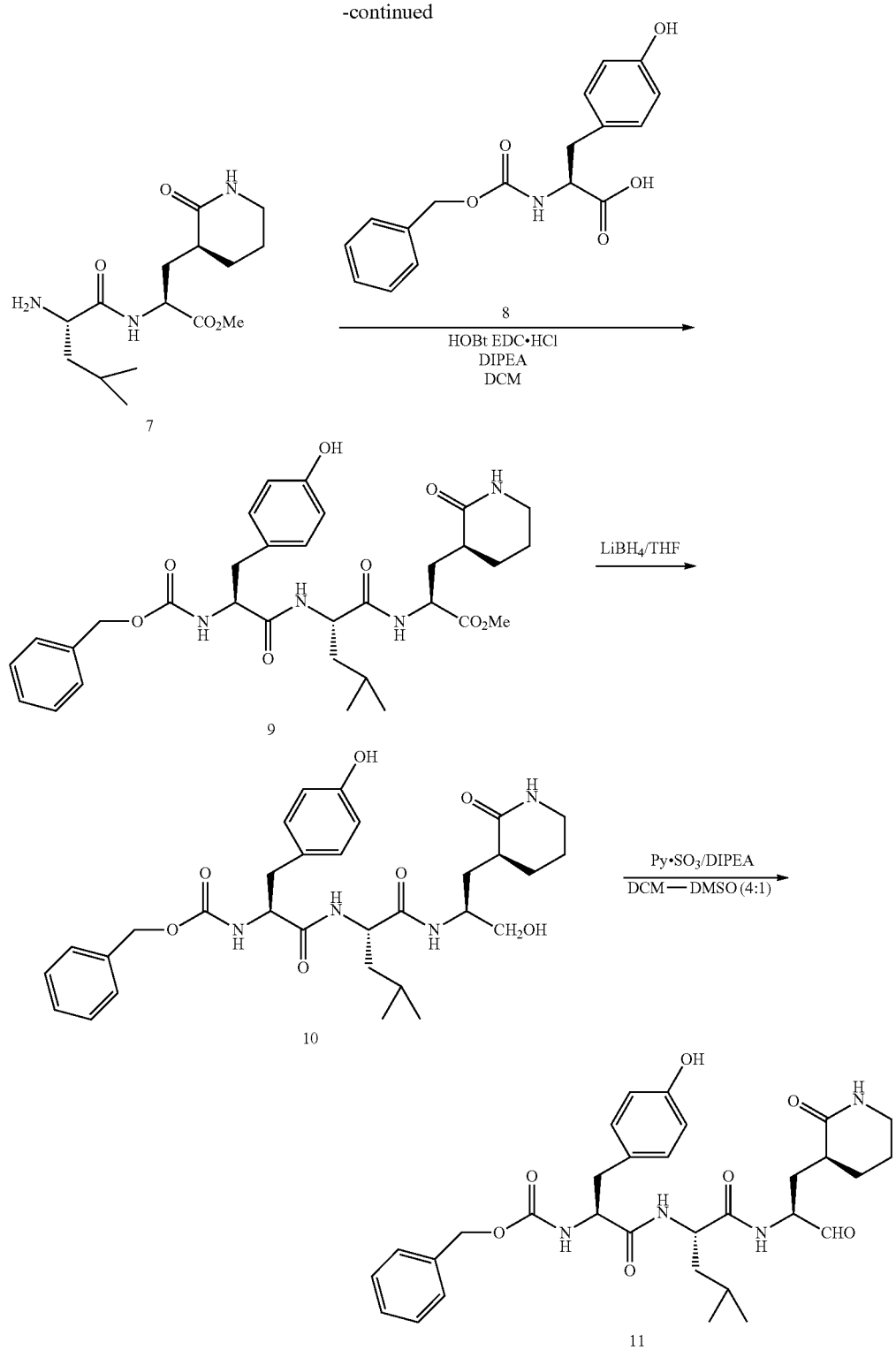

Dimethyl (2S,4S)-2-((tert-butoxycarbonyl)amino)-4-(2-cyanoethyl)pentanedioate (2)

To a solution of N-Boc-L-glutamic acid dimethyl ester (1, 16.5 g, 60.0 mmol) in THF (180 mL) was added dropwise a solution of lithium bis(trimethylsilyl)amide in THF (130 mL, 1 M, 130 mmol) at −78° C. under an argon atmosphere. The resulting mixture was stirred at −78° C. for 1.5 h. At the same time, 3-bromopropionitrile (9.63 g, 71.9 mmol) was added dropwise to the dianion solution over a period of 1 h while maintaining the temperature below −70° C. The reaction mixture was stirred at −78° C. for an additional 3 h. The reaction was quenched with aqueous NH$_4$Cl (80 mL). The reaction mixture was allowed to warm up to room temperature and then EtOAc (140 mL) was added. The layers were separated, and the aqueous layer was extracted with EtOAc (100 mL×2). The combined organic layers were washed with brine, dried over $Na_2SO_4$, and filtered. The filtrate was evaporated to dryness. The crude residue was purified by flash column chromatography (hexanes/ethyl acetate=4/1) to give product 2 (5.25 g, 27%) as a colorless oil. $^1$H NMR ($CDCl_3$, 400 MHz) δ: 5.08 (1H, d, J=8.0 Hz), 4.38 (1H, m), 3.74 (3H, s), 3.71 (3H, s), 2.62-2.65 (1H, m), 2.35-2.42 (2H, m), 1.97-2.04 (4H, m), 1.44 (9H, s). $^{13}$C-NMR ($CDCl_3$, 100 MHz) δ: 15.16, 27.31, 28.26, 34.47, 40.77, 51.55, 52.20, 52.60, 80.37, 118.70, 115.38, 172.36, 174.42. ESI-MS (m/z): 329.4 $(M+H)^+$.

Methyl (S)-2-((tert-butoxycarbonyl)amino)-3-((S)-2-oxopiperidin-3-yl)propanoate (4)

In a hydrogenation flask was placed compound 2 (2.15 g, 6.55 mmol), 5 mL of chloroform and 60 mL of methanol before addition of $PtO_2$ (160 mg, 0.65 mmol). The resulting mixture was mechanically stirred at room temperature for 2 days under hydrogen pressure (50 Psi). The mixture was then filtered over a pad of silica gel. KOAc (1.27 g, 13 mmol) was added to the filtrate and the resulting mixture was stirred at 60° C. for 12 h. After removal of the solvents, the crude residue was purified by silica gel column chromatography (DCM/MeOH=50:1 to 20:1) to give the product 4 as a colorless oil (1.21 g, 62%, over two steps). $^1$H NMR ($CDCl_3$, 400 MHz) δ: 6.41 (1H, s), 5.64 (1H, d, J=8.0 Hz), 4.30-4.36 (1H, m), 3.31-3.33 (1H, m), 2.38-2.42 (1H, m), 2.25-2.34 (1H, m), 2.13-2.16 (1H, m), 1.81-1.93 (3H, m), 1.71-1.79 (1H, m), 1.52-1.61 (1H, m), 1.47 (9H, s). $^{13}$C-NMR ($CDCl_3$, 100 MHz) δ: 21.54, 26.53, 28.29, 34.28, 37.97, 42.35, 51.70, 52.30, 79.81, 155.92, 173.18, 174.58. ESI-MS (m/z): 301.4 $(M+H)^+$.

Methyl (5S, 8S, 11S)-5-(4-hydroxybenzyl)-8-isobutyl-3, 6, 9-trioxo-11-(((S)-2-oxopiperidin-3-yl)methyl)-1-phenyl-2-oxa-4, 7, 10-triazadodecan-12-oate (9)

To a solution of 4 (300 mg, 1.0 mmol) in dioxane was added a solution of 4 M HCl in dioxane. The reaction was stirred for 2 h at room temperature and then concentrated. The crude HCl salt was suspended in DCM (10 mL) and (tert-butoxycarbonyl)-L-leucine (254 mg, 1.1 mmol), 1-hydroxybenzotriazole (169 mg, 1.25 mmol), 1-ethyl-3-(3-dimethylaminopropyl)carbodiimide hydrochloride (240 mg, 1.25 mmol) and N,N-diisopropylethyl amine (0.7 mL, 4.0 mmol) were added at 0° C. The ice bath was removed and the reaction mixture was stirred at room temperature overnight. The reaction mixture was then diluted with EtOAc (100 mL) and washed with 1N HCl, $NaHCO_3$ (5%) and brine, dried over $Na_2SO_4$ and concentrated in vacuo. The residue was purified by flash chromatography (DCM/MeOH 30:1 to 10:1) to give compound 6 (262 mg, 63%). Compound 6 (200 mg, 0.48 mmol) was dissolved in a 1:2 TFA-DCM solution (10 mL) and stirred 2 h at room temperature and then concentrated under vacuum. The crude HCl salt was suspended in DCM (10 mL) and ((benzyloxy)carbonyl)-L-tyrosine 8 (166 mg, 0.53 mmol), 1-hydroxybenzotriazole (82 mg, 0.61 mmol), 1-ethyl-3-(3-dimethylaminopropyl)carbodiimide hydrochloride (161 mg, 0.61 mmol) and N,N-diisopropylethyl amine (0.33 mL, 1.92 mmol) at were added at 0° C. The ice bath was removed and the reaction mixture was stirred at room temperature overnight. The reaction mixture was diluted with EtOAc (100 mL) and washed with 1N HCl, $NaHCO_3$ (5%) and brine. The organic layer was dried over $Na_2SO_4$ and concentrated in vacuo. The residue was purified by flash chromatography (DCM/MeOH 30:1 to 10:1) to give compound 9 (170 mg, 58%). $^1$H NMR (400 MHz, Methanol-$d_4$) δ 7.39-7.20 (m, 5H), 7.12-7.03 (m, 2H), 6.80-6.65 (m, 2H), 5.13-4.94 (m, 2H), 4.64 (s, 1H), 4.54 (dd, J=11.5, 4.2 Hz, 1H), 4.40 (ddd, J=17.8, 9.2, 5.5 Hz, 2H), 3.72 (s, 3H), 3.31-3.20 (m, 2H), 3.05 (dd, J=14.0, 4.9 Hz, 1H), 2.76 (dd, J=14.0, 9.4 Hz, 1H), 2.41 (dt, J=9.9, 5.0 Hz, 1H), 2.30 (ddd, J=15.5, 11.6, 4.1 Hz, 1H), 2.04-1.88 (m, 2H), 1.88-1.80 (m, 1H), 1.79-1.58 (m, 4H), 1.52 (dtt, J=13.3, 10.3, 4.4 Hz, 2H), 0.95 (dd, J=13.9, 6.1 Hz, 6H). $^{13}$C NMR (101 MHz, MeOD) δ 175.04, 173.48, 172.75, 172.45, 156.89, 155.80, 136.77, 130.01, 128.05, 127.22, 114.83, 66.16, 56.45, 51.83, 51.43, 49.83, 41.56, 40.48, 37.32, 36.82, 32.76, 25.52, 24.31, 21.99, 20.85, 20.81. ESI-MS (m/z): 611.4 $(M+H)^+$.

Benzyl ((S)-1-(((S)-1-(((S)-1-hydroxy-3-((S)-2-oxopiperidin-3-yl)propan-2-yl)amino)-4-methyl-1-oxopentan-2-yl)amino)-3-(4-hydroxyphenyl)-1-oxopropan-2-yl)carbamate (10)

To a solution of 9 (120 mg, 0.2 mmol) in THF (3 mL) was added $LiBH_4$ (4M in THF, 0.3 mL, 1.2 mmol) dropwise at 0° C. The reaction mixture was stirred at room temperature for 2 h and then quenched with 1N HCl (15 mL). After being stirred for 1 h at room temperature, the suspension was extracted with ethyl acetate, and washed with $NaHCO_3$ and brine. The organic layers was dried over $Na_2SO_4$, filtered and concentrated in vacuo. The residue was purified by flash chromatography (DCM/MeOH 30:1 to 10:1) to give compound, to afford 10 (83 mg, 73%). $^1$H NMR (400 MHz, Methanol-$d_4$) δ 7.44-7.23 (m, 5H), 7.08 (d, J=8.5 Hz, 2H), 6.71 (d, J=8.5 Hz, 2H), 5.18-4.97 (m, 3H), 4.62 (s, 1H), 4.43-4.28 (m, 2H), 4.09-3.91 (m, 1H), 3.51 (qd, J=11.0, 5.7 Hz, 2H), 3.33 (t, J=1.7 Hz, 1H), 3.06 (dd, J=14.1, 5.0 Hz, 1H), 2.80 (dd, J=14.1, 9.1 Hz, 1H), 2.30 (d, J=9.6 Hz, 1H), 2.16-1.94 (m, 2H), 1.79 (d, J=9.4 Hz, 1H), 1.75-1.56 (m, 5H), 1.56-1.46 (m, 1H), 1.01-0.88 (m, 6H). $^{13}$C NMR (101 MHz, MeOD) δ 176.01, 173.42, 172.89, 157.15, 155.87, 136.70, 129.99, 128.05, 127.62, 127.55, 127.34, 114.88, 66.33, 64.15, 56.75, 52.22, 41.63, 40.51, 37.29, 36.60, 32.74, 25.66, 24.38, 22.11, 20.64, 20.56. EST-MS (m/z): 583.5 $(M+H)^+$.

Benzyl ((S)-3-(4-hydroxyphenyl)-1-(((S)-4-methyl-1-oxo-1-(((S)-1-oxo-3-((S)-2-oxopiperidin-3-yl)propan-2-yl)amino)pentan-2-v)amino)-1-oxopropan-2-yl)carbamate (11)

To a solution of 10 (50 mg, 0.086 mmol) in dichloromethane-DMSO (4:1, 1 mL) were added sulfur trioxide pyridine complex (55 mg, 0.34 mmol) and N,N-diisopropylethyl amine (0.06 mL, 0.34 mmol). The resulting mixture was stirred at room temperature for 12 h and then quenched with 1N HCl (5 mL). The suspension was extracted with ethyl acetate washed with a saturated solution of $NaHCO_3$ and brine. The organic layer was dried over $Na_2SO_4$, filtered and concentrated in vacuo. The residue was purified by preparative TLC (DCM/MeOH=12/1) to give product 11 as a white solid (28 mg, 56%). $^1$H NMR (400 MHz, MeOD) δ 7.39-7.23 (m, 5H), 7.08 (d, J=8.4 Hz, 2H), 6.71 (d, J=8.4 Hz, 2H), 5.01 (dd, J=25.6, 12.8 Hz, 1H), 4.65 (s, 1H), 4.53-4.45 (m, 1H), 4.37 (dd, J=9.5, 4.3 Hz, 2H), 4.01 (d, J=2.8 Hz, 1H), 3.36 (s, 1H), 3.23 (d, J=4.1 Hz, 2H), 3.06 (dd, J=14.1, 4.3 Hz, 1H), 2.77 (dd, J=13.4, 10.4 Hz, 1H), 2.27 (d, J=6.4 Hz, 1H), 2.15 (t, J=13.1 Hz, 1H), 2.01 (dd, J=6.9, 3.5 Hz, 1H), 1.84-1.43 (m, 6H), 1.01-0.87 (m, 6H). $^{13}$C NMR (101 MHz, MeOD) δ 176.10, 173.55, 173.46, 172.89, 172.80, 157.02, 155.82, 136.75, 129.98, 128.05, 127.74, 127.51, 127.25, 114.84, 98.40, 98.32, 66.21, 56.57, 54.07, 53.77, 52.22, 50.72, 50.62, 41.62, 40.66, 40.59, 37.05, 37.02, 36.77, 30.50, 29.93, 25.43, 24.38, 24.32, 21.97, 20.85, 20.52. ESI-MS (m/z): 581.4 $(M+H)^+$.

Example 2
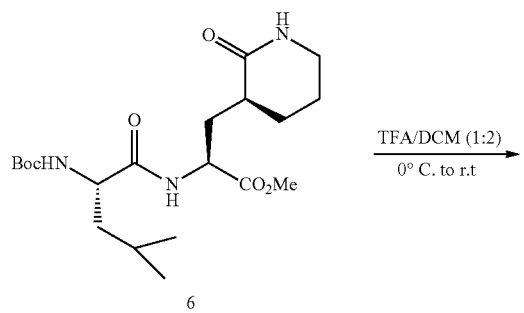
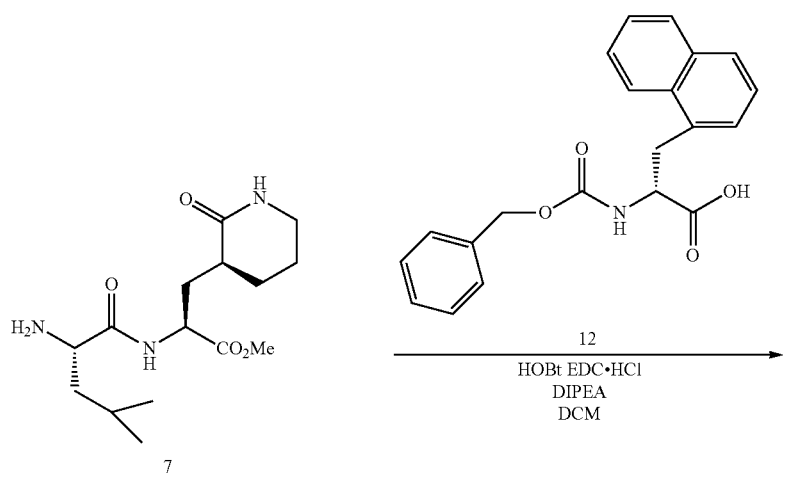
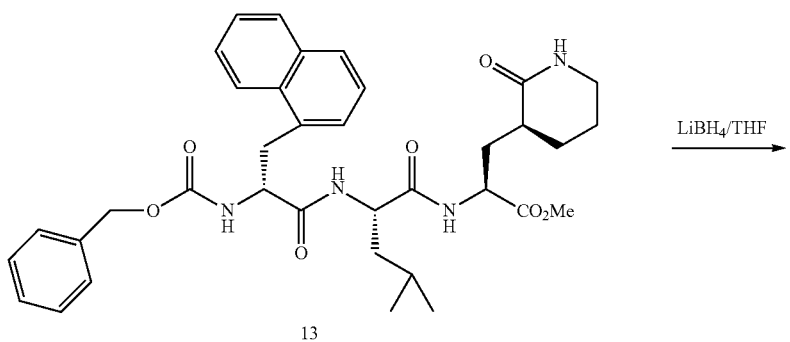
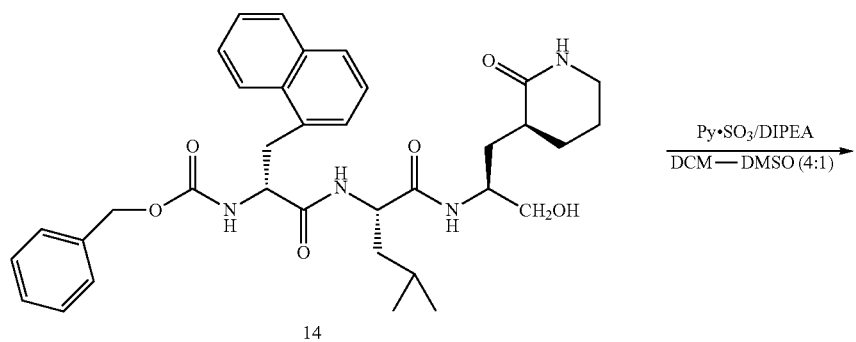

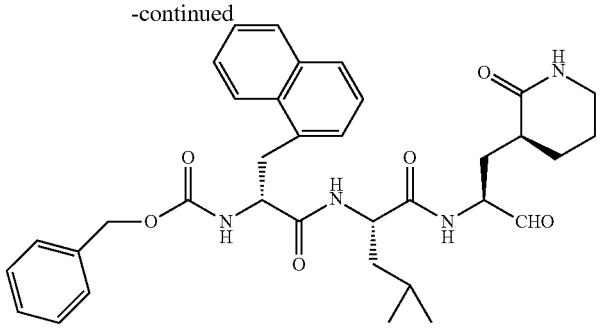

Methyl (5R, 8S, 11S)-8-isobutyl-5-(naphthalen-1-ylmethyl)-3, 6, 9-trioxo-11-(((S)-2-oxopiperidin-3-yl)methyl)-1-phenyl-2-oxa-4, 7, 10-triazadodecan-12-oate (13)

Compound 13 was prepared from (R)-2-(((benzyloxy)carbonyl)amino)-3-(naphthalen-1-yl)propanoic acid using a similar procedure as that used in the synthesis of compound 9. White solid 188 mg (83% yield). $^1$H NMR (400 MHz, MeOD) δ 8.17 (d, J=8.3 Hz, 1H), 7.89 (d, J=8.1 Hz, 1H), 7.79 (d, J=7.4 Hz, 1H), 7.56 (t, J=7.1 Hz, 1H), 7.50 (t, J=7.4 Hz, 1H), 7.44-7.24 (m, 7H), 5.08 (d, J=3.0 Hz, 2H), 4.63 (s, 2H), 4.52 (dd, J=15.4, 6.8 Hz, 3H), 4.21 (dd, J=10.9, 3.8 Hz, 2H), 3.66 (s, 3H), 3.50 (t, J=7.3 Hz, 2H), 3.25-3.16 (m, 2H), 2.50-2.28 (m, 3H), 1.99-1.85 (m, 3H), 1.80 (d, J=13.8 Hz, 2H), 1.69 (d, J=13.5 Hz, 2H), 1.54-1.37 (m, 3H), 1.15 (t, J=11.4 Hz, 1H), 0.99 (dd, J=16.3, 5.6 Hz, 1H), 0.63-0.67 (m, 6H). $^{13}$C NMR (101 MHz, MeOD) δ 175.11, 173.65, 172.72, 172.29, 156.89, 136.72, 134.10, 132.56, 131.94, 128.48, 128.09, 127.63, 127.58, 127.37, 125.99, 125.37, 125.15, 123.33, 66.42, 56.53, 51.56, 51.36, 49.68, 41.51, 39.70, 37.24, 34.36, 32.53, 25.23, 23.64, 22.03, 20.66, 20.20. ESI-MS (m/z): 645.4 (M+H)$^+$.

Benzyl ((R)-1-(((S)-1-(((S)-1-hydroxy-3-((S)-2-oxopiperidin-3-yl))propan-2-yl))amino)-4-methyl-1-oxopentan-2-yl))amino)-3-(naphthalen-1-yl)-1-oxopropan-2-yl))carbamate (14)

Prepared from 13 using a similar procedure as that used in the synthesis of compound 10. White solid 83 mg (75% yield). $^1$H NMR (400 MHz, MeOD) δ 8.13 (d, J=8.4 Hz, 1H), 7.88 (d, J=8.0 Hz, 1H), 7.79 (d, J=7.9 Hz, 1H), 7.65 (d, J=9.2 Hz, 1H), 7.52 (dt, J=14.7, 6.9 Hz, 2H), 7.43-7.26 (m, 6H), 5.12 (dd, J=29.6, 12.4 Hz, 2H), 5.07 (s, 1H), 4.48 (dd, J=9.6, 6.0 Hz, 1H), 4.13 (dd, J=11.4, 3.3 Hz, 1H), 4.02-3.93 (m, 1H), 3.71 (dt, J=12.2, 6.1 Hz, 1H), 3.57-3.37 (m, 5H), 3.19 (t, J=5.8 Hz, 2H), 2.26-2.02 (m, 2H), 1.93 (dd, J=6.7, 3.8 Hz, 1H), 1.77 (dd, J=12.7, 4.6 Hz, 1H), 1.63 (t, J=11.3 Hz, 3H), 1.52-1.36 (m, 3H), 1.13 (d, J=6.1 Hz, 7H), 0.62-0.57 (m, 6H). $^{13}$C NMR (101 MHz, MeOD) δ 176.05, 173.35, 173.26, 156.99, 136.61, 134.11, 132.37, 131.90, 128.53, 128.15, 127.71, 127.67, 127.59, 127.46, 126.08, 125.45, 125.22, 123.32, 68.72, 66.53, 64.10, 56.79, 51.82, 41.58, 39.88, 37.18, 34.07, 32.70, 25.30, 23.46, 22.19, 21.74, 20.26, 20.04. ESI-MS (m/z): 617.4 (M+H)$^+$.

Benzyl ((R)-1-(((S)-4-methyl-1-oxo-1-(((S)-1-oxo-3-((S)-2-oxopiperidin-3-yl)propan-2-yl)amino)pentan-2-yl)amino)-3-(naphthalen-1-yl)-1-oxopropan-2-yl)carbamate (15)

Prepared from compound 14 using a similar procedure as that used in the synthesis of compound 11. White solid 13 mg (41% yield). $^1$H NMR (400 MHz, MeOD) δ 8.22 (d, J=8.1 Hz, 1H), 7.88 (d, J=8.0 Hz, 1H), 7.77 (d, J=7.4 Hz, 1H), 7.51 (tt, J=18.1, 9.0 Hz, 2H), 7.37 (dd, J=14.9, 7.7 Hz, 2H), 7.29 (s, 2H), 7.22 (d, J=7.2 Hz, 2H), 5.05-4.92 (m, 2H), 4.59 (dt, J=21.6, 10.7 Hz, 1H), 4.48 (t, J=3.9 Hz, 1H), 4.43 (dd, J=9.9, 4.6 Hz, 1H), 4.10 (dt, J=19.3, 9.6 Hz, 1H), 4.02 (ddd, J=11.3, 7.7, 3.5 Hz, 1H), 3.73 (dd, J=14.5, 4.4 Hz, 1H), 3.34 (dd, J=18.8, 7.1 Hz, 4H), 3.26-3.11 (m, 3H), 2.28 (s, 1H), 2.17 (t, J=12.4 Hz, 1H), 2.08-1.96 (m, 1H), 1.85-1.44 (m, 8H), 1.47 (d, J=9.7 Hz, 1H), 1.25 (t, J=7.1 Hz, 1H), 1.03-0.85 (m, 6H). $^{13}$C NMR (101 MHz, MeOD) δ 176.08, 173.45, 173.43, 172.71, 172.61, 156.86, 136.69, 134.03, 133.09, 131.99, 128.45, 128.01, 127.53, 127.49, 127.27, 125.86, 125.26, 125.00, 123.28, 98.40, 98.32, 98.25, 66.26, 66.17, 55.83, 55.61, 52.36, 52.28, 52.22, 50.72, 50.54, 41.61, 40.64, 40.57, 40.29, 38.11, 37.08, 37.04, 34.53, 34.36, 30.44, 29.89, 26.44, 25.49, 25.46, 24.44, 24.38, 22.14, 21.92, 21.13, 20.90, 20.56. ESI-MS (m/z): 615.4 (M+H)$^+$.

Example 3

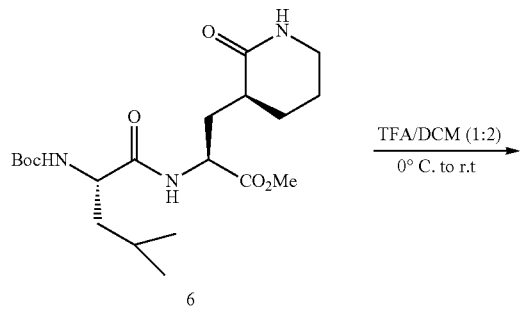

-continued
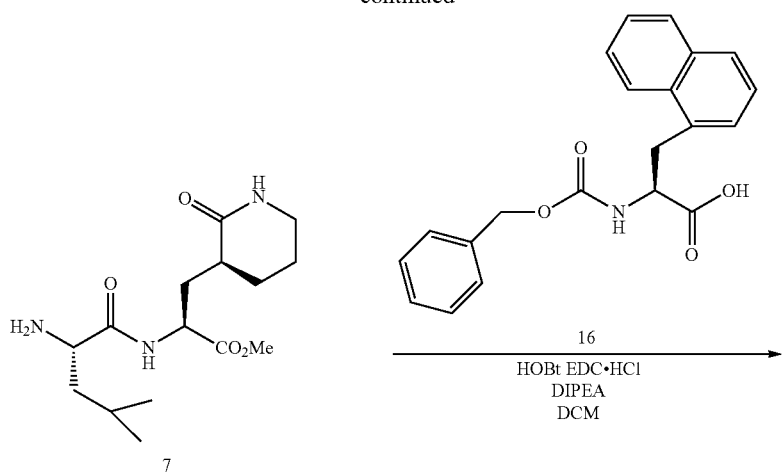
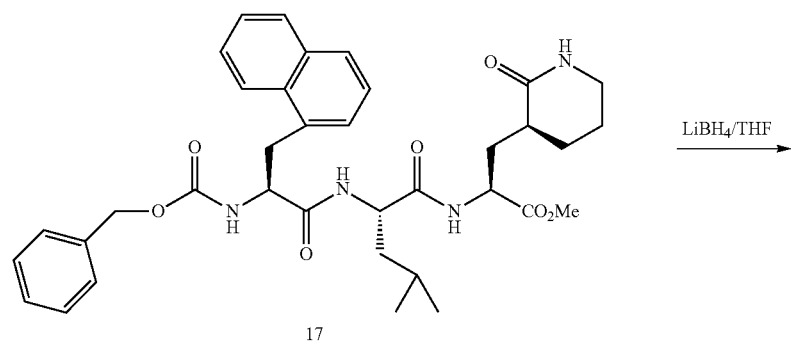
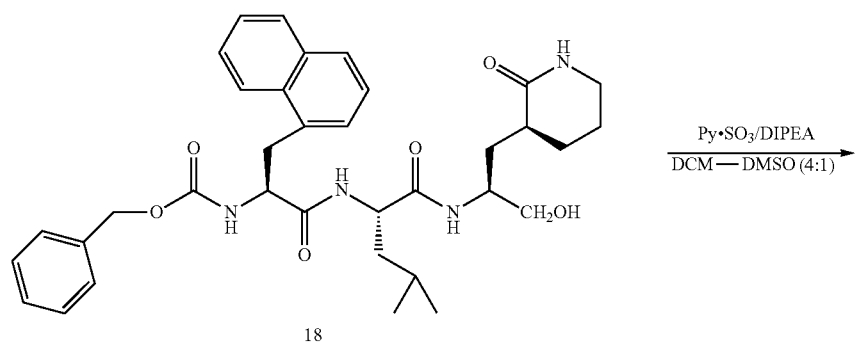
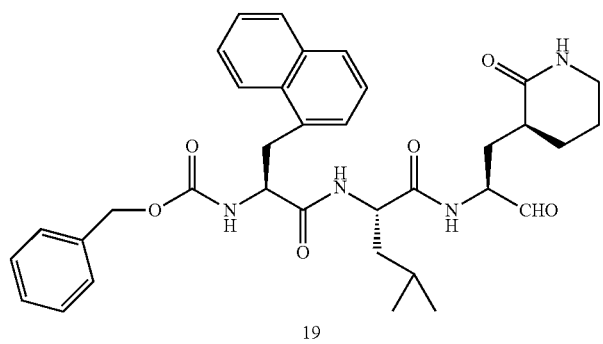

Methyl (5S, 8S, 11S)-8-isobutyl-5-(naphthalen-1-ylmethyl)-3, 6, 9-trioxo-11-(((S)-2-oxopiperidin-3-yl)methyl)-1-phenyl-2-oxa-4, 7, 10-triazadodecan-12-oate (17)

Compound 17 was prepared from (S)-2-(((benzyloxy)carbonyl)amino)-3-(naphthalen-1-yl)propanoic acid 16 using a similar procedure as that used in the synthesis of compound 9. White solid 120 mg (80% yield). $^1$H NMR (400 MHz, MeOD) δ 8.21 (d, J=8.1 Hz, 1H), 7.88 (d, J=7.9 Hz, 1H), 7.77 (d, J=7.1 Hz, 1H), 7.52 (dt, J=20.4, 7.1 Hz, 2H), 7.43-7.34 (m, 2H), 7.30 (d, J=7.1 Hz, 2H), 7.22 (d, J=7.2 Hz, 2H), 5.01 (2H, overlapped with water peak), 4.71-4.59 (m, 2H), 4.54 (dt, J=26.7, 11.3 Hz, 1H), 4.51-4.39 (m, 1H), 3.79-3.67 (m, 4H), 3.32 (t, J=5.8 Hz, 2H), 3.29-3.17 (m, 2H), 2.47-2.38 (m, 1H), 2.35-2.31 (m, 1H), 2.32 (dd, J=18.3, 7.5 Hz, 1H), 2.06-1.96 (m, 1H), 1.95-1.86 (m, 1H), 1.77 (d, 0.1=16.4 Hz, 1H), 1.75-1.65 (m, 2H), 1.66-1.53 (m, 2H), 1.03-0.85 (m, 6H). $^{13}$C NMR (101 MHz, MeOD) δ 175.04, 173.57, 173.48, 172.62, 172.48, 156.80, 136.69, 134.02, 133.05, 132.01, 128.45, 128.03, 127.51, 127.25, 125.86, 125.27, 125.01, 123.29, 66.16, 55.53, 51.98, 51.42, 49.92, 49.82, 41.55, 40.43, 37.33, 34.51, 32.78, 25.54, 24.36, 21.95, 20.87, 20.83. ESI-MS (m/z): 645.5 (M+H)$^+$.

Benzyl ((S)-1-(((S)-4-methyl-1-oxo-1-(((S)-1-oxo-3-((S)-2-oxopiperidin-3-yl)propan-2-yl)amino)pentan-2-yl)amino)-3-(naphthalen-1-yl))-1-oxopropan-2-yl) carbamate (19)

Compound 19 was synthesized from compound 17 using a similar procedure as that used in the synthesis of compound 11. White solid 11 mg (41% yield). $^1$H NMR (400 MHz, MeOD) δ 8.22 (d, J=8.1 Hz, 1H), 7.88 (d, J=8.0 Hz, 1H), 7.77 (d, 0.1=7.4 Hz, 1H), 7.51 (tt, J=18.1, 9.0 Hz, 2H), 7.37 (dd, J=15.0, 7.8 Hz, 2H), 7.27 (d, J=15.0 Hz, 2H), 7.23 (t, J=7.0 Hz, 2H), 4.97 (d, J=9.8 Hz, 2H), 4.60 (dd, J=9.5, 4.4 Hz, 1H), 4.47 (dd, J=10.1, 6.1 Hz, 1H), 4.44-4.35 (m, 1H), 4.02 (ddd, J=11.3, 7.7, 3.5 Hz, 1H), 3.73 (dd, J=14.5, 4.4 Hz, 1H), 3.40-3.32 (m, 3H), 3.26-3.12 (m, 3H), 2.46-2.35 (m, 1H), 2.28 (s, 1H), 2.17 (t, J=12.4 Hz, 1H), 1.84-1.55 (m, 7H), 1.47 (d, J=9.7 Hz, 1H), 1.02-0.83 (m, 6H). $^{13}$C NMR (101 MHz, MeOD) δ 176.08, 173.45, 173.43, 172.71, 172.61, 156.86, 136.69, 134.03, 133.09, 131.99, 128.45, 128.01, 127.53, 127.49, 127.27, 125.86, 125.26, 125.00, 123.28, 98.32, 98.25, 66.26, 66.17, 55.61, 52.36, 52.28, 52.22, 50.72, 50.54, 41.61, 40.64, 40.57, 40.29, 38.11, 37.08, 37.04, 34.53, 34.36, 30.44, 29.89, 26.44, 25.49, 25.46, 24.44, 24.38, 22.14, 21.92, 21.13, 20.90, 20.56. ESI-MS (m/z): 615.5 (M+H)$^+$.

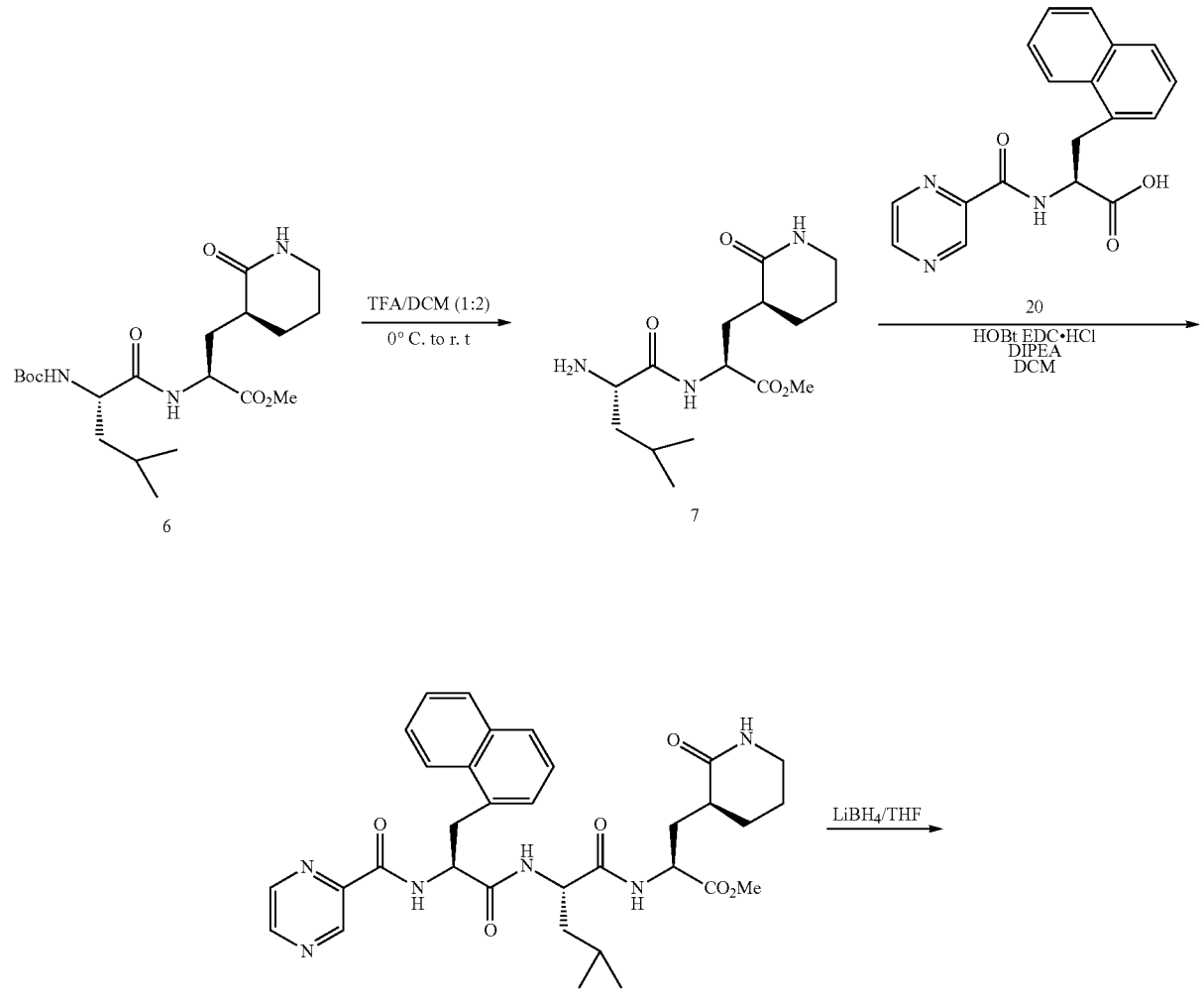

-continued

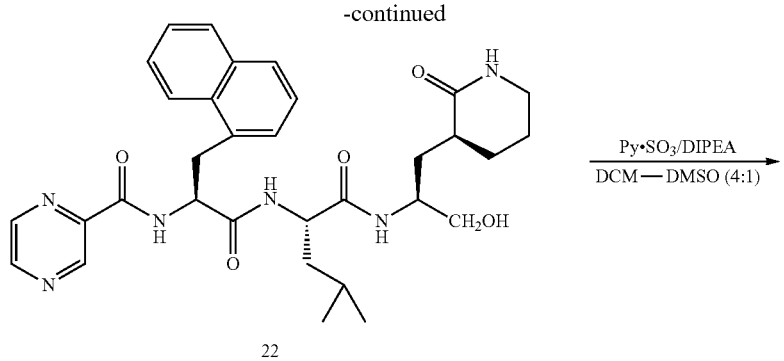

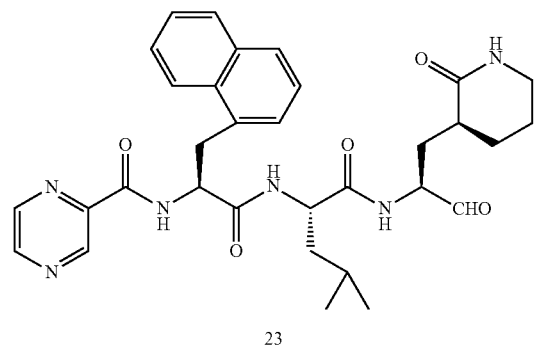

N—((S)-1-(((S)-4-methyl-1l-oxo-1-(((S)-1-oxo-3-((S)-2-oxopiperidin-3-yl)propan-2-yl)amino)pentan-2-yl)amino)-3-(naphthalen-1-yl))-1-oxopropan-2-yl) pyrazine-2-carboxamide Compound 23 was synthesized from compound 6 using a similar procedure as that used in the synthesis of compound 11. $^1$H NMR (400 MHz, Methanol-d4) δ 9.09 (dd, J=16.5, 1.4 Hz, 1H), 8.75 (dd, J=4.9, 2.4 Hz, 1H), 8.63 (td, J=2.5, 1.4 Hz, 1H), 8.30 (d, J=8.5 Hz, 1H), 7.85 (dd, J=8.3, 5.0 Hz, 1H), 7.76 (t, J=7.3 Hz, 1H), 7.60-7.43 (m, 3H), 7.37 (dt, J=9.7, 7.5 Hz, 1H), 5.14-5.00 (m, 1H), 4.59-4.37 (m, 2H), 4.25-4.12 (m, 1H), 4.08-3.99 (m, 1H), 3.89 (ddd, J=19.4, 9.9, 3.8 Hz, 1H), 3.62-3.46 (m, 1H), 3.25 (td, J=9.3, 8.4, 3.7 Hz, 2H), 2.41 (dt, J=10.3, 5.7 Hz, 1H1), 2.31 (d, J=8.8 Hz, 1H1), 2.18 (ddd, J=14.7, 8.8, 3.3 Hz, 1H), 2.04 (tt, J=9.8, 5.0 Hz, 1H), 1.93-1.58 (m, 4H), 1.07-0.82 (m, 6H). ESI-MS (m/z): 587.5 (M+H)+.

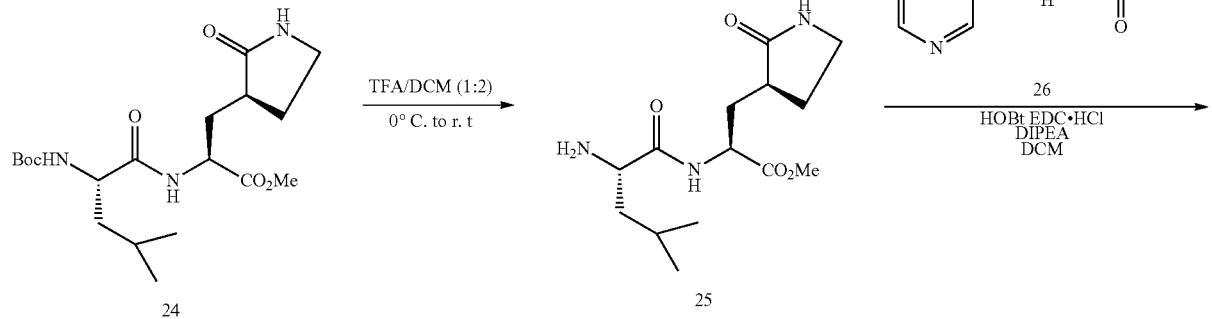

-continued

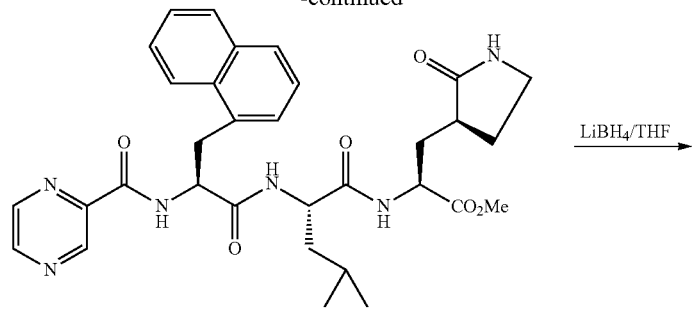

27

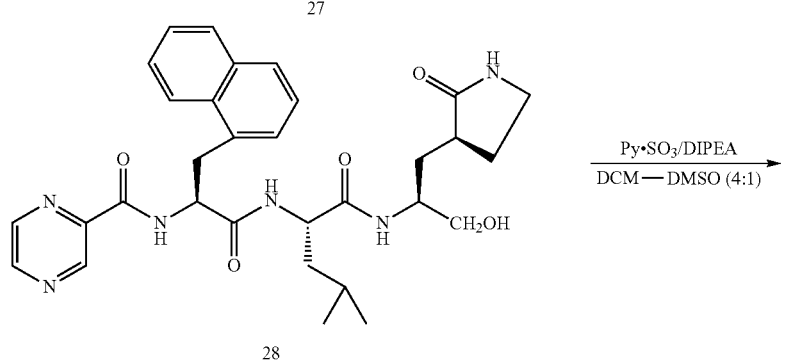

28

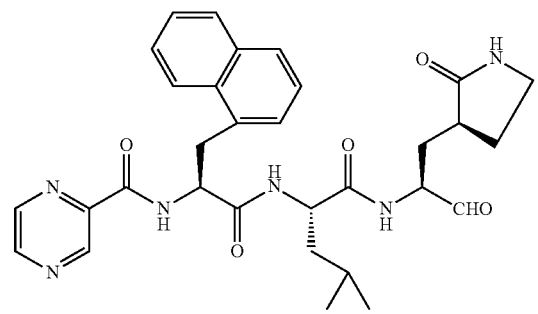

29

N—((S)-1-(((S)-4-methyl-1-oxo-1-(((S)-1-oxo-3-((S)-2-oxopyrrolidin-3-yl))propan-2-yl)amino)pentan-2-yl))amino)-3-(naphthalen-1-yl))-1-oxopropan-2-yl))pyrazine-2-carboxamide (29)

Compound 29 was synthesized from compound 24 using a similar procedure as that used in the synthesis of compound 11. $^1$H NMR (400 MHz, Methanol-$d_4$) δ 9.09 (dd, J=20.6, 1.4 Hz, 1H), 8.75 (dd, J=6.2, 2.5 Hz, 1H), 8.62 (tt, J=2.6, 1.3 Hz, 1H), 8.29 (d, J=8.5 Hz, 1H), 7.85 (t, J=7.8 Hz, 1H), 7.75 (t, J=9.2 Hz, 1H), 7.51 (dq, J=27.0, 7.3 Hz, 3H), 7.37 (dt, J=15.0, 7.6 Hz, 1H), 5.16-4.97 (m, 1H), 4.58-4.36 (m, 2H), 4.09 (dq, J=8.5, 4.3 Hz, 1H), 4.03-3.93 (m, 1H), 3.87 (td, J=15.6, 14.5, 5.2 Hz, 1H), 3.53 (ddd, J=19.6, 14.2, 9.0 Hz, 1H), 2.60-2.43 (m, 1H), 2.41-2.29 (m, 1H), 2.22 (dt, J=14.0, 4.7 Hz, 1H), 2.11-1.98 (m, 1H), 1.89 (q, J=10.7, 9.9 Hz, 1H), 1.83-1.54 (m, 4H), 0.97-0.91 (m, 6H). ESI-MS (m/z): 573.5 (M+H)$^+$.

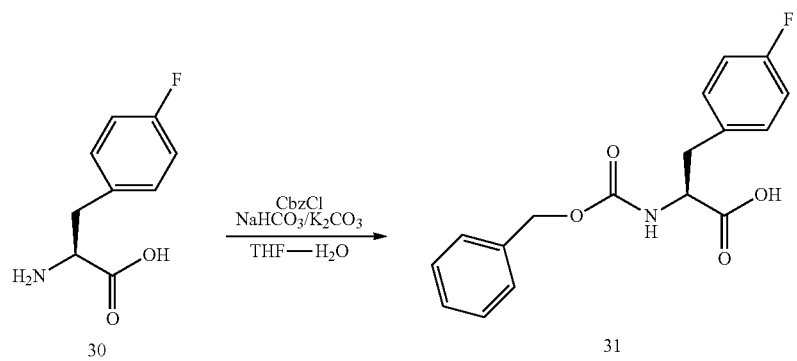

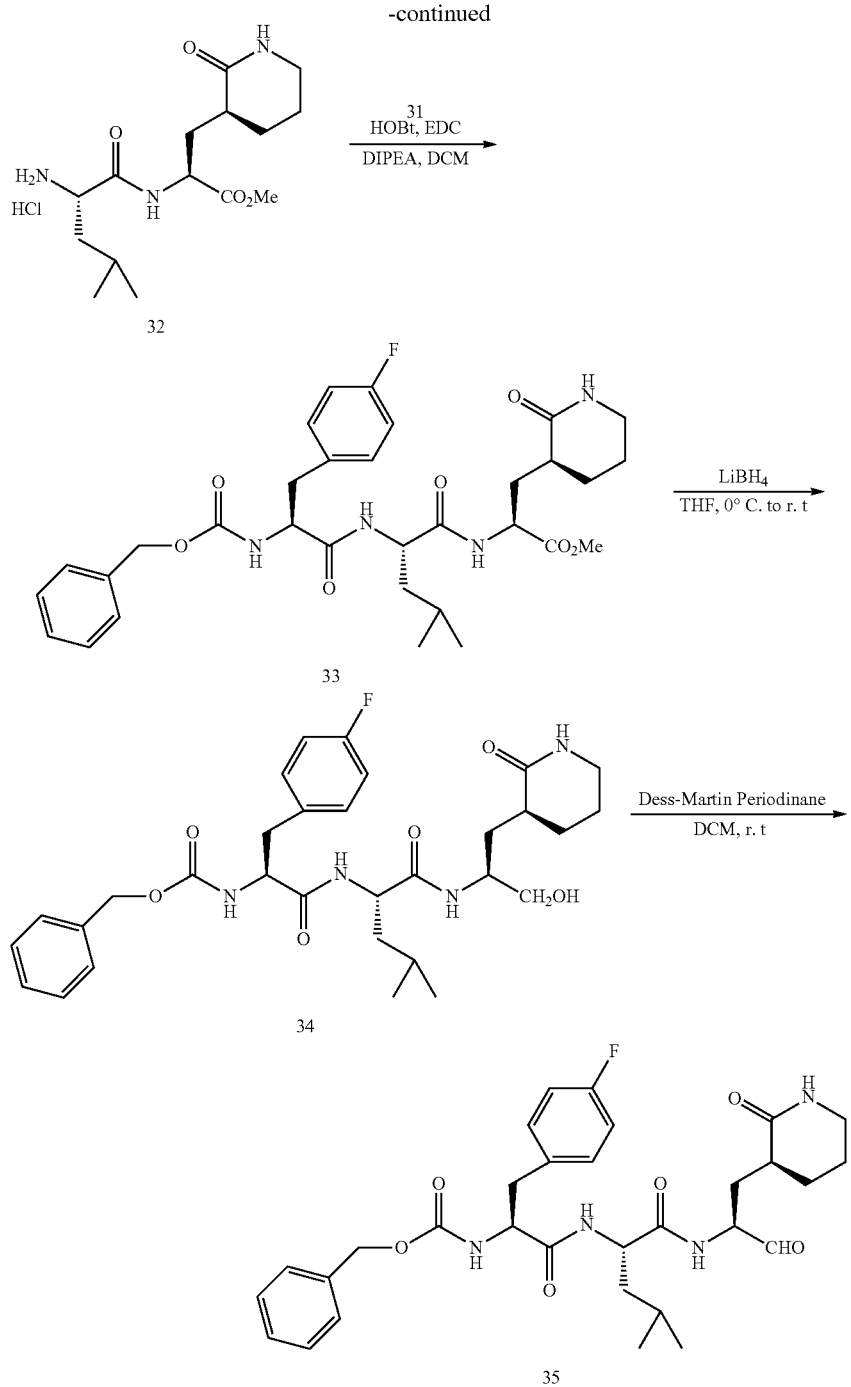

(S)-2-(((Benzyloxy)carbonyl)amino)-3-(4-fluorophenyl)propanoic acid (31)

To a solution of p-fluoro-L-phenylalanine (2.56 g, 13.98 mmol), NaHCO$_3$ (1.76 g, 21 mmol), K$_2$CO$_3$ (2.90 g, 21 mmol) in THF—H$_2$O (v/v=1:1, 50 mL) was added CbzCl (2.2 mL, 15.4 mmol). The reaction mixture was stirred overnight at room temperature. After evaporation of the volatils, the reaction mixture was washed with ethyl acetate (10 mL) and then the pH of the water phase was adjusted to pH=1 by addition of 1N HCl. The water layer was finally extracted with ethyl acetate (30 mL×4) and the combined organic layers dried over Na$_2$SO$_4$, to give, after evaporation, compound 31 (4.2 g, 95%). $^1$H NMR (400 MHz, Methanol-d$_4$) δ 7.37-7.12 (m, 7H), 6.96 (t, J=8.8 Hz, 2H), 5.11-4.93 (m, 2H), 4.47 (dd, J=9.3, 5.0 Hz, 1H), 3.19 (dd, J=14.0, 5.0 Hz, 1H), 2.92 (dd, J=14.0, 9.3 Hz, 1H). $^{13}$C NMR (101 MHz, MeOD) δ 173.61, 163.03, 160.62, 156.94, 136.74, 133.08, 133.05, 130.72, 130.64, 128.08, 127.61, 127.34, 114.78, 114.57, 66.20, 55.37, 36.45. $^{19}$F NMR (377 MHz, Methanol-d$_4$) δ −119.46. LC-MS: m/z [M+H]$^+$ calcd. for C$_{17}$H$_{17}$FNO$_4$: 318.1, found: 318.2.

Methyl (5S,8S,11S)-5-(4-fluorobenzyl)-8-isobutyl-3,6,9-trioxo-11-(((S)-2-oxopiperidin-3-yl)methyl)-1-phenyl-2-oxa-4,7,10-triazadodecan-12-oate (33)

To a solution of compound 32 (230 mg, 0.66 mmol) and amino acid 31 (250 mg, 0.79 mmol) in DCM (6.0 mL) was added 1-hydroxybenzotriazole (135 mg, 1.0 mmol), 1-ethyl-3-(3-dimethylaminopropyl)carbodiimide hydrochloride (190 mg, 1.0 mmol) and N,N-diisopropylethyl amine (0.7 mL, 4.0 mmol) at 0° C. After being stirred at room temperature overnight, the reaction mixture was diluted with EtOAc (50 mL) and washed with 1N HCl, NaHCO$_3$ (5%) and a saturated solution of NaCl. The organic layer was dried over Na$_2$SO$_4$. The solvent was concentrated in vacua and was purified by flash chromatography (DCM/MeOH 20:1) to afford compound 33 (280 mg, 69%). $^1$H NMR (400 MHz, Methanol-d$_4$) δ 8.64 (d, J=8.0 Hz, 1H), 8.19 (d, J=7.5 Hz, 1H), 7.28 (m, 4H), 7.08-6.90 (m, 3H), 5.16-4.94 (m, 2H), 4.42 (ddd, J=8.3, 5.7, 3.1 Hz, 2H), 3.72 (s, 4H), 3.29-3.20 (m, 2H), 3.14 (dd, J=14.0, 4.7 Hz, 1H), 2.82 (dd, J=14.0, 9.7 Hz, 1H), 2.47-2.18 (m, 2H), 2.08-1.78 (m, 2H), 1.73-1.51 (m, J=4H), 0.93 and 0.98 (2s, 6H). $^{13}$C NMR (101 MHz, CD$_3$OD) δ 175.01, 173.60, 173.51, 172.52, 172.45, 172.43, 163.01, 160.59, 156.90, 156.85, 136.79, 133.19, 133.15, 130.77, 130.69, 130.61, 128.03, 127.55, 127.31, 127.28, 114.69, 114.48, 66.16, 66.07, 56.19, 52.00, 51.97, 51.91, 51.87, 51.37, 49.94, 49.84, 41.56, 40.55, 40.51, 37.35, 36.77, 32.83, 32.79, 25.58, 24.34, 21.97, 20.85, 20.82. $^{19}$F NMR (377 MHz, Methanol-d$_4$) δ −119.88−−119.94 (m). LC-MS: m/z [M+H]$^+$ calcd. for C$_{32}$H$_{42}$FN$_4$O$_7$: 613.3, found: 613.5.

Benzyl ((S)-3-(4-fluorophenyl)-1-(((S)-1-(((S)-1-hydroxy-3-((S)-2-oxopiperidin-3-yl)propan-2-yl)amino)-4-methyl-1-oxopentan-2-yl)amino)-1-oxopropan-2-yl)carbamate (34)

To a solution of 33 (230 mg, 0.38 mmol) in THF (2.0 mL) was added LiBH$_4$ (4M in THF, 0.25 mL, 1.0 mmol) dropwise at 0° C. The reaction mixture was stirred at room temperature for 2 h. Then the reaction was quenched with 1N HCl (5 mL) and stirred for 1 h at room temperature. Ethyl acetate (30 mL) was added to the mixture, and the organic layer was washed with 1N HCl, NaHCO$_3$ and brine. The organic layer was dried over Na$_2$SO$_4$, and the filtrate evaporated to dryness. The residue was purified by was purified by flash chromatography (DCM/MeOH 30:1 to 10:1) to afford product 34 (174 mg, 80%). $^1$H NMR (400 MHz, Methanol-d$_4$) δ 7.88 (d, J=8.9 Hz, 1H), 7.38-7.21 (m, 6H), 6.98 (t, J=8.8 Hz, 2H), 5.16-4.96 (m, 2H), 4.39 (dt, J=12.9, 6.2 Hz, 3H), 4.02 (ddd, J=8.9, 5.8, 2.9 Hz, 1H), 3.60-3.42 (m, 2H), 3.25 (t, J=4.7 Hz, 2H), 3.15 (dd, J=14.1, 4.7 Hz, 1H), 2.85 (dd, J=14.1, 9.5 Hz, 1H), 2.31 (d, J=8.7 Hz, 1H), 2.18-1.96 (m, 2H), 1.90-1.77 (m, 1H), 1.72-1.57 (m, 5H), 0.95 (d, J=5.7 Hz, 3H), 0.92 (d, J=5.2 Hz, 3H). $^{13}$C NMR (101 MHz, MeOD) δ 175.98, 173.48, 173.40, 172.53, 163.02, 160.60, 157.06, 136.71, 133.11, 130.75, 130.67, 128.02, 127.56, 127.38, 127.29, 114.72, 114.50, 66.29, 64.16, 56.42, 52.26, 52.22, 41.62, 40.52, 37.29, 36.57, 32.76, 25.71, 24.42, 22.07, 20.62. $^{19}$F NMR (377 MHz, Methanol-d$_4$) δ −119.74−−119.82 (m). LC-MS: m/z [M+H]$^+$ calcd. for C$_{31}$H$_{42}$FN$_4$O$_6$: 585.3, found: 585.5.

Benzyl ((S)-3-(4-fluorophenyl)-1-(((S)-4-methyl-1-oxo-1-(((S)-1-oxo-3-((S)-2-oxopiperidin-3-yl)propan-2-yl)amino)pentan-2-yl)amino)-1-oxopropan-2-yl)carbamate (35)

To a solution of compound 34 (123 mg, 0.21 mmol) in dichloromethane (2.0 mL) was added Dess-Martin periodinane (43 mg, 0.1 mmol). The reaction mixture was stirred at room temperature for 2 h then filtered through a silica gel pad, washed with ethyl acetate. The filtrate was evaporated to dryness and the residue was purified by flash chromatography (DCM/MeOH 30:1 to 12:1) to afford product 35 (70 mg, 57%). $^1$H NMR (400 MHz, Methanol-d$_4$) δ 8.18 (dd, J=7.5, 4.1 Hz, 1H), 7.86 (d, J=9.3 Hz, 1H), 7.42-7.15 (m, 12H), 6.98 (t, J=8.8 Hz, 3H), 5.16-4.95 (m, 3H), 4.41 (qd, J=6.2, 3.8, 3.3 Hz, 3H), 4.02 (ddt, J=9.1, 5.8, 2.7 Hz, 1H), 3.23 (t, J=4.9 Hz, 3H), 3.15 (dd, J=14.1, 4.9 Hz, 2H), 2.83 (dd, J=13.7, 10.0 Hz, 1H), 2.35-2.24 (m, 1H), 2.23-2.11 (m, 2H), 2.02 (dt, J=10.5, 3.5 Hz, 1H), 1.75-1.57 (m, 7H), 0.94 (dd, J=13.6, 6.1 Hz, 10H). $^{13}$C NMR (101 MHz, MeOD) δ 176.05, 173.53, 173.50, 172.51, 172.42, 163.00, 160.59, 156.92, 136.75, 133.17, 130.75, 130.67, 128.04, 128.02, 127.54, 127.35, 127.32, 114.75, 114.71, 114.54, 114.49, 98.39, 98.32, 66.19, 56.26, 54.03, 53.80, 53.73, 52.28, 52.24, 50.80, 50.62, 41.62, 40.71, 40.64, 40.40, 37.07, 37.03, 36.77, 30.45, 29.92, 26.46, 25.50, 25.47, 24.41, 24.35, 22.15, 21.97, 21.94, 21.14, 20.89, 20.85, 20.57, 20.54. $^{19}$F NMR (377 MHz, Chloroform-d) δ −117.12−−117.37 (m). LC-MS: m/z [M+H]$^+$ calcd. for C$_{31}$H$_{40}$FN$_4$O$_6$: 583.3, found: 583.5.

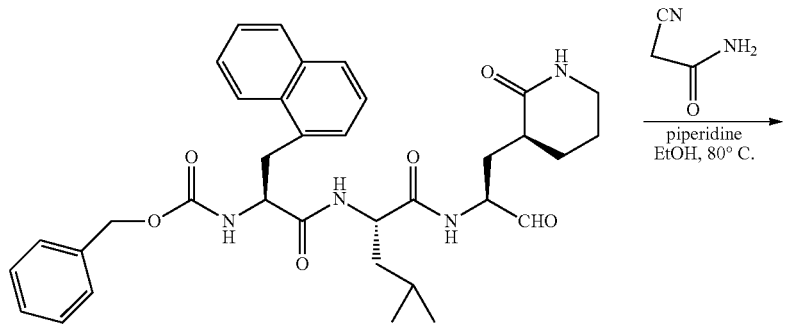

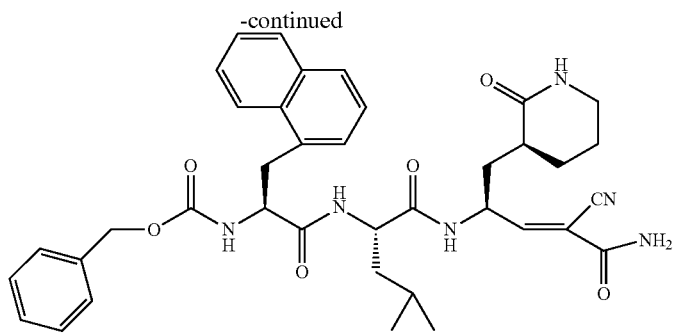

36

Benzyl ((S)-1-(((S)-1-(((S,E)-5-amino-4-cyano-5-oxo-1-((S)-2-oxopiperidin-3-yl)pent-3-en-2-yl)amino)-4-methyl-1-oxopentan-2-yl)amino)-3-(naphthalen-1-yl)-1-oxopropan-2-yl)carbamate (36)

To a solution of 2-cyanoacetamide (6.5 mg, 0.08 mmol) and 19 (50 mg, 0.08 mmol) in ethanol (0.2 mL) was added piperidine (0.66 M in ethanol, 12 µL, 0.008 mmol). The reaction vessel was then placed into a microwave reactor (CEM Discover), and irradiated for 25 minutes at 80° C. After removal of the volatils under vacuo, the reaction mixture was purified by preparative TLC (EtOAc/MeOH 20/1) to give 2-cyano-3-(substituted phenyl)acrylamide product 36 as a white solid (8 mg, 15%). $^1$H NMR (400 MHz, Methanol-d4) δ 8.21 (q, J=12.1, 10.0 Hz, 1H), 7.89 (d, J=8.1 Hz, 1H), 7.84-7.72 (m, 1H), 7.53 (dt, J=22.7, 7.3 Hz, 2H), 7.45-7.36 (m, 1H), 7.36-7.17 (m, 6H), 5.00 (d, J=8.2 Hz, 1H), 4.62 (d, J=10.2 Hz, 1H), 4.45-4.26 (m, 1H), 3.78-3.65 (m, 1H), 3.28-3.16 (m, 4H), 2.50-2.16 (m, 1H), 2.04 (s, 1H), 1.85 (d, J=15.2 Hz, 1H), 1.64 (dd, J=8.4, 4.7 Hz, 1H), 1.06-0.73 (m, 6H). $^{13}$C NMR (101 MHz, CD$_3$OD) δ 175.97, 175.49, 173.37, 172.76, 157.28, 156.97, 136.65, 134.03, 132.99, 131.98, 128.45, 128.03, 128.00, 127.51, 127.31, 127.26, 125.88, 125.27, 125.00, 123.26, 114.64, 113.42, 66.27, 64.16, 55.77, 52.35, 52.19, 41.61, 41.56, 40.09, 37.34, 37.30, 34.30, 24.56, 24.46, 22.06, 20.81, 20.66, 20.51. LC-MS: m/z [M+H]$^+$ calcd. for C$_{38}$H$_{44}$N$_6$O$_6$: 680.3, found: 680.5.

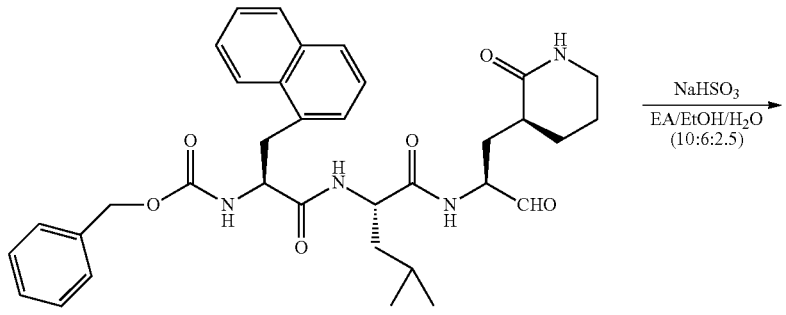

19

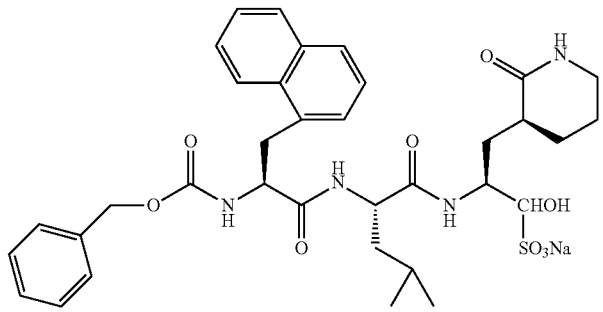

37

Sodium (5S,8S,11S)-12-hydroxy-8-isobutyl-5-(naphthalen-1-ylmethyl)-3,6,9-trioxo-11-(((S)-2-oxopiperidin-3-yl)methyl)-1-phenyl-2-oxa-4,7,10-triazadodecane-12-sulfonate (37)

A solution of 19 (19 mg, 0.03 mmol) and sodium bisulfite (4.5 mg, 0.04 mmol) in a mixture of EtOAc/EtOH/H$_2$O (1:0.6:0.25, 0.2 mL) was stirred for 3 h at 55° C. and then allowed to cool down to room temperature. The precipitate formed was vacuum filtered and the solid was thoroughly washed with absolute ethanol. The filtrate was then dried over anhydrous sodium sulfate, filtered, and concentrated under vacuum to yield a yellowish oil which was treated with ethyl ether to form a white solid. Careful removal of the solvent using a pipette yielded compound 37 (15 mg, 67%). $^1$H NMR (400 MHz, DMSO-d$_6$) δ 8.23 (d, J=8.3 Hz, 2H), 7.92 (dd, J=7.7, 3.6 Hz, 1H), 7.85-7.74 (m, 2H), 7.70-7.49 (m, 2H), 7.30 (dt, J=9.1, 5.6 Hz, 3H), 7.24-7.13 (m, 2H), 4.45 (q, J=10.8, 9.2 Hz, 1H), 4.39-4.18 (m, 1H), 3.87 (d, J=4.8 Hz, 0H), 3.21-2.97 (m, 3H), 2.17 (ddd, J=21.8, 11.5, 4.6 Hz, 1H), 2.01 (d, J=14.7 Hz, 1H), 1.96-1.79 (m, 1H), 1.76-1.63 (m, 2H), 1.57-1.41 (m, 4H), 0.92 (d, J=4.8 Hz, 3H), 0.88 (d, J=4.3 Hz, 3H). $^{13}$C NMR (101 MHz, DMSO-d$_6$) δ 201.42, 173.16, 173.00, 172.94, 171.82, 171.72, 156.25, 137.40, 134.19, 133.83, 132.07, 129.03, 128.72, 128.08, 127.87, 127.75, 127.70, 127.48, 126.52, 126.00, 125.77, 124.19, 65.63, 61.62, 56.05, 55.81, 55.69, 51.70, 41.68, 41.55, 41.40, 34.98, 26.18, 24.66, 23.54, 23.37, 22.27, 22.12, 21.85, 21.77, 15.60. LC-MS: m/z [M+H]$^+$ calcd. for C$_{35}$H$_{45}$N$_4$O$_9$S: 697.3, found: 697.5.

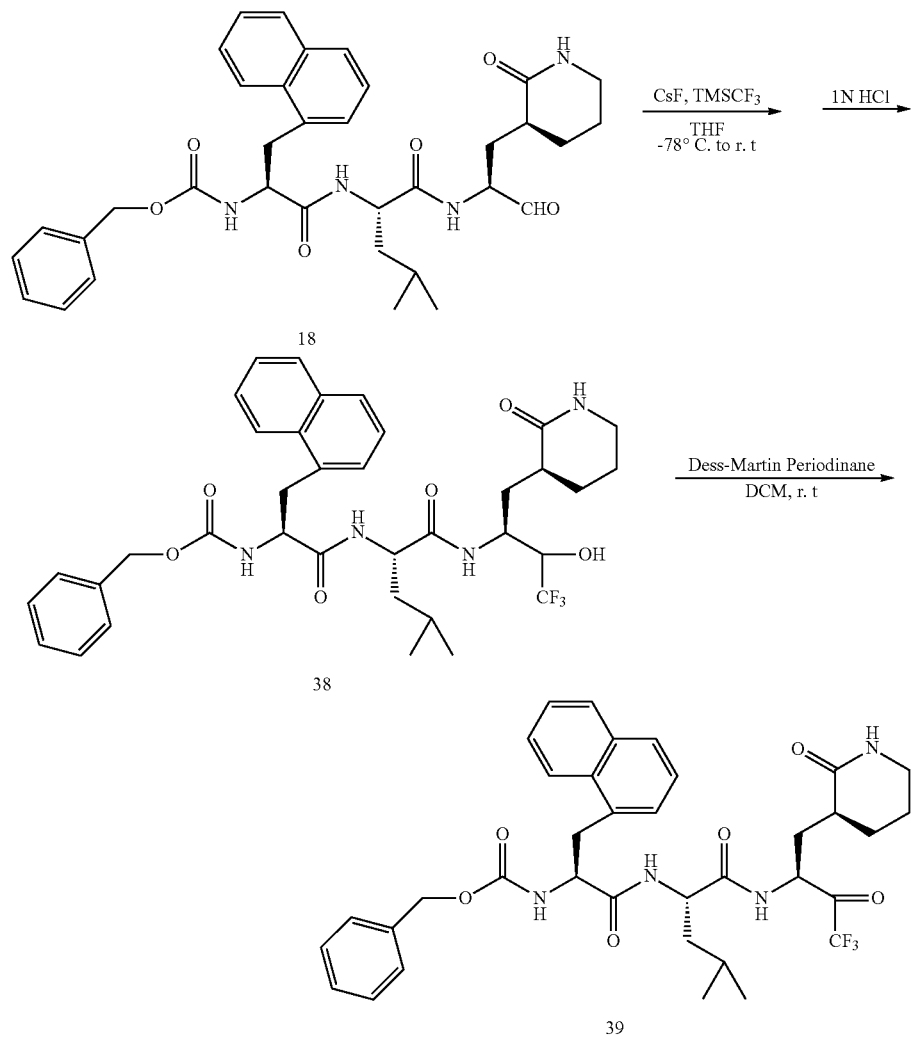

Benzyl ((2S)-1-(((2S)-4-methyl-1-oxo-1-(((2S)-4,4,4-trifluoro-3-hydroxy-1-((S)-2-oxopiperidin-3-yl)butan-2-yl)amino)pentan-2-yl)amino)-3-(naphthalen-1-yl)-1-oxopropan-2-yl)carbamate (38)

To a solution of compound 19 (61 mg, 0.1 mmol) and cesium fluoride in THF (76 mg, 0.5 mmol) was added Me$_3$SiCF$_3$ (2M in THF, 0.1 mL, 0.2 mmol) at −78° C. dropwise over 5 minutes. The reaction mixture was then stirred at room temperature for 2 h and quenched with 1N HCl (0.5 mL). After 1 h, EtOAc (10 mL) was added to the reaction mixture and the organic layer was washed with 1N HCl, NaHCO$_3$ and water. The organic layer was dried over anhydrous sodium sulfate and concentrated under reduced pressure. The residue was purified by preparative TLC (DCM/MeOH 20:1) to provide compound 38 (19 mg, 28%). $^1$H NMR (400 MHz, Chloroform-d) δ 8.21 (s, 1H), 8.08 (s, 1H), 7.98-7.80 (m, 1H), 7.78 (d, J=8.0 Hz, 1H), 7.65-7.45 (m, 1H), 7.36 (d, J=15.8 Hz, 5H), 6.70-6.38 (m, 2H), 5.99 (d, J=33.3 Hz, 1H), 5.66-5.40 (m, 1H), 5.04 (s, 1H), 4.66 (d, J=8.5 Hz, 1H), 4.46 (d, J=8.9 Hz, 1H), 4.33 (t, J=7.4 Hz, 1H), 3.76-3.62 (m, 1H), 3.46-3.36 (m, 1H), 3.24 (s, 2H), 2.22 (s, 1H), 2.10-1.86 (m, 3H), 1.75 (s, 2H), 0.98-0.78 (m, 6H). $^{13}$C NMR (101 MHz, CD$_3$OD) δ 175.83, 174.65, 173.21, 172.79, 172.58, 156.79, 136.72, 134.04, 133.08, 132.87, 131.99, 128.45, 128.03, 128.00, 127.51, 127.36, 127.28, 125.86, 125.26, 125.00, 123.25, 66.22, 55.64, 52.55, 41.68, 41.57, 39.75, 38.56, 37.11, 36.84, 34.59, 26.45, 24.52, 24.42, 22.22, 22.09, 21.54, 20.53, 20.30. $^{19}$F NMR (377 MHz, Chloroform-d) δ −75.94, −77.58. LC-MS: m/z [M+H]$^+$ calcd. for C$_{36}$H$_{44}$F$_3$N$_4$O$_6$: 685.3, found: 685.5.

Benzyl ((S)-1-(((S)-4-methyl-1-oxo-1-(((S)-4,4,4-trifluoro-3-oxo-1-((S)-2-oxopiperidin-3-yl)butan-2-yl)amino)pentan-2-yl)amino)-3-(naphthalen-1-yl)-1-oxopropan-2-yl)carbamate (39)

A solution of compound 38 (19 mg, 0.03 mmol) and Dess-Martin periodinane (45 mg, 0.11 mmol) in dichloromethane (0.8 mL) was stirred at room temperature for 1 h. The reaction mixture was then filtered through silica gel pad, washed with ethyl acetate and concentrated under vacuum. The residue was purified by two successive preparative TLCs (DCM/methanol=20/1 then 100% ethyl acetate) to give compound 39 as a white solid (10 mg, 53%). $^1$H NMR (400 MHz, Methanol-d$_4$) δ 8.22 (d, J=8.5 Hz, 1H), 7.88 (d, J=8.3 Hz, 1H), 7.77 (d, J=7.7 Hz, 1H), 7.52 (dt, J=15.2, 7.6 Hz, 2H), 7.38 (d, J=9.6 Hz, 2H), 7.30 (d, J=6.3 Hz, 3H), 7.21 (d, J=7.2 Hz, 2H), 4.95 (s, 1H), 4.69-4.55 (m, 1H), 4.47 (dd, J=10.2, 6.1 Hz, 1H), 4.38 (d, J=11.6 Hz, 1H), 3.73 (d, J=14.7 Hz, 1H), 3.28-3.16 (m, 2H), 2.40-2.18 (m, 2H), 2.04 (s, 1H), 1.85-1.67 (m, 1H), 1.60 (dt, J=13.3, 7.3 Hz, 2H), 1.44 (d, J=11.1 Hz, 1H), 1.03-0.81 (m, 6H). $^{13}$C NMR (101 MHz, MeOD) δ 176.01, 175.84, 173.66, 173.39, 172.79, 172.66, 156.79, 136.70, 134.03, 133.09, 131.99, 128.45, 128.01, 127.48, 127.30, 127.22, 125.85, 125.25, 125.00, 123.25, 66.13, 66.09, 55.49, 52.29, 52.05, 49.71, 49.43, 41.57, 40.32, 37.00, 36.87, 34.58, 30.12, 29.99, 29.36, 25.62, 25.43, 24.35, 24.32, 22.06, 21.98, 20.76, 20.72, 20.62. $^{19}$F NMR (377 MHz, CD$_3$OD) δ −79.48, −79.97. LC-MS: m/z [M+H]$^+$ calcd. for C$_{36}$H$_{42}$F$_3$N$_4$O$_6$: 683.3, found: 683.5 and 701.5 [M+H$_2$O]$^+$.

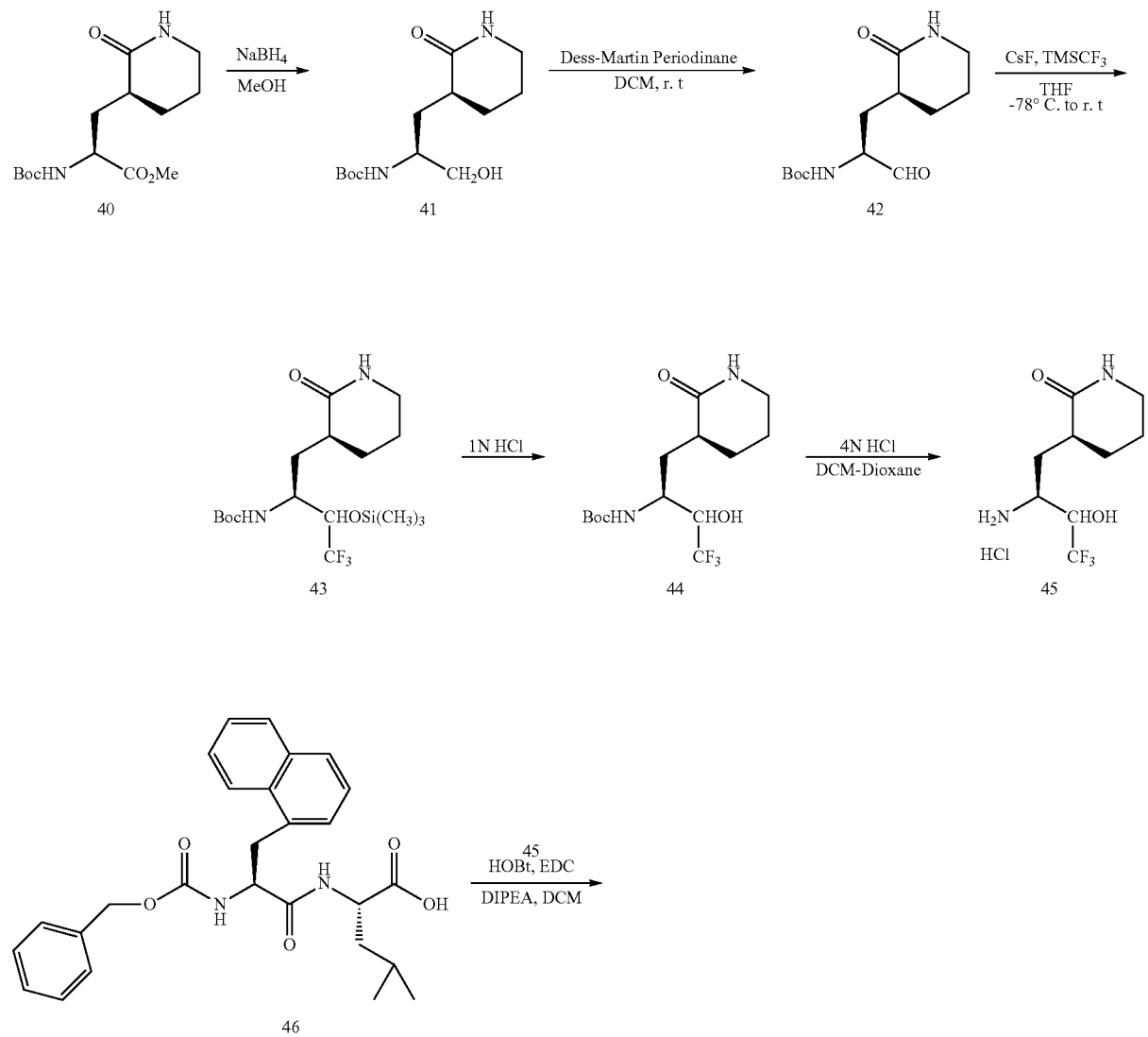

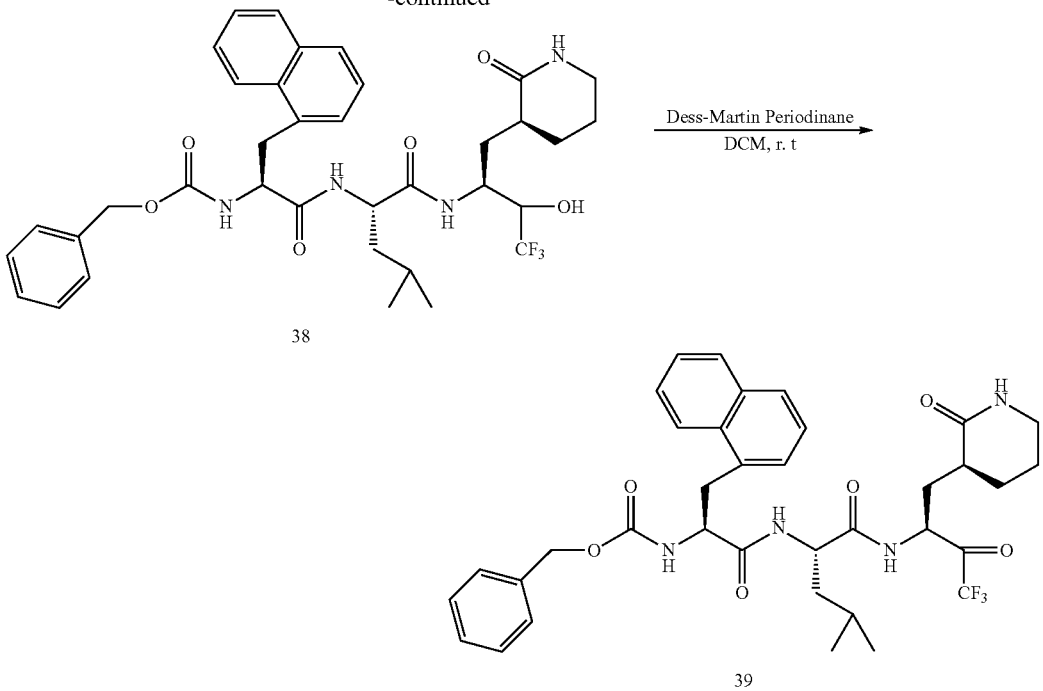

tert-Butyl ((S)-1-hydroxy-3-((S)-2-oxopiperidin-3-yl)propan-2-yl)carbamate (41)

To a solution of compound 40 (600 mg, 2.0 mmol) in MeOH (10 mL) was added NaBH$_4$ (152 mg, 4.0 mmol) at 0° C. The reaction mixture was stirred at room temperature for 3 h then quenched with 1N HCl (5 mL) and finally stirred for 1 h at room temperature. The suspension was extracted with ethyl acetate (3×30 mL), and washed with NaHCO$_3$ and brine. The organic layer was dried over Na$_2$SO$_4$, and then evaporated to dryness. The residue was purified by flash chromatography on silica gel (DCM/MeOH 50:1 to 10:1) to afford compound 41 (480 mg, 88%). $^1$H NMR (400 MHz, Chloroform-d) δ 6.42 (s, 1H), 5.57 (d, J=8.1 Hz, 1H), 3.70 (dt, J=24.3, 5.3 Hz, 2H), 3.63-3.51 (m, 2H), 3.48 (s, OH), 3.32 (qd, J=4.8, 2.2 Hz, 2H), 2.38 (dt, J=11.0, 5.5 Hz, 1H), 2.17 (s, 1H), 2.01-2.1 (m, 1H), 1.96-1.81 (m, 1H), 1.80-1.66 (m, 2H), 1.56 (dtd, J=13.5, 10.5, 3.0 Hz, 1H), 1.44 (s, 9H). $^{13}$C NMR (101 MHz, CDCl$_3$) δ 175.78, 156.55, 79.31, 65.64, 53.43, 50.66, 50.47, 42.45, 38.10, 32.80, 28.39, 26.90, 21.64. LC-MS: m/z [M+H]$^+$ calcd. for C$_{13}$H$_{25}$N$_2$O$_4$: 273.2, found: 273.5.

tert-Butyl ((S)-1-oxo-3-((S)-2-oxopiperidin-3-yl)propan-2-yl)carbamate (42)

A solution of compound 41 (400 mg, 1.47 mmol) and Dess-Martin periodinane (750 mg, 1.77 mmol) in dichloromethane (10 mL) was stirred at room temperature for 2 h. The reaction mixture was filtered through a celite pad and washed with ethyl acetate (50 mL). The organic layer was washed with a solution of sodium thiosulfate (0.4 N, 10 mL) and a solution of NaHCO$_3$ (5%, 10 mL). The organic layer was dried over Na$_2$SO$_4$, and filtered. The filtrate was evaporated under reduced pressure to give the crude product 42 (364 mg, 92%). $^1$H NMR (400 MHz, Chloroform-d) δ 9.55 (s, 1H), 6.33-6.14 (m, 1H), 4.28-4.15 (m, 1H), 3.43-3.20 (m, 4H), 2.47-2.25 (m, 1H), 2.19 (ddd, J=14.2, 8.6, 7.1 Hz, 1H), 1.88 (tt, J=8.5, 4.4 Hz, 2H), 1.75 (dtd, J=13.8, 7.3, 3.3 Hz, 1H), 1.64-1.51 (m, 1H), 1.45 (d, J=12.1 Hz, 9H). $^{13}$C NMR (101 MHz, CDCl$_3$) δ 200.77, 174.84, 156.18, 79.94, 60.40, 58.30, 42.39, 37.34, 31.50, 28.40, 28.32, 27.38, 21.31. LC-MS: m/z [M+H]$^+$ calcd. for C$_{13}$H$_{23}$N$_2$O$_4$: 271.2, found: 271.5.

tert-Butyl ((2S)-4,4,4-trifluoro-3-hydroxy-1-((S)-2-oxopiperidin-3-yl)butan-2-yl)carbamate (44)

To a solution of crude product 42 (270 mg, 1.0 mmol) and CsF (180 mg, 1.18 mmol) in THF (3.0 mL) was added at −78° C., TMSCF$_3$ (2.0M in THF, 0.7 mL, 1.4 mmol) dropwise over 10 minutes. After addition, the reaction mixture was then stirred at room temperature for 1 h, quenched by addition of a 1 N HCl solution (10 mL) and stirred for another 30 minutes. The reaction mixture was extracted with ethyl acetate (30 ml×3), washed with a saturated solution of NaHCO$_3$ and water, dried over Na$_2$SO$_4$, filtered and concentrated under reduced pressure. The residue was purified by flash chromatography on silica gel column (DCM/MeOH 30:1 to 10:1) to afford compound 44. LC-MS: m/z [M+H]$^+$ calcd. for C$_{14}$H$_{24}$F$_3$N$_2$O$_4$: 341.2, found: 341.5.

Benzyl ((2S)-1-(((2S)-4-methyl-1-oxo-1-(((2S)-4,4,4-trifluoro-3-hydroxy-1-((S)-2-oxopiperidin-3-yl)butan-2-yl)amino)pentan-2-yl)amino)-3-(naphthalen-1-yl)-1-oxopropan-2-yl)carbamate (38)

To a solution of crude product 44 (50 mg, 0.18 mmol) in DCM (1.5 mL) was added 4N HCl in dioxane (0.6 mL, 2.4 mmol). The reaction mixture was stirred for 2 h at room temperature and then the volatils were remove under reduced pressure. The residue was dissolved in DCM (1.0 mL) and compound 46 (46 mg, 0.1 mmol), 1-hydroxybenzotriazole (28 mg, 0.2 mmol), 1-ethyl-3-(3-dimethylaminopropyl)carbodiimide hydrochloride (38 mg, 0.2 mmol) and N,N-diisopropylethyl amine (0.14 mL, 0.8 mmol) were added at 0° C. The reaction mixture was stirred at room temperature overnight before being diluted with EtOAc (20 mL). The organic layer was washed with a 1N HCl solution, a solution of NaHCO$_3$ (5%) and brine. The organic layer was dried over Na$_2$SO$_4$. The solvent was evaporated and the residue was purified by flash chromatography on silica gel (DCM/MeOH 30:1 to 15:1) to afford product 38. LC-MS: m/z [M+H]$^+$ calcd. for C$_{36}$H$_{44}$F$_3$N$_4$O$_6$: 685.3, found: 685.5.

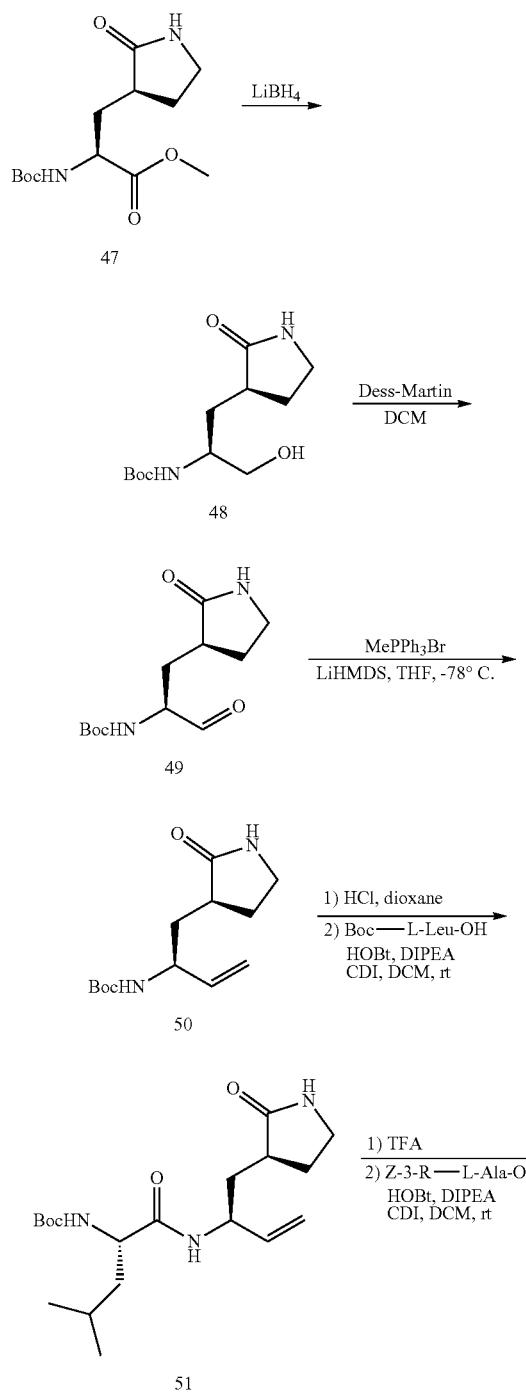

tert-Butyl ((S)-1-oxo-3-((S)-2-oxopyrrolidin-3-yl)propan-2-yl)carbamate (49)

To a solution of compound 4 (1.0 g, 3.49 mmol) in methanol (40 mL) was added NaBH$_4$ (0.53 g, 14 mmol) at room temperature. The reaction mixture was stirred at this temperature for 2 h, then quenched with water (30 mL). The suspension was extracted with EtOAc (50 mL×3) and the combined organic layers were dried over Na$_2$SO$_4$ and finally evaporated under vacuum. The residue was then dissolved in dichloromethane (20 mL) and Dess-Martin periodinane (1.48 g, 3.49 mmol) and NaHCO$_3$ (0.37 g, 3.49 mmol) were added. The resulting mixture was stirred at room temperature for 5 h. The mixture was diluted with EtOAc (150 mL) and the organic layer was washed with an aqueous solution of 10% Na$_2$S$_2$O$_4$, a saturated solution of NaHCO$_3$, a solution of 1N HCl, and brine successively. The organic layer was dried over Na$_2$SO$_4$ and then concentrated to give product 49 as a white solid which was used in the next step without further purification. $^1$H NMR (CDCl$_3$) δ 9.73 (1H, s), 6.02 (1H, br), 5.48 (1H, d, J=7.8 Hz), 4.36-4.25 (1H, m), 3.38-3.32 (2H, m), 2.50-2.44 (2H, m), 2.11-2.03 (1H, m), 1.88-1.76 (2H, m), 1.43 (9H, s). LCMS-ESI (m/z): 257 (M+H)$^+$.

tert-Butyl((S)-1-((S)-2-oxopyrrolidin-3-yl)but-3-en-2-yl)carbamate (50)

To a suspension of methyltriphenylphosphonium bromide (3.29 g, 9.29 mmol) in THF (10 mL) at −78° C. was added LiHMDS (30.3 g, 152 mmol). The resulting yellow suspension was warmed up to room temperature and stirred at the same temperature for 1 hour. After the reaction mixture was cooled down to −78° C., a solution of aldehyde 49 (1.07 g, 4.4 mmol) in THF (5 mL) was added dropwise. The mixture was stirred at 0° C. overnight. The reaction was quenched with MeOH (0.5 mL) and the resulting mixture was poured into 1 N HCl solution (20 mL). Extraction with $Et_2O$ (3×20 mL), drying over $Na_2SO_4$ and evaporation of the solvent in vacuo afforded an orange semi-solid that was purified by silica gel chromatography (DCM/MeOH=20/1) to afford 50 as a white solid (0.36 g, 32%). $^1H$ NMR (400 MHz, Chloroform-d) δ 6.89 (s, 1H), 5.72-5.80 (m, 1H), 5.03-5.20 (m, 3H), 4.14 (s, br, 1H), 3.23-3.31 (m, 2H), 2.40-2.46 (m, 2H), 1.72-1.77 (m, 1H), 1.45-1.52 (m, 1H), 1.40 (s, 9H).

tert-Butyl ((S)-4-methyl-1-oxo-1-(((S)-1-((S)-2-oxopyrrolidin-3-yl)but-3-en-2-yl)amino)pentan-2-yl) carbamate (51)

To a solution of 50 (250 mg, 1.04 mmol) in dioxane (5 mL) was added a solution of 4 M HCl in dioxane (2 mL). The reaction was stirred at room temperature for 3 h and then the volatils were removed under vacuum. The residue was finally coevaporated with toluene the deprotected deprotected product as a colorless oil. To a solution of this amino derivative in DCM (20 mL) was added EDC (250 mg, 1.3 mmol), HOBt (176 mg, 1.3 mmol), Boc-L-Leu-OH (280 mg, 1.2 mmol) and DIPEA (0.84 mL, 4.8 mmol). The solution was stirred at room temperature overnight before being diluted with ethyl acetate (80 mL). The organic layer was washed successively with aq. HCl (1M), sat. aq. $NaHCO_3$ and brine, dried over $Na_2SO_4$. After removal of the volatiles under vacuum, the title compound 51 was obtained as a colorless oil (250 mg, 67%). LCMS-ESI (m/z): 368 $(M+H)^+$.

Benzyl ((S)-1-(((S)-4-methyl-1-oxo-1-(((S)-1-((S)-2-oxopyrrolidin-3-yl)but-3-en-2-yl)amino) pentan-2-yl)amino)-3-(naphthalen-1-yl)-1-oxopropan-2-yl) carbamate (52)

Compound 51 (370 mg, 1.0 mmol) was dissolved in DCM (6 mL) and treated with trifluoroacetic acid (2 mL). The solution was stirred at room temperature for 3 h and the solvent was removed under vacuum. The crude compound was dried under vacuum for 5 h and used in the next step without further purification. To a solution of the deprotected amino acid in DCM (20 mL) was added EDCI (230 mg, 1.2 mmol), HOBt (160 mg, 1.2 mmol), Z-L-Ala(-1-naphthyl)-OH (350 mg, 1.0 mmol) and DIPEA (0.7 mL, 4.0 mmol). After being stirred at room temperature overnight, the reaction mixture was diluted with ethyl acetate (80 mL). The organic layer was washed successively with aq. HCl (1M), sat. aq. $NaHCO_3$ and brine. The organic layer was then dried over $Na_2SO_4$ and the solvent removed under vacuum. The residue was purified by column chromatography (DCM:MeOH=20:1) to give title compound 52 as a white solid (320 mg, 54%). $^1H$ NMR (400 MHz, MeOH-d4) δ 8.18 (t, J=10.1 Hz, 2H), 7.87 (d, J=7.6 Hz, 1H), 7.76 (d, J=7.3 Hz, 1H), 7.48-7.54 (m, 2H), 7.21-7.40 (m, 7H), 5.80-5.85 (m, 1H), 5.21 (dt, $J_1$=1.4 Hz, $J_2$=17.2 Hz, 1H), 5.17 (dt, $J_1$=1.4 Hz, $J_2$=10.4 Hz, 1H), 4.95-4.97 (m, 2H), 4.59-4.65 (m, 1H), 4.40-4.52 (m, 2H), 3.67-3.73 (m, 1H), 3.16-3.28 (m, 2H), 2.47-2.49 (m, 1H), 2.24-2.27 (m, 1H), 1.47-1.77 (m, 4H), 0.91-0.96 (m, 6H); $^{13}C$ NMR (100 MHz, MeOH-d4) δ 181.02, 172.93, 171.58, 156.92, 138.32, 136.69, 134.04, 132.98, 131.98, 128.48, 128.03, 127.52, 127.29, 125.90, 125.30, 125.02, 123.25, 113.62, 66.23, 60.14, 55.81, 52.43, 49.33, 40.68, 40.10, 38.28, 35.58, 34.53, 27.51, 24.40, 21.97, 20.84, 19.49, 13.09; LCMS-ESI (m/z): 599 $(M+H)^+$.

Benzyl ((2S)-1-(((2S)-4-methyl-1-(((1S)-1-(oxiran-2-yl)-2-((S)-2-oxopyrrolidin-3-yl)ethyl)amino)-1-oxopentan-2-yl))amino)-3-(naphthalen-1-yl)-1-oxopropan-2-yl))carbamate To a solution of compound 2 (50 mg, 0.08 mmol) in DCM (5 mL) containing aq. $Na_2HP_3O_4$ (6 M, 40 μL, 0.24 mmol) was added mCPBA (70%, 62 mg, 0.25 mmol). The reaction mixture was stirred at room temperature for 24 h. EtOAc (30 mL) was added and the solution was washed with a saturated solution of $NaHCO_3$, 1 N HCl, brine, and dried over $Na_2SO_4$. After concentration under vacuum, the residue was purified on preparative TLC to afford compound 53 as a white solid (20 mg, 39%). $^1H$ NMR (400 MHz, MeOH-d4) δ 8.11-8.23 (m, 1H), 7.94-8.01 (m, 1H), 7.89 (d, J=7.7 Hz, 1H), 7.78 (d, J=7.2 Hz, 1H), 7.23-7.61 (m, 8H), 4.98 (s, 2H), 4.59-4.62 (m, 1H), 4.35-4.40 (m, 1H), 4.02-4.10 (m, 1H), 3.69-3.74 (m, 1H), 3.21-3.28 (m, 2H), 3.04-3.07 (m, 1H), 2.75-2.77 (m, 1H), 2.58-2.60 (m, 1H), 2.45-2.52 (m, 1H), 2.09-2.33 (m, 2H), 1.53-1.81 (m, 4H), 1.30-1.37 (m, 1H), 0.88-0.98 (m, 6H); $^{13}C$ NMR (100 MHz, MeOH-d4) δ 180.88, 173.64, 173.56, 172.75, 156.87, 136.69, 134.03, 133.00, 132.19, 131.98, 129.67, 128.44, 128.01, 127.50, 127.26, 127.20, 125.87, 125.28, 124.99, 123.24, 66.20, 55.57, 53.29, 52.40, 44.06, 40.51, 40.06, 38.05, 34.38, 32.54, 27.43, 24.50, 21.95, 20.66; LCMS-ESI (m/z): 615 $(M+H)^+$, 633 $(M+H+H_2O)^+$

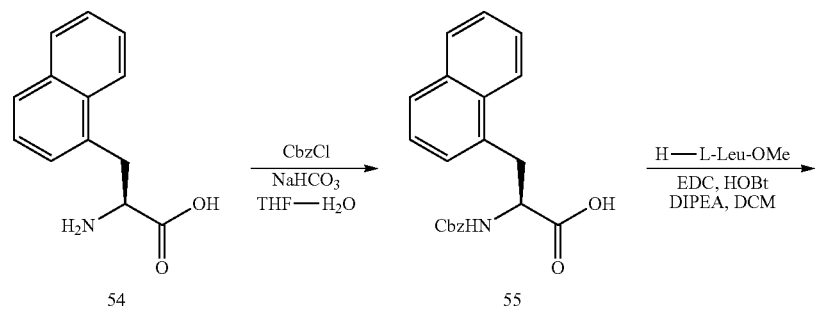

-continued
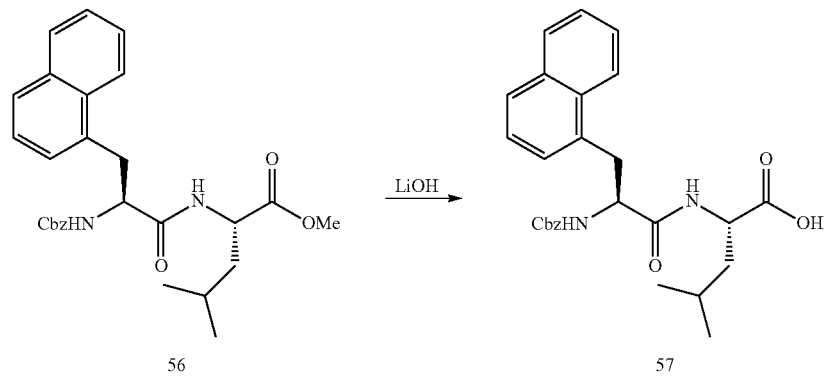
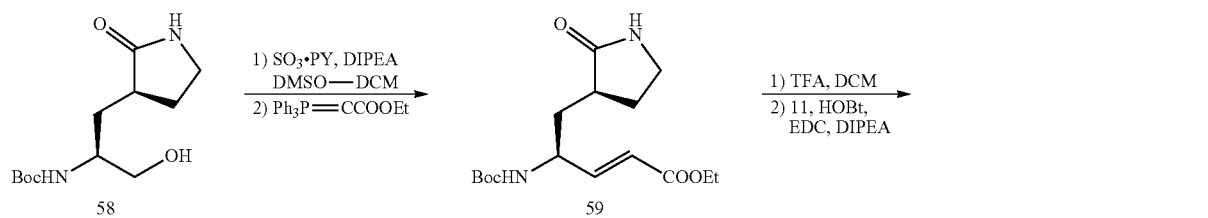
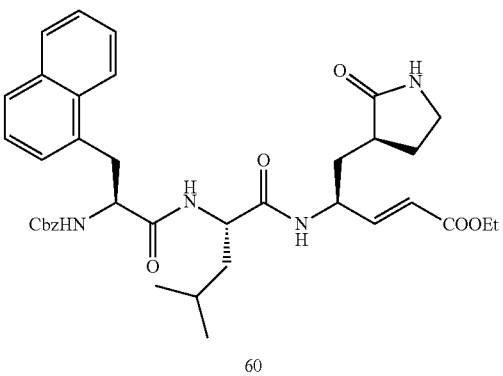
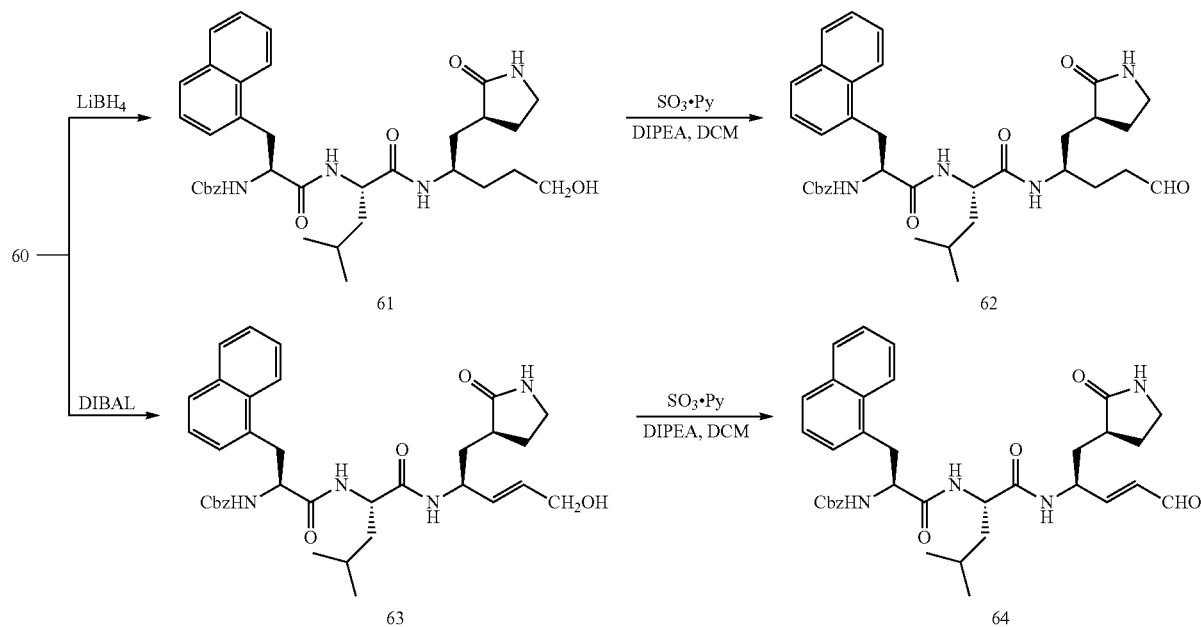

Methyl ((S)-2-(((benzyloxy)carbonyl)amino)-3-(naphthalen-1-yl)propanoyl)-L-leucinate (56)

To a solution of Cbz-L-Ala(1-Naphthyl)-OH 55 (0.78 g, 2.25 mmol) and L-Leu-OMe (0.45 g, 2.48 mmol) in DCM (50 mL) was added EDCI (560 mg, 2.9 mmol), HOBt (400 mg, 2.9 mmol), and DIPEA (1.6 mL, 9 mmol). The reaction mixture was stirred overnight at room temperature at which time $H_2O$ (100 mL) and EtOAc (200 mL) were added. The organic layer was washed successively with aq. HCl (1 M, 50 mL), sat. aq. $NaHCO_3$ (200 mL) and brine (100 mL), and then dried over $Na_2SO_4$. The solvent was removed under vacuum to give the title compound as a yellow solid after crystallization from ethyl acetate (0.9 g, 85%). $^1$H NMR (400 MHz, MeOH-d4) δ 7.89 (d, J=9.0 Hz, 1H), 7.79 (d, J=8.0 Hz, 1H), 7.49-7.58 (m, 2H), 7.36-7.41 (m, 8H), 5.82 (d, J=8.0 Hz, 1H), 5.51-5.53 (m, 1H), 5.08-5.16 (m, 2 H), 4.60-4.65 (m, 1H), 4.44-4.59 (m, 1H), 4.09-4.23 (m, 2H), 3.21-3.27 (m, 2H), 2.48-2.52 (m, 1H), 1.57-1.80 (m, 4H), 1.21-1.40 (m, LCMS-ESI (m/z): 477 (M+H)$^+$.

((S)-2-(((Benzyloxy)carbonyl)amino)-3-(naphthalen-1-yl)propanoyl)-L-leucine (57)

To a solution of methyl ester 56 (2.0 g, 4.2 mmol) in MeOH (19 mL) was added a solution of LiOH $H_2O$ (270 mg, 6.3 mmol) in $H_2O$ (1 mL). The reaction mixture was stirred overnight at room temperature. The volatiles were removed under vacuum to give a colourless residue that was partitioned between EtOAc and aq. HCl (1M). The organic layer was separated, washed successively with aq. HCl (1M) and brine, then dried over $MgSO_4$, and the solvent removed under vacuum to give a glassy solid. Recrystallization from EtOAc gave the title compound 57 as a white solid (1.86 g, 96%). $^1$H NMR (400 MHz, Methanol-d$_4$) δ 8.13-8.21 (m, 1H), 7.89 (s, br, 1H), 7.79 (s, 1H), 7.25-7.57 (m, 9H), 5.02-5.17 (m, 1H), 4.33-4.59 (m, 1H), 3.34-3.56 (m, 1H), 1.34-1.54 (m, 3H), 0.84-0.88 (m, 6H); LCMS-ESI (m/z): 463 (M+H)$^+$.

Methyl (5S,8S,11S,E)-8-isobutyl-5-(naphthalen-1-ylmethyl)-3,6,9-trioxo-11-(((S)-2-oxopyrrolidin-3-yl)methyl)-1-phenyl-2-oxa-4,7,10-triazatetradec-12-en-14-oate (60)

To a solution of compound 59 (330 mg, 1.0 mmol) in dioxane (5 ML) was added HCl (4 M in dioxane, 2 mL). The reaction was stirred at room temperature for 3 h and then the volatils were removed under vacuum to give the crude deprotected amine which was used directly in the next step. This compound was thus dissolved in DCM (20 mL) and EDC (250 mg, 1.3 mmol), HOBt (176 mg, 1.3 mmol), dipeptide 57 (460 mg, 1.0 mmol) and DIPEA (0.84 mL, 4.8 mmol) were added. The solution was stirred at room temperature overnight and then diluted with ethyl acetate (80 mL). The organic layer was washed successively with aq. HCl (1M), sat. aq. $NaHCO_3$ and brine, dried over $Na_2SO_4$ and the solvent removed under vacuum. The residue was purified by column chromatography to give 60 as a white solid (460 mg, 70%). $^1$H NMR (400 MHz, Methanol-d$_4$) δ 8.18-8.21 (m, 1H), 7.74-7.94 (m, 3H), 7.23-7.68 (m, 8H), 6.91 (dd, J=15.5, 5.3 Hz, 1H), 5.90-6.02 (m, 1H), 4.95-5.01 (m, 1H), 4.60-4.65 (m, 1H), 4.32-4.86 (m, 1H), 4.01-4.23 (m, 2H), 3.70-3.75 (m, 1H), 3.21-3.27 (m, 2H), 2.48-2.52 (m, 1H), 2.40-2.66 (m, 1H), 1.58-1.80 (m, 4H), 1.20-1.40 (m, 6H), 0.89-1.10 (m, 6H); LCMS-ESI (m/z): 657 (M+H)$^+$.

Benzyl ((S)-1-(((S)-1-(((R)-5-hydroxy-1-((S)-2-oxopyrrolidin-3-yl)pentan-2-yl)amino)-4-methyl-1-oxopentan-2-yl)amino)-3-(naphthalen-1-yl)-1-oxopropan-2-yl)carbamate (61)

To a solution of methyl ester 60 (34 mg, 0.05 mmol) in dry THF (3 mL) was added LiBH$_4$ (2M in THF, 0.03 mL, 0.06 mmol) at 0° C. The resulting mixture was stirred at room temperature for 3 h and then quenched with aq. HCl (1M). Ethyl acetate (20 ML) was added and the organic layer was further washed with $H_2O$, dried over $Na_2SO_4$, and the solvent removed under vacuum to give a white solid. Recrystallization from EtOAc gave 61 as a white solid (9 mg, 29%). $^1$H NMR (400 MHz, Methanol-d$_4$) δ 8.21 (d, J=8.3 Hz, 1H), 7.97-7.71 (m, 3H), 7.52 (dt, J=14.6, 7.5 Hz, 2H), 7.45-7.20 (m, 9H), 5.10-4.94 (m, 2H), 4.58 (dd, J=9.5, 5.3 Hz, 1H), 4.46-4.29 (m, 1H), 4.12 (q, J=7.1 Hz, 2H), 3.97 (d, J=10.6 Hz, 1H), 3.70 (dd, J=14.0, 5.0 Hz, 1H), 3.30-3.17 (m, 2H), 2.59-2.20 (m, 5H), 2.05-1.38 (m, 7H), 1.37-1.16 (m, 4H), 0.93 (td, J=12.7, 10.8, 5.7 Hz, 6H); LCMS-ESI (m/z): 631 (M+H)$^+$.

Benzyl ((S)-1-(((S)-4-methyl-1-oxo-1-(((R)-5-oxo-1-((S)-2-oxopyrrolidin-3-yl)pentan-2-yl)amino) pentan-2-yl)amino)-3-(naphthalen-1-yl)-1-oxopropan-2-yl)carbamate (62)

To a solution of j (47 mg, 0.075 mmol) in DCM (4 mL) and DMSO (1 mL) was added DIPEA (50 µL, 0.3 mmol) at 0° C. The solution was stirred for 30 min before addition of $SO_3$ pyridine complex (47 mg, 0.3 mmol). The reaction mixture was stirred for 3 h at room temperature, and then diluted with EtOAc (50 mL). The organic phase was separated and then washed successively with aq. HCl (1M), sat. aq. $NaHCO_3$, and brine, dried over $Na_2SO_4$. After removal of the voaltils under vacuum, the residue was purified by preparative TLC (DCM:MeOH 20:1) to give 62 as a white solid. LCMS-ESI (m/z): 629 (M+H)$^+$.

Benzyl ((S)-1-(((S)-1-(((S,E)-5-hydroxy-1-((S)-2-oxopyrrolidin-3-yl)pent-3-en-2-yl)amino)-4-methyl-1-oxopentan-2-yl)amino)-3-(naphthalen-1-yl)-1-oxopropan-2-yl)carbamate (63)

To a solution of 60 (67 mg, 0.1 mmol) in DCM (3 mL) was added DIBAL (1 M, 0.2 mL, 0.3 mmol) at 0° C. The reaction was stirred for 2 h at 0° C. and then quenched with 1 M HCl (0.1 mL). The reaction mixture was warmed up to room temperature and diluted with EtOAc (15 mL). The organic layer was washed successively with 1 M HCl (5 mL), sat. aq. $NaHCO_3$ (5 mL), and brine, dried over $Na_2SO_4$ and the solvent was removed under vacuum. The residue was purified by silica gel chromatography (DCM: MeOH=20:1) to give 63. $^1$H NMR (400 MHz, Methanol-d$_4$) δ 8.22 (d, J=8.4 Hz, 1H), 7.84 (dd, J=41.9, 7.7 Hz, 2H), 7.53 (dt, J=14.5, 7.6 Hz, 1H), 7.44-7.13 (m, 7H), 5.81-5.63 (m, 1H), 4.68-4.27 (m, 4H), 4.07 (d, J=5.0 Hz, 1H), 3.80-3.62 (m, 1H), 2.60-2.17 (m, 3H), 2.03 (dd, J=24.1, 7.1 Hz, 2H), 1.82-1.45 (m, 6H), 1.31 (s, H), 1.04-0.85 (m, 6H); LCMS-ESI (m/z): 629 (M+H)$^+$.

Benzyl ((S)-1-(((S)-4-methyl-1-oxo-1-(((S,E)-5-oxo-1-((S)-2-oxopyrrolidin-3-yl)pent-3-en-2-yl)amino) pentan-2-yl)amino)-3-(naphthalen-1-yl)-1-oxopropan-2-yl)carbamate (64)

To a solution of alcohol 63 (56 mg, 0.09 mmol) in DCM (4 mL) and DMSO (1 mL) was added DIPEA (0.13 mL, 0.36 mmol) at 0° C. The solution was stirred for 30 min before addition of SO₃·pyridine complex (60 mg, 0.36 mmol). The reaction mixture was then stirred at 0° C. overnight and then diluted with EtOAc (25 mL). The organic phase was separated and then washed successively with aq. HCl (1M, 10 mL), sat. aq. NaHCO₃ (10 mL), and brine, dried over Na₂SO₄. After removal of the volatils under vacuum, the residue was purified by preparative TLC to give 64 as a white solid (mg, 75%). ¹H NMR (400 MHz, Methanol-d₄) δ 9.55 (dd, J=1.6, 7.8 Hz, 1H), 8.21 (d, J=8.4 Hz, 1H), 7.88 (d, J=7.4 Hz, 1H), 7.78 (d, J=6.6 Hz, 1H), 7.48-7.57 (m, 2H), 7.23-7.41 (m, 7H), 6.91-6.97 (m, 1H), 6.14-6.20 (m, 1H), 4.99 (s, 2H), 4.74-4.85 (m, 1H), 4.59-4.63 (m, 1H), 4.37-4.41 (m, 1H), 3.68-3.74 (m, 1H), 3.24-3.29 (m, 2H), 2.45-2.61 (m, 1H), 2.24-2.32 (m, 1H), 1.62-1.84 (m, 5H), 0.89-0.98 (m, 6H); LCMS-ESI (m/z): 627 (M+H)⁺.

tert-Butyl ((S,E)-4-(methylsulfonyl)-1-((S)-2-oxopyrrolidin-3-yl)but-3-en-2-yl)carbamate (65)

To a solution of diethyl ((methylsulfonyl)methyl)phosphonate (1.46 g, 6.3 mmol) in THF (60 mL) was added BuLi (1 M, 6.5 mL, 6.5 mmol) dropwise at −78° C. After stirred for 30 min, aldehyde 49 (1.35 g, 5.3 mmol) in THF (10 mL) was added over 30 min. The reaction mixture was warmed up to it over 1 h and stirred for further 3 h. Quenched the reaction by addition of MeOH (1 mL), and the solvent was removed in vacuum. The residue was partitioned between EtOAc (150 mL) and aq. 1N HCl (80 mL), and the organic phase was washed respectively with aq. NaHCO₃ and brine, dried (Na₂SO₄), concentrated, and the residue was purified by silica gel chromatography (DCM:MeOH=20:1) to afford 65 (25%). LCMS-ESI (m/z): 333 [M+H].

Benzyl ((S)-1-(((S)-4-methyl-1-(((S,E)-4-(methylsulfonyl)-1-((S)-2-oxopyrrolidin-3-yl)but-3-en-2-yl) amino)-1-oxopentan-2-yl)amino)-3-(naphthalen-1-yl)-1-oxopropan-2-yl)carbamate (66)

A solution of compound 65 (330 mg, 1 mmol) and trifluoroacetic acid (2 mL) in DCM (6 mL) was stirred at room temperature for 3 h. The solvent was removed under vacuum and the residue coevaporated three times with toluene. The residue was then dissolved in DCM (30 mL) and dipeptide 57 (480 mg, 1.05 mmol), EDCI (250 mg, 1.3 mmol), HOBt (180 mg, 1.3 mmol), and DIPEA (0.7 mL, 4 mmol) were added. The solution was stirred at room temperature overnight before being diluted with EtOAc (80 mL). The organic layer was washed successively with aq. HCl (1M), sat. aq. NaHCO₃ and brine, dried over Na₂SO₄. Removal of the volatils under vacuum and recrystallization of the residue from EtOAc gave 66 as a white solid (27 mg, 31%). ¹H NMR (400 MHz, Methanol-d₄) δ 8.21 (d, J=8.72 Hz, 1H), 7.89 (d, J=7.76 Hz, 1H), 7.79 (d, J=4.84 Hz, 1H), 7.48-7.59 (m, 2H), 7.25-7.40 (m, 7H), 6.86 (dd, J=4.8, 15.32 Hz, 1H), 6.7 (d, J=15.16 Hz, 1H), 5.01-5.05 (m, 2H), 4.70-4.72 (m, 1H), 4.56-4.60 (m, 1H), 4.31-4.34 (m, 1H), 3.66-3.73 (m, 1H), 2.99 (s, 3H), 2.51-2.54 (m, 1H), 2.27-2.29 (m, 1H), 1.61-1.84 (m, 4H), 0.91-0/98 (m, 6H); LCMS-ESI (m/z): 677 (M+H)⁺.

Benzyl ((2S)-1-(((2S)-4-methyl-1-(((1S)-1-(3-(methylsulfonyl)oxiran-2-yl)-2-((S)-2-oxopyrrolidin-3-yl) ethyl)amino)-1-oxopentan-2-yl)amino)-3-(naphthalen-1-yl)-1-oxopropan-2-yl)carbamate (67)

To a solution of TBHP (5.5 M, 50 µL, 0.27 mmol) in THF (5 mL) was added MeLi (2.5 M, 0.1 mL, 0.25 mmol) at −78° C. The resulting mixture was stirred at −78° C. for 15 min and then a solution of compound 66 (123 mg, 0.18 mmol) in THF (1 mL) was added dropwise. The resulting mixture was stirred at 0° C. overnight. Solid Na₂SO₃ (200 mg) was added and the suspension was stirred for 15 min. After dilution with sat. aq. NH₄Cl solution, extraction with EtOAc (30 mL×3), the combined organic layers were washed with brine, dried over Na₂SO₄, and concentrated under vacuum. The crude oil was purified by column chromatography (DCM:MeOH=20:1) to give 67 as a pale yellow solid. ¹H NMR (400 MHz, Methanol-d₄) δ 8.23 (d, J=8.6 Hz, 1H), 7.88 (d, J=8.2 Hz, 1H), 7.78 (d, J=7.3 Hz, 1H), 7.53 (dd, J=17.7, 7.7 Hz, 1H), 7.45-7.18 (m, 6H), 4.98 (d, J=3.6 Hz, 1H), 4.72 (q, J=7.2, 6.7 Hz, 1H), 4.60 (q, J=3.8 Hz, 1H), 4.47 (dd, J=26.2, 3.5 Hz, 1H), 4.19-4.05 (m, 2H), 3.69 (dt, J=13.1, 6.2 Hz, 1H), 3.38 (d, J=6.7 Hz, 1H), 2.58 (d, J=10.3

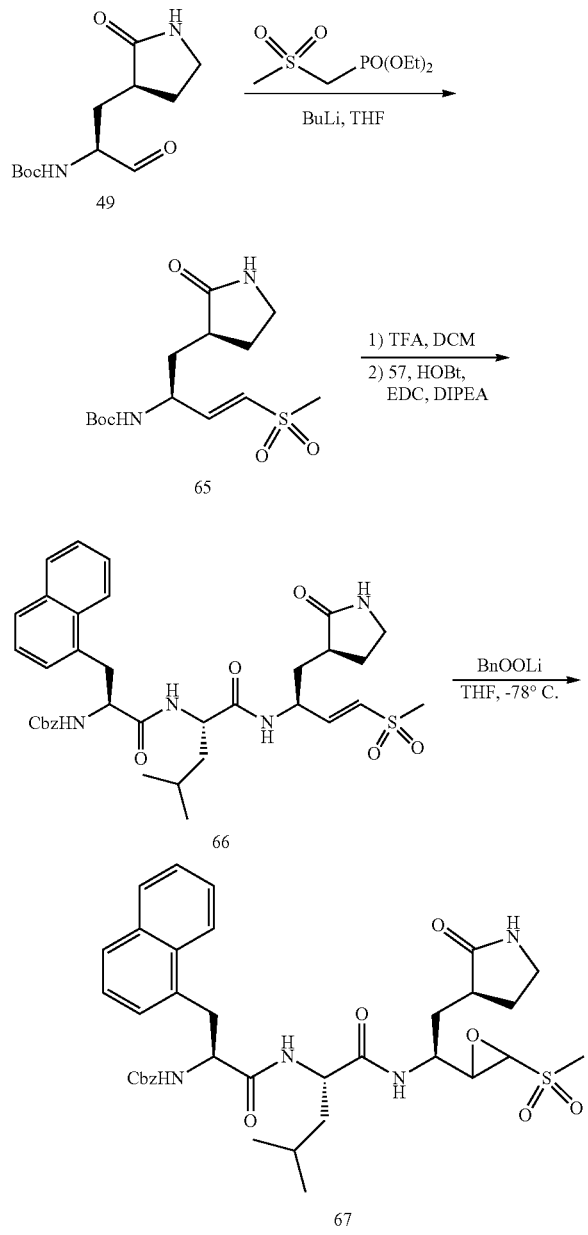

Hz, 1H), 2.43-2.30 (m, 1H), 2.05-1.92 (m, 1H), 1.82 (ddd, J=13.2, 8.8, 4.4 Hz, 1H), 1.75-1.44 (m, 2H), 1.40-1.21 (m, 2H), 0.94 (hept, J=6.7 Hz, 6H); LCMS-ESI (m/z): 693 (M+H)+.

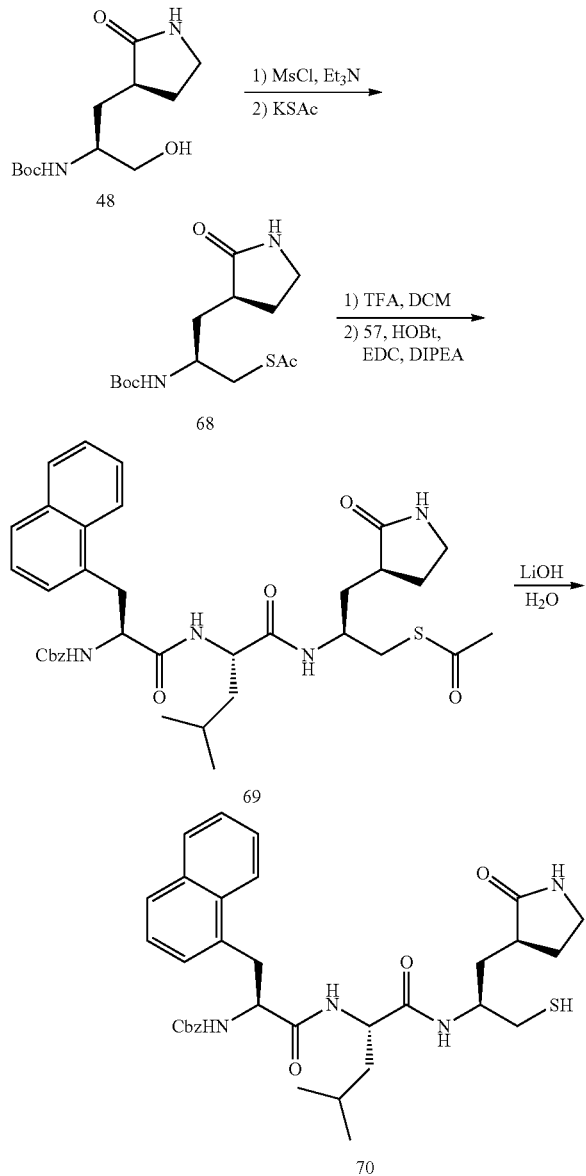

S—((S)-2-((tert-Butoxycarbonyl)amino)-3-((S)-2-oxopyrrolidin-3-yl)propyl) ethanethioate (32)

To a solution of N-[1-(hydroxymethyl)cyclopropyl]carbamic acid-t-butyl ester 2 (3.74 g, 20.0 mmol) and NEt₃ (3.4 mL, 24.0 mmol) in CH₂Cl₂ (100 mL), methanesulfonyl chloride (1.9 mL, 24.0 mmol) was added dropwise at 0° C. The reaction mixture was stirred for 20 h at 0° C. and after removal of the volatile components under reduced pressure, the residue was diluted with H₂O (60 mL). The aqueous phase was extracted with EtOAc (3×60 mL) and the combined organic layers were dried over Na₂SO₄ and concentrated under vacuum. To a solution of the residue in DMF (90 mL) was added K₂CO₃ (6.78 g, 20.8 mmol) and thioacetic acid (1.5 mL, 20.8 mmol). The reaction mixture was stirred for 24 h at room temperature and then the volatile components were removed under reduced pressure. 1N HCl (90 mL) was added to the residue and the aqueous phase was extracted with EtOAc (3×100 mL). The combined organic phases were dried over Na₂SO₄ and concentrated under vacuum. Recrystallization of the residue from hexane/Et₂O yielded 68 (2.97 g, 12.1 mmol, 61%) as pale yellow solid. LCMS-EST (m/z): 317 [M+H].

S-((5S,8S,11S)-8-Isobutyl-5-(naphthalen-1-ylmethyl)-3,6,9-trioxo-11-(((S)-2-oxopyrrolidin-3-yl)methyl)-1-phenyl-2-oxa-4,7,10-triazadodecan-12-yl) ethanethioate (69)

A solution of compound 68 (130 mg, 0.41 mmol) in DCM (6 mL) and trifluoroacetic acid (2 mL) was stirred at room temperature for 2 h. The solvent was removed under vacuum, the residue coevaporated three times with toluene. To a solution of the dry residue in DCM (20 mL) was added dipeptide 57 (200 mg, 0.43 mmol), EDCI (103 mg, 0.54 mmol), HOBt (73 mg, 0.54 mmol), and DIPEA (0.3 mL, 1.72 mmol). The solution was stirred at room temperature overnight before being diluted with EtOAc (80 mL). The organic layer was washed successively with aq. HCl (1M), sat. aq. NaHCO₃ and brine, dried over Na₂SO₄. After removal of the solvent under vacuum and recrystallization from EtOAc, the thioacetate 69 was obtained as a white solid (227 mg, 50%). ¹H NMR (400 MHz, Methanol-d₄) δ 8.13 (d, J=8.4 Hz, 1H), 7.89 (d, J=8.0 Hz, 1H), 7.79 (d, J=8.0 Hz, 1H), 7.48-7.59 (m, 2H), 7.30-7.44 (m, 7H), 5.32 (d, J=12.4 Hz, 1H), 5.13 (d, J=12.4 Hz, 1H), 4.42-4.47 (m, 1H), 3.97-4.07 (m, 2H), 3.45-3.51 (m, 1H), 3.24-3.30 (m, 1H), 3.16-3.20 (m, 1H), 2.87-2.93 (m, 1H), 2.29 (s, 3H), 1.67-1.73 (m, 1H), 1.48-1.52 (m, 1H), 1.35-1.42 (m, 1H), 1.09-1.16 (m, 1H), 0.92-0.97 (m 1H), 0.60 (d, J=6.4 Hz, 3H), 0.52 (d, J=6.4 Hz, 3H); LCMS-EST (m/z): 661 [M+H].

Benzyl ((S)-1-(((S)-1-(((S)-1-mercapto-3-((S)-2-oxopyrrolidin-3-yl)propan-2-yl)amino)-4-methyl-1-oxopentan-2-yl)amino)-3-(naphthalen-1-yl)-1-oxopropan-2-yl)carbamate (70)

A solution of thioacetate 60 (21 mg, 0.03 mmol) and LiOH (2.4 mg, 0.1 mmol) in methanol (1 ml), and the mixture was stirred for 3 days in room temperature. The solvent was removed under vacuum and the residue was purified by preparative TLC (DCM:MeOH=20:1) to give solid thiol 70 in quantitative yield. ¹H NMR (400 MHz, Methanol-d₄) δ 8.13 (d, J=8.4 Hz, 1H), 7.89 (d, J=8.0 Hz, 1H), 7.79 (d, J=8.0 Hz, 1H), 7.48-7.59 (m, 2H), 7.30-7.44 (m, 7H), 5.32 (d, J=12.4 Hz, 1H), 5.13 (d, J=12.4 Hz, 1H), 4.42-4.47 (m, 1H), 3.97-4.07 (m, 2H), 3.45-3.51 (m, 1H), 3.24-3.30 (m, 1H), 3.16-3.20 (m, 1H), 2.87-2.93 (m, 1H), 1.67-1.73 (m, 1H), 1.48-1.52 (m, 1H), 1.35-1.42 (m, 1H), 1.09-1.16 (m, 1H), 0.92-0.97 (m 1H), 0.60 (d, J=6.4 Hz, 3H), 0.52 (d, J=6.4 Hz, 3H); LCMS-ESI (m/z): 619 [M+H].

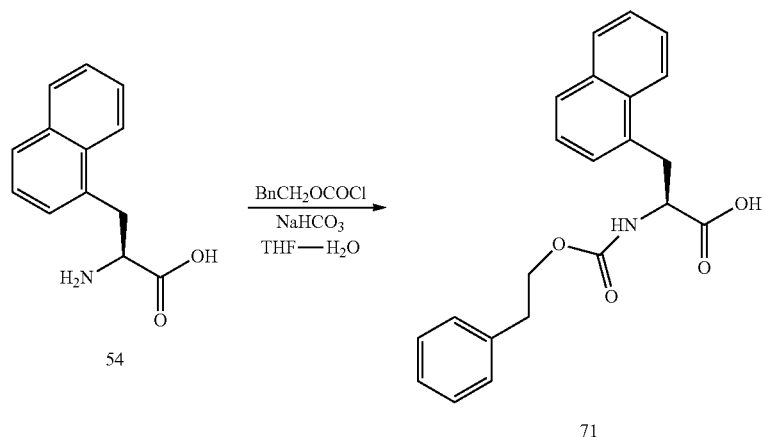
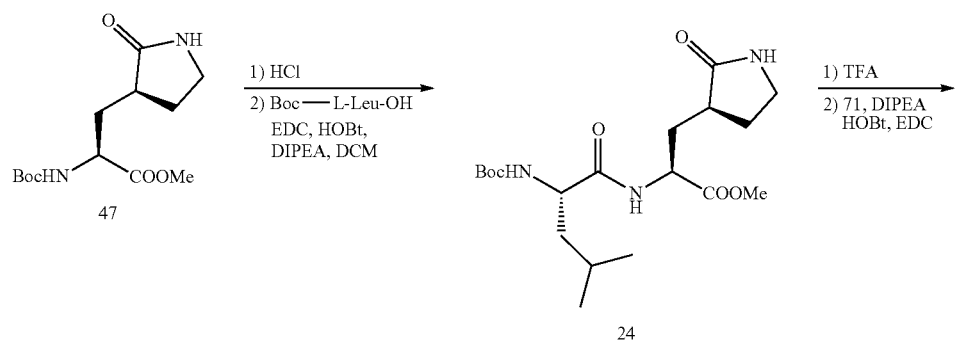
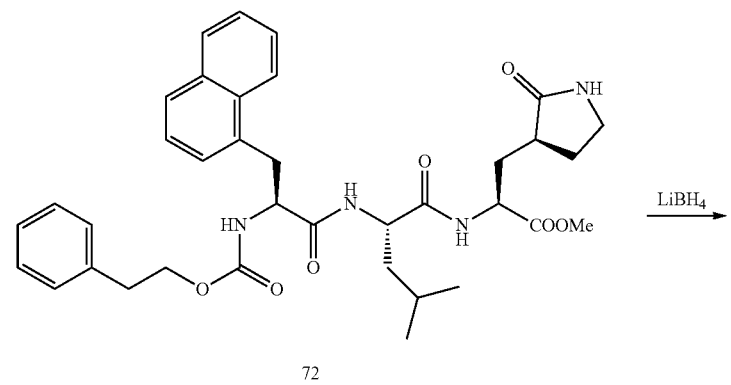
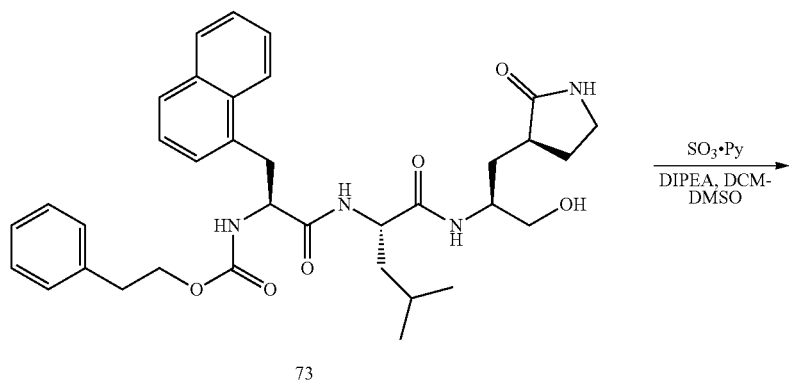

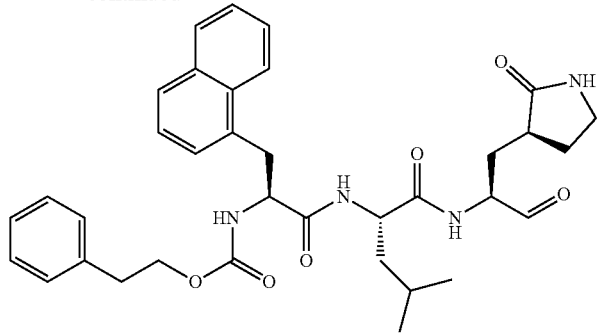

74

(S)-3-(naphthalen-1-yl)-2-((phenethoxycarbonyl) amino)propanoic acid (71)

To a mixture of amino acid a (545 mg, 2.53 mmol), NaHCO$_3$ (320 mg, 3.8 mmol) in THF—H$_2$O (2:3, 20 mL) was added PhCH$_2$CH$_2$OCOCl (0.33 mL, 2.78 mmol) at 0° C. The reaction mixture stirred at rt for 5 h and the acidified with 1 N HCl (8-10 mL) to pH 2.0, organic solvents were then removed under vacuum and the remaining aqueous phase extracted with EtOAc (20 mL×3). The combined organic layers were washed with brine, dried, and concentrated under vacuum to give 71 as a white solid after recrystallization from EtOAc. $^1$H NMR (400 MHz, Chloroform-d) δ 8.12 (d, J=8.4 Hz, 1H), 7.90 (d, J=8.0 Hz, 1H), 7.82 (d, J=8.2 Hz, 1H), 7.54 (q, J=8.1, 7.1 Hz, 2H), 7.15-7.48 (m, 7H), 5.13 (m, 1H), 4.79 (m, 1H), 4.27 (m, 2H), 3.76 (d, J=13.7 Hz, 1H), 3.50 (m, 1H), 2.89 (m, 2H). LCMS-ESI (m/z): 364 [M+H].

Methyl (S)-2-((S)-2-((tert-butoxycarbonyl)amino)-4-methylpentanamido)-3-((S)-2-oxopyrrolidin-3-yl) propanoate (24)

To a solution of compound 47 (4.14 g, 14.47 mmol) in dioxane (30 mL) was added HCl (4 M in dioxane, 20 mL). The reaction mixture was stirred at room temperature for 2 h and the solvent removed under vacuum. The residue was carefully dried in vacuo for 5 h and then used directly in the next step without further purification. The residue was dissolved in DCM (100 mL) and Boc-L-Leu-OH (4.02 g, 17.4 mmol), EDCI (3.61 g, 18.8 mmol), HOBt (2.54 g, 18.8 mmol), and DIPEA (10.4 mL, 60 mmol) were added. The solution was stirred at room temperature overnight before solvents were removed under vacuum. EtOAc (200 mL) was then added and the organic layer was washed successively with aq. HCl (1M), sat. aq. NaHCO$_3$ and brine and finally dried over Na$_2$SO$_4$. After removal of the solvent under vacuum and recrystallization from EtOAc, compound 24 was obtained as a white solid (72%). LCMS-ESI (m/z): 400 [M+H].

Methyl (6S,9S,12S)-9-isobutyl-6-(naphthalen-1-ylmethyl)-4,7,10-trioxo-12-(((S)-2-oxopyrrolidin-3-yl)methyl)-1-phenyl-3-oxa-5,8,11-triazatridecan-13-oate (72)

A solution of compound 24 (520 mg, 1.3 mmol) and TFA (5 mL) in DCM (20 mL) was stirred at room temperature for 3 h. The solvent was removed under vacuum and the residue used in the next step without further purification. The residue was dissolved in DCM (40 mL) and compound 21 (494 mg, 1.2 mmol mmol), EDCI (310 mg, 1.62 mmol), HOBt (220 mg, 1.62 mmol), and DIPEA (0.88 mL, 5 mmol) were added The solution was stirred at room temperature overnight before solvents were removed under vacuum. EtOAc (100 mL) was then added and the organic layer was washed successively with aq. HCl (1M), sat. aq. NaHCO$_3$ and brine and finally dried over Na$_2$SO$_4$. After removal of the solvent under vacuum and recrystallization from EtOAc, compound 72 was obtained as a white solid (62%). $^1$H NMR (400 MHz, Methanol-d4) δ 8.16 (d, J=8.4 Hz, 1H), 7.89 (d, J=8.1 Hz, 1H), 7.80 (d, J=7.9 Hz, 1H), 7.54 (dt, J=27.5, 7.3 Hz, 2H), 7.44-7.20 (m, 7H), 4.64 (m, 1H), 4.52-4.40 (m, 1H), 4.34-4.11 (m, 3H), 3.72 (d, J=15.2 Hz, 1H), 3.64 (s, 2H), 3.47 (d, J=7.8 Hz, 1H), 3.30-3.18 (m, 1H), 2.91 (t, J=6.9 Hz, 1H), 2.50 (d, J=10.7 Hz, 1H), 2.28 (ddd, J=34.9, 17.0, 7.3 Hz, 2H), 1.92-1.37 (m, 2H), 1.14 (d, J=6.0 Hz, 1H), 0.64 (d, J=12.8 Hz, 6H); LCMS-ESI (m/z): 645 [M+H].

Phenethyl ((S)-1-(((S)-4-methyl-1-oxo-1-(((S)-1-oxo-3-((S)-2-oxopyrrolidin-3-yl)propan-2-yl)amino) pentan-2-yl)amino)-3-(naphthalen-1-yl)-1-oxopropan-2-yl)carbamate (74)

To a solution of methyl ester 72 (420 mg, 0.65 mmol) in THF-EtOH (2:3, 10 mL) were added LiBH$_4$ (4M, 250 μL, 1 mmol) at 0° C. The resulting mixture was stirred at room temperature for 3 h and then quenched with aq. HCl (1 M). Ethyl acetate (50 mL) was added and the organic phase was further washed with brine and dried over Na$_2$SO$_4$. After removal of the solvent under vacuum compound 73 was obtained as a white solid. To a solution of alcohol 73 in a mixture of DCM (16 mL) and DMSO (4 mL) was added at 0° C. DIPEA (360 μL, 2.07 mmol). The resulting solution was stirred for 30 min before addition of SO$_3$ pyridine complex (330 mg, 2.06 mmol). The reaction mixture was stirred overnight at 0° C. and then diluted with EtOAc (100 mL). The organic phase was then washed successively with aq. HCl (1M), sat. aq. NaHCO$_3$, and brine and dried over Na$_2$SO$_4$. After removal of the solvent under vacuum and recrystallization from EtOAc, compound 74 was obtained as a white solid (68%). $^1$H NMR (400 MHz, Methanol-d$_4$) δ 8.16 (d, J=8.4 Hz, 1H), 7.89 (d, J=7.8 Hz, 1H), 7.79 (d, J=8.0 Hz, 1H), 7.64-7.44 (m, 2H), 7.15-7.46 (m, 7H), 4.53-4.41 (m, 1H), 4.31-4.14 (m, 3H), 3.69 (s, 1H), 3.64 (s, 2H), 3.51-3.44 (m, 1H), 3.29-3.14 (m, 2H), 2.90 (q, J=7.2 Hz, 2H), 2.59-2.44 (m, 1H), 2.39-2.14 (m, 1H), 1.91-1.64 (m, 1H), 1.64-1.37 (m, 1H), 0.72-0.51 (m, 6H); LCMS-ESI (m/z): 615 [M+H].

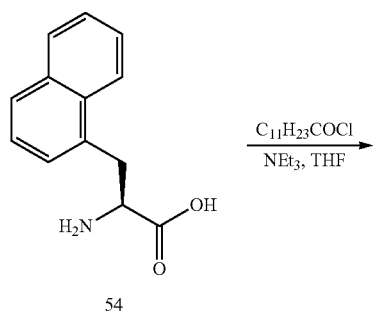

54

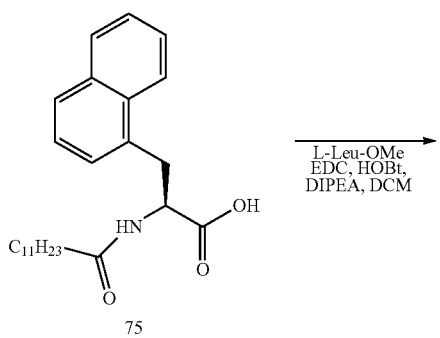

75

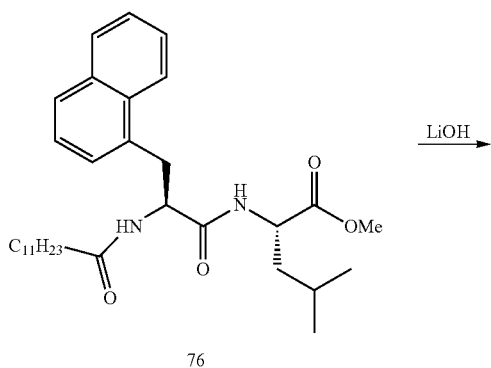

76

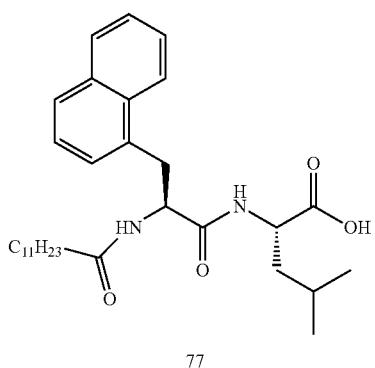

77

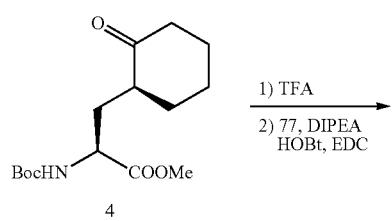

4

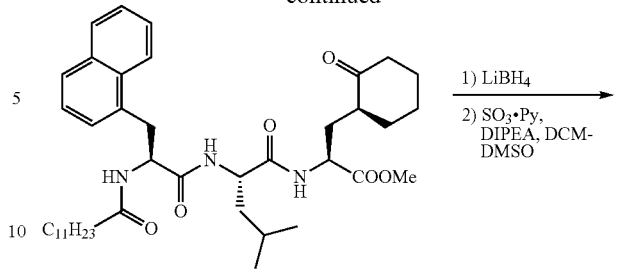

78

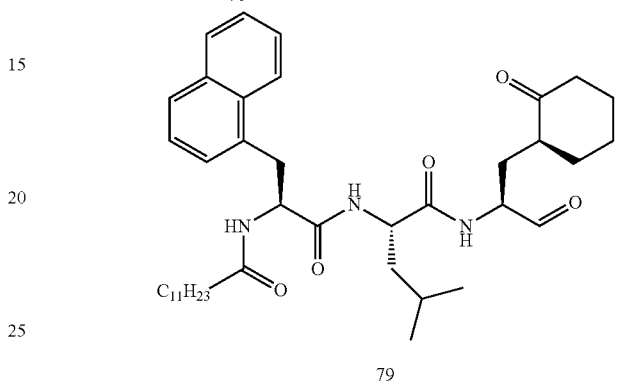

79

(S)-2-Dodecanamido-3-(naphthalen-1-yl)propanoic acid (75)

To a mixture of amino acid 54 (215 mg, 1 mmol), NaHCO$_3$ (125 mg, 1.5 mmol) in THF—H$_2$O (2:3, 10 mL) was added C$_{11}$H$_{23}$COCl (0.33 mL, 2.78 mmol) at 0° C. The reaction mixture was stirred at it for 2 h and then acidified with 1 N HCl (8-10 mL) to reach pH 2.0. After removal of the solvent the aqueous layer was extracted with EtOAc (20 mL×3), and the combined organic phases were washed with brine, dried over Na$_2$SO$_4$. After removal of the solvent under vacuum and recrystallization from EtOAc, compound 75 (73%) was obtained as a white solid. LCMS-ESI (m/z): 398 [M+H].

Methyl ((S)-2-dodecanamido-3-(naphthalen-1-yl)propanoyl)-L-leucinate (76)

To a solution of compound 75 (380 mg, 1.05 mmol) and L-Leu-OMe (230 mg, 1.27 mmol) in DCM (30 mL) were added EDCI (260 mg, 1.35 mmol), HOBt (185 mg, 1.34 mmol), and DIPEA (0.73 mL, 4.2 mmol). The reaction mixture was stirred overnight at room temperature and then H$_2$O (800 mL) and EtOAc (100 mL) were added. The organic phase was washed successively with aq. HCl (1 M, 50 mL), sat. aq. NaHCO$_3$ (50 mL) and brine (500 mL), and then dried over Na$_2$SO$_4$. After removal of the solvent under vacuum and recrystallization from EtOAc, compound 76 (350 mg, 65%) was obtained. LCMS-ESI (m/z): 525 [M+H].

((S)-2-Dodecanamido-3-(naphthalen-1-yl)propanoyl)-L-leucine (77)

To a solution of methyl ester 76 (345 mg, 0.66 mmol) in THF-MeOH—H$_2$O (3:1:1, 10 mL) was added a solution of LiOH H$_2$O (32 mg, 1.33 mmol) in H$_2$O (1 mL). The reaction mixture was stirred overnight at room temperature. The volatiles were removed under vacuum to give a colourless residue that was partitioned between EtOAc and aq. HCl (1M). The organic layer was separated, washed successively with aq. HCl (1M) and brine, then dried over Na$_2$SO$_4$, After removal of the solvent under vacuum and recrystallization from EtOAc, compound 77 was obtained as a white solid (430 mg, 96%). LCMS-ESI (m/z): 692 [M+H].

N—((S)-1-(((S)-4-methyl-1-oxo-1-(((S)-1-oxo-3-((S)-2-oxocyclohexyl)propan-2-yl)amino)pentan-2-yl)amino)-3-(naphthalen-1-yl)-1-oxopropan-2-yl) dodecanamide (79)

To a solution of methyl ester 4 (466 mg, 0.67 mmol) in THF-EtOH (2:3, 20 mL) was added LiBH$_4$ (2 M, 440 µL, 0.88 mmol) at 0° C. The resulting mixture was stirred at room temperature for 3 h and then quenched with aq. HCl (1 M). After addition of ethyl acetate (50 mL) the organic phase was separated and further washed with brine and dried over Na$_2$SO$_4$. Removal of the solvent under vacuum afforded compound 78 as a white solid which was used directly in the next without further purification. To a solution of alcohol 78 (70 mg, 0.11 mmol) in a mixture of DCM (3 mL) and DMSO (1 mL) was added at 0° C. DIPEA (90 µL, 0.5 mmol). The solution was stirred at this temperature for 10 min before addition of SO$_3$ pyridine complex (70 mg, 0.43 mmol). The reaction mixture was stirred overnight at 0° C. and then diluted with EtOAc (50 mL). The organic phase was separated and then washed successively with aq. HCl (1M), sat. aq. NaHCO$_3$, and brine, dried over Na$_2$SO$_4$. After removal of the solvent under vacuum and recrystallization from EtOAc, compound 79 was obtained as a white solid (48%). $^1$H NMR (400 MHz, Methanol-d$_4$) δ 8.23 (d, 0.1=6.4 Hz, 1H), 7.87 (d, J=6.8 Hz, 1H), 7.75-7.78 (m, 1H), 7.48-7.59 (m, 2H), 7.37-7.42 (m, 2H), 4.37-4.44 (m, 1H), 3.95-4.04 (m, 1H), 3.67-3.75 (m, 1H), 3.45-3.55 (m, 2H), 3.21-3.28 (m, 2H), 2.27-2.35 (m, 1H), 2.08-2.18 (m, 4H), 1.60-1.82 (m, 7H), 1.19-1.43 (m, 18H), 0.90-0.98 (m, 9H); LCMS-ESI (m/z): 662 [M+H].

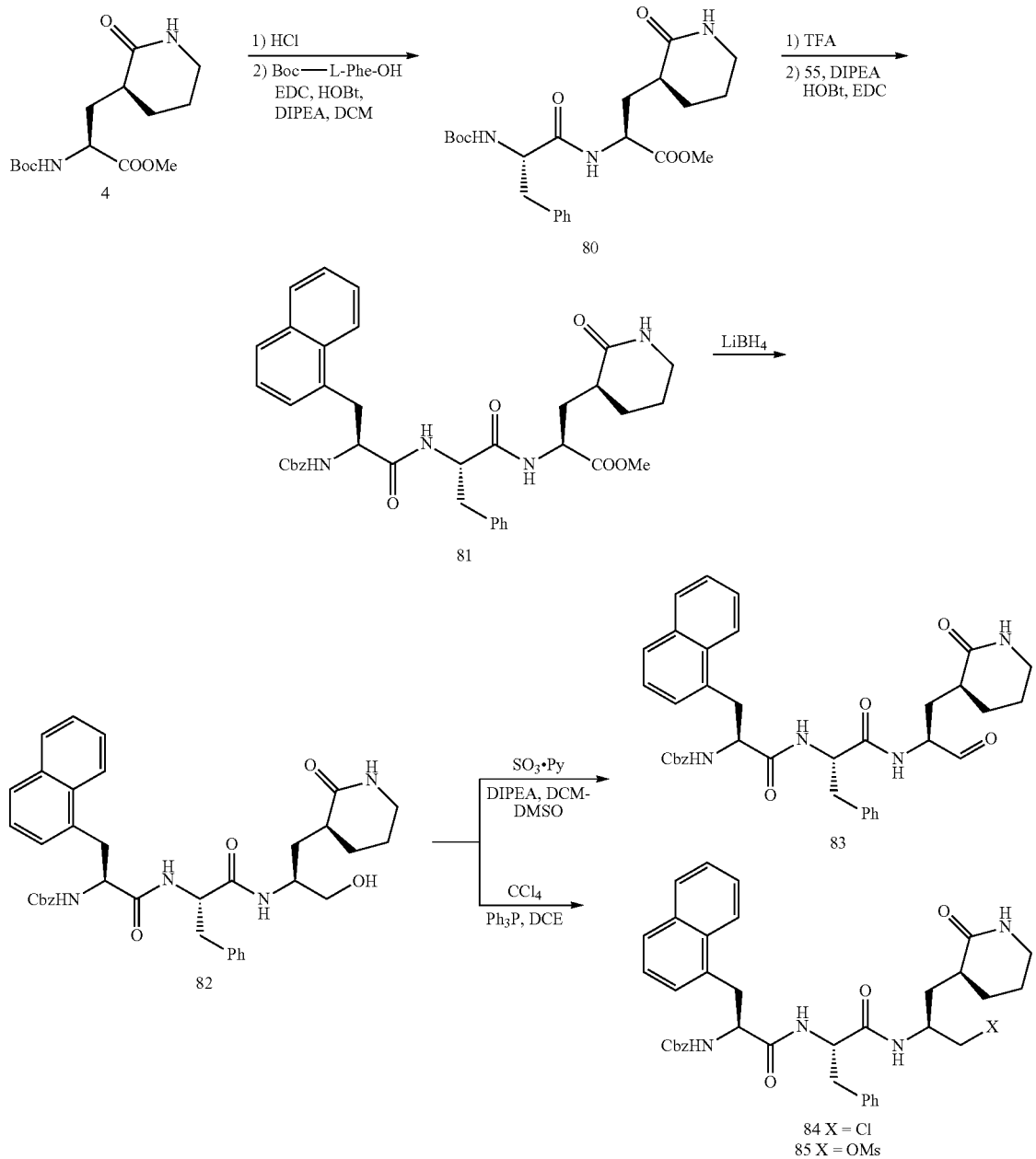

Methyl (S)-2-((S)-2-((tert-butoxycarbonyl)amino)-4-methylpentanamido)-3-((S)-2-oxocyclohexyl) propanoate (80)

To a solution of compound 4 (630 mg, 2.1 mmol) in dioxane (8 mL) was added HCl (4M in dioxane, 8 mL). The solution was stirred at room temperature for 3 h and the solvent was removed under reduced pressure. The obtained residue was used in the next step without further purification. To a solution of the residue in DCM (80 mL) was added L-Phe-OH (725 mg, 2.73 mmol), EDCI (564 mg, 2.94 mmol), HOBt (400 mg, 2.94 mmol), and DIPEA (1.54 mL, 8.83 mmol). The reaction mixture was stirred at room temperature overnight before evaporation of the solvent under vacuum. EtOAc (200 mL) was added to the residue and the organic layer was washed successively with aq. HCl (1 M), sat. aq. NaHCO$_3$, brine and dried over Na$_2$SO$_4$. After removal of the solvent under vacuum and recrystallization from EtOAc, compound 80 was obtained as a white solid (72%). $^1$H NMR (400 MHz, Chloroform-d) δ 7.69 (di, J=7.5 Hz, 1H), 7.34-7.16 (m, 7H), 6.36 (s, 1H), 5.19 (di, J=8.4 Hz, 1H), 4.56 (dd, J=19.2, 10.7 Hz, 2H), 3.71 (s, 3H), 3.16 (dd, J=13.9, 5.5 Hz, 1H), 3.03 (dd, J=14.1, 7.0 Hz, 1H), 2.35 (ddd, J=14.0, 11.3, 5.1 Hz, 1H), 2.24 (dq, J=14.9, 5.7 Hz, 1H), 2.15-2.00 (m, 2H), 1.88 (dtd, J=14.3, 7.9, 3.9 Hz, 2H), 1.80-1.61 (m, 1H), 1.60-1.46 (m, 1H), 1.37 (d, J=17.7 Hz, 9H); LCMS-ESI (nm/z): 413 [M+H].

Methyl (5S,8S,11S)-8-benzyl-5-(naphthalen-1-ylmethyl)-3,6,9-trioxo-11-(((S)-2-oxopiperidin-3-yl)methyl)-1-phenyl-2-oxa-4,7,10-triazadodecan-12-oate (81)

A solution of compound 80 (592 mg, 1.28 mmol) and TFA (5 mL) in DCM (15 mL) was stirred at room temperature for 2 h. The solvent was removed under vacuum and the residue used in the next step without further purification. The residue was dissolved in DCM (50 mL) and compound 9 (540 mg, 1.54 mmol mmol), EDCI (320 mg, 1.68 mmol), HOBt (225 mg, 1.67 mmol), and DIPEA (0.9 mL, 5.2 mmol) were added. The solution was stirred at room temperature overnight before removal of the solvent under vacuum and addition of EtOAc (150 mL). The organic layer was washed successively with aq. HCl (1M), sat. aq. NaHCO$_3$, brine and dried over Na$_2$SO$_4$. After removal of the solvent under vacuum and recrystallization from EtOAc, compound 81 was obtained as a white solid (62%). LCMS-ESI (m/z): 679 [M+H].

Benzyl ((S)-1-(((S)-1-(((S)-1-hydroxy-3-((S)-2-oxopiperidin-3-yl)propan-2-yl)amino)-1-oxo-3-phenylpropan-2-yl)amino)-3-(naphthalen-1-yl)-1-oxopropan-2-yl)carbamate (82)

To a solution of methyl ester 81 (870 mg, 1.28 mmol) in THF-EtOH (2:3, 30 mL) was added LiBH$_4$ (2 M, 1 mL, 2 mmol) at 0° C. The resulting mixture was stirred at room temperature for 3 h and then quenched with aq. HCl (1 M). Ethyl acetate (50 mL) was added and the organic phase was washed with brine and dried over Na$_2$SO$_4$. Removal of the solvent under vacuum gave 82 as a white solid which was used in the next step without further purification. $^1$H NMR (400 MHz, Methanol-d$_4$) δ 8.14 (d, J=8.5 Hz, 1H), 7.85 (d, J=8.3 Hz, 2H), 7.74 (d, J=8.1 Hz, 1H), 7.49 (dq, J=14.6, 7.2 Hz, 2H), 7.27 (tdd, J=16.9, 11.8, 7.9 Hz, 12H), 4.96 (d, J=4.2 Hz, 2H), 4.58 (dt, J=19.6, 7.1 Hz, 2H), 4.02-3.89 (m, 1H), 3.55 (dd, J=14.3, 5.4 Hz, 1H), 3.48-3.06 (m, 4H), 2.98 (dd, J=13.6, 8.0 Hz, 1H), 2.24 (h, J=5.7, 4.5 Hz, 1H), 1.98 (dtq, J=12.7, 6.3, 3.5 Hz, 3H), 1.79-1.53 (m, 4H), 1.50-1.35 (m, 1H); LCMS-ESI (m/z): 651 [M+H].

Benzyl ((S)-3-(naphthalen-1-yl)-1-oxo-1-(((S)-1-oxo-1-(((S)-1-oxo-3-((S)-2-oxopiperidin-3-yl)propan-2-yl)amino)-3-phenylpropan-2-yl)amino)propan-2-yl)carbamate (83)

To a solution of 82 (70 mg, 0.11 mmol) in a mixture of DCM (3 mL) and DMSO (1 mL) was added at 0° C. DIPEA (90 µL, 0.5 mmol). After 10 minutes at this temperature, SO$_3$ pyridine complex (70 mg, 0.43 mmol) was added and the reaction mixture was stirred overnight at 0° C. After addition of EtOAc (50 mL), the organic layer was washed successively with aq. HCl (1M), sat. aq. NaHCO$_3$, brine and dried over Na$_2$SO$_4$. After removal of the solvent under vacuum and recrystallization from EtOAc, compound 83 as a white solid (56%). $^1$H NMR (400 MHz, Methanol-d$_4$) δ 9.22 (s, 0.3H), 8.22-8.07 (m, 1H), 7.87 (d, J=8.1 Hz, 1H), 7.76 (d, J=8.1 Hz, 1H), 7.51 (dq, J=14.6, 7.1 Hz, 2H), 7.39-7.12 (m, 12H), 5.06-4.94 (m, 2H), 4.69-4.46 (m, 1H), 4.35-4.21 (m, 1H), 3.98 (d, J=12.3 Hz, 1H), 3.57 (dt, J=14.2, 7.7 Hz, 1H), 3.28-2.95 (m, 5H), 2.29-1.93 (m, 1H), 1.81 (d, J=14.4 Hz, 1H), 1.66 (s, 1H), 1.46 (q, J=11.5, 10.3 Hz, 1H), 1.35-1.18 (m, 1H); LCMS-ESI (m/z): 649 [M+H].

Benzyl ((S)-1-(((S)-1-(((S)-1-chloro-3-((S)-2-oxopiperidin-3-yl)propan-2-yl)amino)-1-oxo-3-phenylpropan-2-yl)amino)-3-(naphthalen-1-yl)-1-oxopropan-2-yl)carbamate (84)

A solution of 82 (32 mg, 0.05 mmol), Ph$_3$P (50 mg, 0.19 mmol), CCl$_4$ (0.1 mL) in 1,2-dichloroethane (0.5 mL) was heated at 80° C. for 3 min under microwave irradiation. After removal of the solvent under vacuum, the residue was purified by preparative TLC to give 84 (78%) as a white solid. $^1$H NMR (400 MHz, Methanol-d4) δ 8.15 (d, J=8.1 Hz, 1H), 7.87 (d, J=8.0 Hz, 1H), 7.76 (d, J=8.1 Hz, 1H), 7.51 (dq, J=15.3, 7.5 Hz, 2H), 7.27 (tdd, J=20.7, 9.9, 5.4 Hz, 13H), 4.96 (d, J=19.5 Hz, 2H), 4.57 (dq, J=21.7, 6.2, 5.1 Hz, 2H), 4.19-4.09 (m, 1H), 3.67-3.37 (m, 2H), 3.27-2.96 (m, 5H), 2.27 (s, 1H), 2.19-1.88 (m, 2H), 1.85-1.52 (m, 3H); LCMS-ESI (m/z): 669 [M+H].

Benzyl ((S)-3-(naphthalen-1-yl)-1-oxo-1-(((S)-1-oxo-1-(((S)-1-oxo-3-((S)-2-oxopiperidin-3-yl)propan-2-yl)amino)-3-phenylpropan-2-yl)amino)propan-2-yl)carbamate (85)

To a solution of 82 (41 mg, 0.06 mmol) and NEt$_3$ (30 µL, 0.2 mmol) in CH$_2$Cl$_2$ (5 mL) was added methanesulfonyl chloride (9 µL, 0.09 mmol) at 0° C. The reaction mixture was stirred for 1 h at this temperature. After removal of the volatile components under reduced pressure, the residue was subjected to preparative TLC to give 85 as a white solid. $^1$H NMR (400 MHz, Methanol-d$_4$) δ 8.20-8.05 (m, 2H), 7.87 (d, J=7.9 Hz, 1H), 7.77 (t, J=8.2 Hz, 1H), 7.51 (dd, J=13.4, 7.6 Hz, 2H), 7.27 (tt, J=17.2, 7.0 Hz, 6H), 5.06-4.96 (m, 2H), 4.64-4.44 (m, 1H), 4.07 (q, 0.1=7.7, 5.7 Hz, 1H), 3.65-3.49 (m, 1H), 3.23 (d, 0.1=5.0 Hz, 3H), 3.04 (s, 3H), 2.37-2.21 (m, 2H), 2.22-1.94 (m, 1H).

Example 2

Cellular Toxicity Assays

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide was included as positive cytotoxic control, and untreated cells exposed to solvent were included as negative controls. The cytotoxicity $CC_{50}$ was obtained from the concentration-response curve using the median effective method described previously (see Chou T.-C. & Talalay P. *Adv. Enzyme Regul.* 1984, 22, 27-55; Belen'kii M. S. & Schinazi R. F. Antiviral Res. 1994, 25, 1-11). The results are shown in Table 1 below:

TABLE 1

Cytotoxicity, $CC_{50}$, µM (% inhibition)

| Compound | Cytotoxicity; $CC_{50}$ (µM) PBM | CEM | VERO | Huh7 |
| --- | --- | --- | --- | --- |
| 11 | >100 | >100 | >100 | >10 |
| 19 | 24 | 32 | 20 | >10 |
| 23 | >100 | 39 | >100 | >10 |
| 29 | >100 | 38 | >100 | >10 |
| 35 | 52 | 35 | >100 | 60 |
| 36 | 45 | 9 | >100 | 8 |
| 37 | 44 | 18 | >100 | 11 |
| 38 | 18 | 6 | 22 | 13 |
| 39 | 39 | 2 | 11 | 14 |
| 67 | >100 | 64 | >100 | ND |
| 83 | 48.7 | 17.0 | 41.2 | ND |
| 84 | 75.0 | 26.6 | 51.7 | ND |

In the table, Compounds 11, 19, 28 and 29 have the following structures:

11
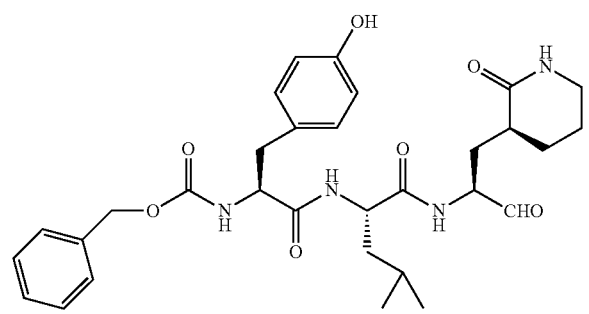

19
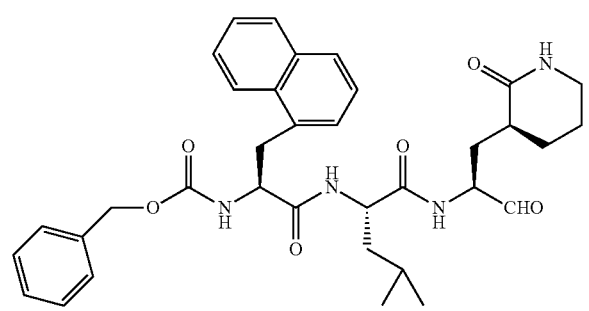

23
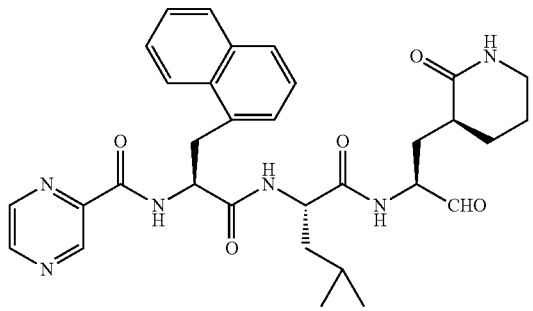

29
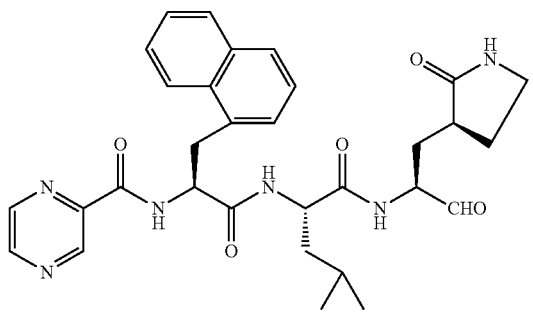

Compounds 35, 36, 37, 38, 39, 67, 83, and 84 have the following structures:

35
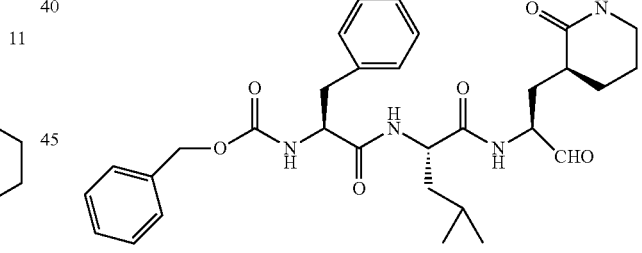

36
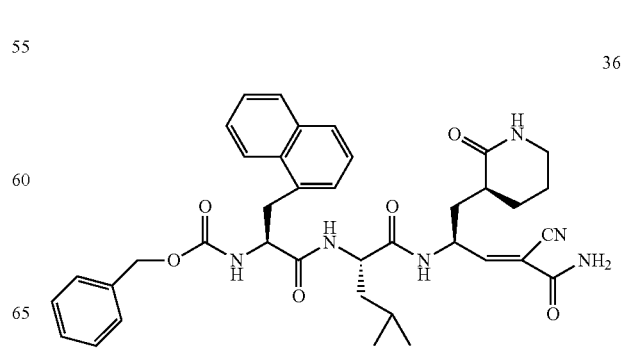

37

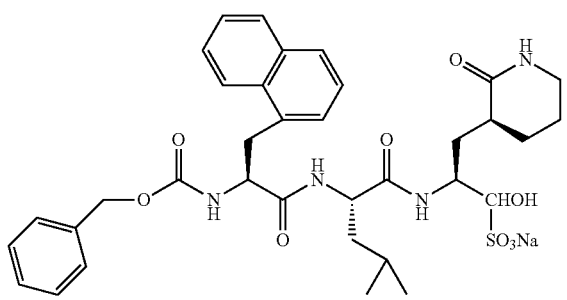

38

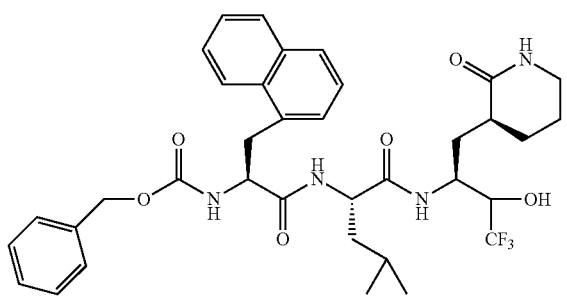

39

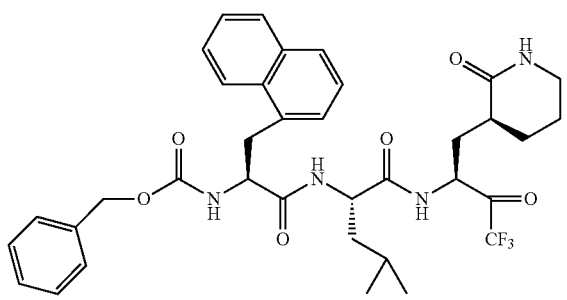

67

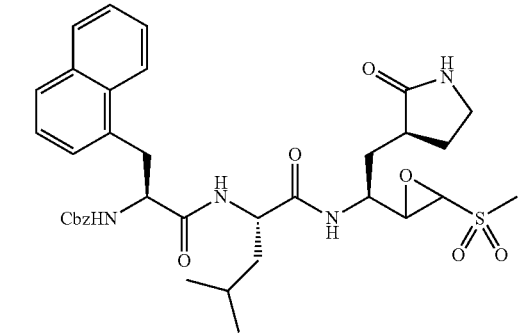

83

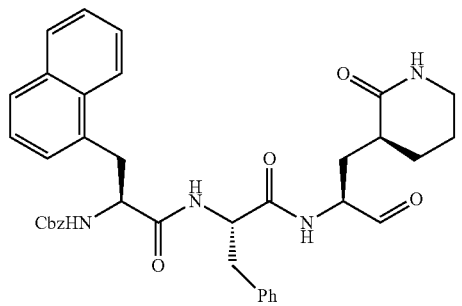

84

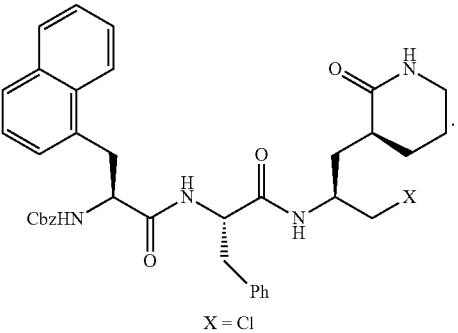

X = Cl

Example 3

Mitochondrial Toxicity Assays in HepG2 Cells:

i) Effect of Compounds on Cell Growth and Lactic Acid Production: The effect on the growth of HepG2 cells was determined by incubating cells in the presence of 0 μM, 0.1 μM, 1 μM, 10 μM and 100 μM drug. Cells (5×104 per well) were plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number was determined using a hemocytometer. Also taught by Pan-Zhou X-R, Cui L, Zhou X-J, Sommadossi J-P, Darley-Usmer VM. "Differential effects of antiretroviral nucleoside analogs on mitochondrial function in HepG2 cells," Antimicrob. Agents Chemother. 2000; 44:496-503.

To measure the effects of the compounds on lactic acid production, HepG2 cells from a stock culture were diluted and plated in 12-well culture plates at 2.5×104 cells per well. Various concentrations (0 μM, 0.1 μM, 1 μM, 10 μM and 100 μM) of compound were added, and the cultures were incubated at 37° C. in a humidified 5% $CO_2$ atmosphere for 4 days. At day 4, the number of cells in each well was determined and the culture medium collected. The culture medium was then filtered, and the lactic acid content in the medium was determined using a colorimetric lactic acid assay (Sigma-Aldrich). Since lactic acid product can be considered a marker for impaired mitochondrial function, elevated levels of lactic acid production detected in cells grown in the presence of test compounds would indicate a drug-induced cytotoxic effect.

ii) Effect of Compounds on Mitochondrial DNA Synthesis: A real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002, 46: 3854-60). This assay was used in all studies described in this application that determine the effect of compounds on mitochondrial DNA content. In this assay, low-passage-number HepG2 cells were seeded at 5,000 cells/well in collagen-coated 96-well plates. Test compounds were added to the medium to obtain final concentrations of 0 μM, 0.1 μM, 10 μM and 100 μM. On culture day 7, cellular nucleic acids were prepared by using commercially available columns (RNeasy 96 kit; Qiagen). These kits co-purify RNA and DNA, and hence, total nucleic acids are eluted from the columns. The mitochondrial cytochrome c oxidase subunit II (COXII) gene and the β-actin or rRNA gene were amplified from 5 μl of the eluted nucleic acids using a multiplex Q-PCR protocol with suitable primers and probes for both target and reference amplifications. For COXII the following sense, probe and antisense primers were used, respectively: 5'-TGCC CGCCATCATCCTA-3',5'-tetrachloro-6-carboxyfluorescein-(SEQ ID No. 1) TCCTCATCGCCCT-CCCATCCC-TAMRA-3' (SEQ ID No. 2) and 5'-CGTCTGTTTAT GTAAAGGATGCGT-3' (SEQ ID No. 3). For exon 3 of the β-actin gene (GenBank accession number E01094) the sense, probe, and antisense primers are 5'-GCGCGGCTA-CAGCTTCA-(SEQ ID No. 4) 3',5'-6-FAMCACCAC GGCCGAGCCGGGATAMRA-3' (SEQ ID No. 5) and 5'-TCTCCTTAATGTCACGCACGAT-3' (SEQ ID No. 6), respectively. The primers and probes for the rRNA gene are commercially available from Applied Biosystems. Since equal amplification efficiencies are obtained for all genes, the comparative CT method was used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample-CT for target control)-(CT for average reference test-CT for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug indicated mitochondrial toxicity.

Example 4

Mitochondrial Toxicity Assays in Neuro2A Cells

To estimate the potential of the compounds of this invention to cause neuronal toxicity, mouse Neuro2A cells (American Type Culture Collection 131) can be used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimicrob. Agents Chemother.* 2005, 49, 1994-2001). The concentrations necessary to inhibit cell growth by 50% (CC50) can be measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug can be carried out as described above. ddC and AZT can be used as control nucleoside analogs.

Example 5

Assay for Bone Marrow Cytotoxicity

Primary human bone marrow mononuclear cells can be obtained commercially from Cambrex Bioscience (Walkersville, MD). CFU-GM assays is carried out using a bilayer soft agar in the presence of 50 units/mL human recombinant granulocyte/macrophage colony-stimulating factor, while BFU-E assays used a ethylcellulose matrix containing 1 unit/mL erythropoietin (see Sommadossi J P, Carlisle R. Toxicity of 3'-azido-3'-deoxythymidine and 9-(1,3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of cytotoxicity of the (-) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT is used as a positive control. Cells can be incubated in the presence of the compound for 14-18 days at 37° C. with 5% $CO_2$, and colonies of greater than 50 cells can be counted using an inverted microscope to determine the $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 6

Anti-Norovirus Activity

Norwalk virus replicon assays were performed as reported by Constantini et al. (*Antivir Ther* 2012, 17, 981-991). HG23 cells (derived from Huh-7 cells) containing NoV replicon RNA are seeded at a density of 3,000 cells/well in 96-well plates and incubated at 37° C. and 5% $CO_2$ overnight. Compounds were tested at concentrations ranging from 0.1 to 100 μM. Compounds were added in triplicate to 80 to 90% confluent monolayers and incubated at 37° C. and 5% $CO_2$. Untreated cells were included in each plate. Following five days incubation (37° C., 5% $CO_2$), total cellular RNA was isolated with RNeasy96 extraction kit from Qiagen. Replicon RNA and an internal control (TaqMan rRNA control reagents, Applied Biosystems) were amplified in a single step.

The median effective concentrations ($EC_{50}$) ranges of several of the compounds described herein against NoV are shown in Table 3:

TABLE 3

| Anti-NoV activity (μM) | | |
|---|---|---|
| Compound | $EC_{50}$ | $EC_{90}$ |
| 11 | 0.7 | 2.4 |
| 19 | 0.07 | 0.27 |
| 23 | 0.07 | 0.33 |
| 29 | 0.08 | 0.46 |
| 67 | 4.33 | >20 |
| 83 | 0.33 | 0.91 |
| 84 | >10 | ND |

Example 12

The ability of these compounds to inhibit the NoV, specifically Minerva virus protease catalytic Cys139 covalently ($IC_{50}$ and $K_i$) was determined with an enzyme kinetic assay. NoV strains, specifically GII.4 such as the Minerva virus are responsible for causing the majority (~80%) of infections in humans. The activity of the inhibitors was evaluated by monitoring the cleavage of a FRET substrate every one minute for 20 minutes (excitation/emission: 488/520 nm) using a SpectraMax M5 microplate reader (Molecular Devices, Sunnyvale CA). Serial dilutions of each inhibitor were incubated with enzyme for 90 minutes at 37° C. before addition of the FRET substrate to ensure complete inactivation. Commercially available protease inhibitors chymostatin and rupintrivir were used as controls.

TABLE 4

| Compound | IC$_{50}$ (μM) | K$_i$ (μM) |
|---|---|---|
| 11 | 0.112 ± 0.025 | 0.427 ± 0.109 |
| 19 | 0.150 ± 0.002 | 1.19 ± 0.444 |
| 23 | 0.204 ± 0.009 | 1.59 ± 0.050 |
| 29 | 0.140 ± 0.017 | 0.670 ± 0.019 |
| 35 | 0.167 ± 0.005 | 0.858 ± 0.032 |
| 36 | 1.17 ± 0.333 | 3.60 ± 0.501 |
| 37 | 2.63 ± 1.04 | 14.03 ± 5.55 |
| 38 | >10 | ND |
| 39 | >10 | ND |
| 64 | >100 | ND |
| 67 | 30.0 ± 1.8 | >100 |
| 83 | 0.482 ± 0.07 | 7.095 ± 5.583 |
| 84 | >100 | ND |
| chymostatin | 13.7 | 1.6 ± 1.0 |
| rupintrivir | 23.6 | 8.2 ± 2.3 |

Example 13

Norovirus GI.1 (Norwalk virus) protease were tested for enzymatic activity using a fluorescence resonance energy transfer (FRET) based enzyme assay. Norovirus GI.1 represents 5 to 10% of the clinical isolates. The FRET kinetic enzyme assays were performed as follows. The purified viral protease was diluted in reaction buffer (50 mM HEPES, pH 8.0, 120 mM NaCl, 0.4 mM EDTA, 20% glycerol, and 4 mM DTT) to a final concentration of 128 nM. Each reaction was initiated by addition of FRET substrate [(HiLyte Fluor 488)-DFELQGPK-(QXL520)]. To determine kinetic parameters, the FRET substrate was serially diluted to final concentrations of 100 μM to 49 nM and added to the reaction. The final reaction volume was 100 μL. The fluorescence emitted by substrate cleavage was monitored by a microplate reader (SpectraMax M5, Molecular Devices, Sunnyvale, CA, USA) at a 488 nm excitation wavelength with an emission wavelength of 520 nm. Readings were taken every minute for 20 minutes, and the reactions were performed at 37° C. In order to convert RFU into μM, a standard curve was created by measuring fluorescence of free HiLyte Fluor 488, which was serially diluted from 250 nM to 3.9 nM. All data were plotted and analyzed with GraphPad Prism v. 6.07.

TABLE 5

| Compound | IC$_{50}$ (μM) | K$_i$ (μM) |
|---|---|---|
| 11 | 0.044 ± 0.008 | 0.123 ± 0.006 |
| 19 | 0.080 ± 0.023 | 0.155 ± 0.008 |
| 23 | 0.096 ± 0.017 | 0.528 ± 0.167 |
| 29 | 0.112 ± 0.013 | 0.350 ± 0.140 |
| 35 | 0.096 ± 0.011 | 0.465 ± 0.201 |
| 36 | 0.593 ± 0.124 | 1.697 ± 0.332 |
| 37 | 0.654 ± 0.285 | 2.241 ± 0.438 |
| 38 | >10 | ND |
| 39 | >10 | ND |
| 64 | 10 | ND |
| 67 | >10 | ND |
| 83 | 0.084 ± 0.019 | 0.256 ± 0.057 |
| 84 | >100 | ND |

Various publications are cited herein, the disclosures of which are incorporated by reference in their entireties for all purposes.

The present invention is not to be limited in scope by the specific embodiments described herein. Indeed, various modifications of the invention in addition to those described will become apparent to those skilled in the art from the foregoing description and accompanying FIGURES. Such modifications are intended to fall within the scope of the appended claims.

We claim:

1. A compound of the following formula:

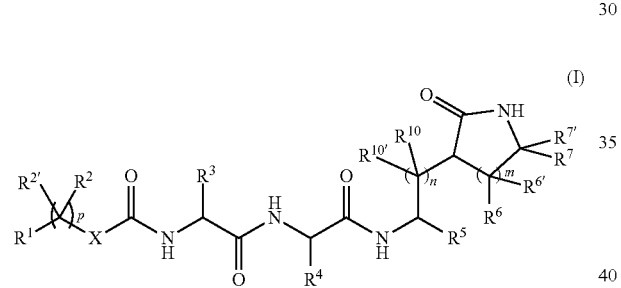

or a pharmaceutically acceptable salt thereof, wherein:

$R^5$ is selected from the group consisting of

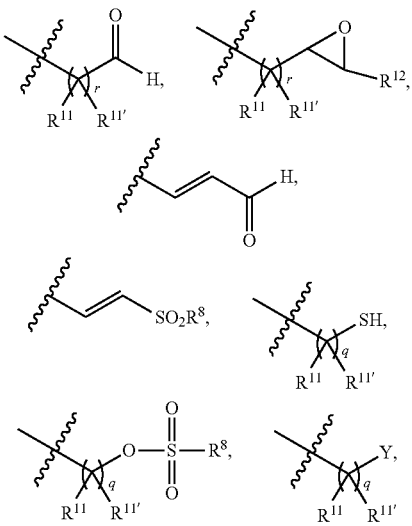

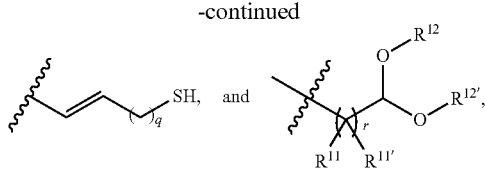

$R^2$, $R^{2'}$, $R^{10}$, $R^{10'}$, $R^{11}$ and $R^{11'}$ are, independently, hydrogen, $CF_3$, $C_{1-6}$ alkyl, $C_{1-6}$ haloalkyl, or $C_{2-6}$ alkenyl, $R^{12}$ and $R^{12'}$ are, independently, $C_{1-6}$ alkyl, $C_{1-6}$ haloalkyl, or $C_{2-6}$ alkenyl, $R^{12}$ and $R^{12'}$ can come together to form an optionally substituted $C_{3-7}$ ring, optionally containing an N, O, or S;

$R^8$ is, independently, optionally substituted $C_{1-6}$ alkyl, $C_{1-6}$ haloalkyl, $C_{2-6}$ alkenyl, aryl, or arylalkyl;

m, n, p and r are independently 0, 1, 2, 3, 4 or 5;

q is 1, 2, 3, 4 or 5;

X is NH,

Y is independently Cl, F, I or Br, $R^{12}$ is hydrogen, $CF_3$, $CO_2R'$, $S(O)_2R'$, $S(O)_2N(R')_2$, $P(O)(OR')_2$, $C_{2-6}$ alkenyl, $C_{2-6}$ alkynyl, $C_{3-6}$ alkoxyalkyl, $C_{1-6}$ alkyl, arylalkoxycarbonyl, $C_{1-6}$ haloalkyl, heterocyclylalkyl, or $C_{1-6}$ hydroxy alkyl;

$R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl, or $R^6$ and $R^{6'}$, together with the carbon to which they are attached, form a carbonyl;

each R' is, independently, H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, the R' groups, and other optionally substituted groups, can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, or phosphonate;

two R' residing on the same carbon or nitrogen atom can come together to form a $C_{3-6}$ ring optionally containing an N, O, or S;

$R^6$ and $R^6$ can come together to form an optionally substituted double bond, a $C_{3-6}$ ring optionally containing an N, O, or S;

$R^7$ and $R^{7'}$ are, independently, hydrogen, $CF_3$, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

$R^7$ and $R^{7'}$ can come together to form an optionally substituted double bond or a $C_{3-6}$ ring optionally containing an N, O, or S;

$R^3$ is arylalkyl or heteroarylalkyl, $R^4$ is optionally substituted $C_{1-6}$ alkyl, $C_{1-6}$ haloalkyl, $C_{2-8}$ alkoxyalkyl, arylalkyl, heteroarylalkyl, or —$CH_2$—$R^{4'}$, $R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring; and $R^1$ is optionally substituted aryl, heteroaryl, aryloxy, heteroaryloxy, arylalkoxy, or heteroarylalkoxy.

2. A pharmaceutical composition comprising a compound of claim 1, and a pharmaceutically-acceptable carrier.

3. The pharmaceutical composition of claim 2, further comprising a second antiviral agent selected from the group consisting of a polymerase inhibitors, protease inhibitors, anti-emetics, anti-diarrheals, cellular deubiquitinase inhibitors, IFN-λ inhibitors, agents of distinct or unknown mechanism, and combinations thereof.

4. A method for treating a host infected with Norovirus, comprising administering an effective amount of a compound of claim 1 to a patient in need of treatment thereof.

5. The method of claim 4, wherein the method further comprising administering another Norovirus virus agent in combination or alternation with the compound of claim 1.

6. A compound of the following formula:

(I)

or a pharmaceutically acceptable salt thereof, wherein:

$R^5$ is

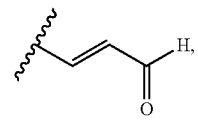

$R^2$, $R^{2'}$, $R^{10}$, $R^{10'}$, $R^{11}$ and $R^{11'}$ are, independently, hydrogen, $CF_3$, $C_{1-6}$ alkyl, $C_{1-6}$ haloalkyl, or $C_{2-6}$ alkenyl, $R^{12}$ and $R^{12'}$ are, independently, $C_{1-6}$ alkyl, $C_{1-6}$ haloalkyl, or $C_{2-6}$ alkenyl, $R^{12}$ and $R^{12'}$ can come together to form an optionally substituted $C_{3-7}$ ring, optionally containing an N, O, or S;

$R^8$ is, independently, optionally substituted $C_{1-6}$ alkyl, $C_{1-6}$ haloalkyl, $C_{2-6}$ alkenyl, aryl, or arylalkyl;

m, n, p and r are independently 0, 1, 2, 3, 4 or 5;

q is 1, 2, 3, 4 or 5,

X is O or NH,

Y is independently Cl, F, I or Br, $R^{12}$ is hydrogen, $CF_3$, $CO_2R'$, $S(O)_2R'$, $S(O)_2N(R')_2$, $P(O)(OR')_2$, $C_{2-6}$ alkenyl, $C_{2-6}$ alkynyl, $C_{3-6}$ alkoxyalkyl, $C_{1-6}$ alkyl, arylalkoxycarbonyl, $C_{1-6}$ haloalkyl, heterocyclylalkyl, or $C_{1-6}$ hydroxy alkyl;

$R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, aryl alkoxycarbonyl, carboxy, $C_{1-6}$ haloalkyl, heterocyclylalkyl, or $C_{1-6}$ hydroxyalkyl, or $R^6$ and $R^{6'}$, together with the carbon to which they are attached, form a carbonyl;

each R' is, independently, H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, the R' groups, and other optionally substituted groups, can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, or phosphonate;

two R' residing on the same carbon or nitrogen atom can come together to form a $C_{3-6}$ ring optionally containing an N, O, or S;

$R^6$ and $R^6$ can come together to form an optionally substituted double bond, a $C_{3-6}$ ring optionally containing an N, O, or S;

$R^7$ and $R^{7'}$ are, independently, hydrogen, $CF_3$, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

$R^7$ and $R^{7'}$ can come together to form an optionally substituted double bond or a $C_{3-6}$ ring optionally containing an N, O, or S;

$R^3$ is arylalkyl or heteroarylalkyl, $R^4$ is optionally substituted $C_{1-6}$ alkyl, $C_{1-6}$ haloalkyl, $C_{2-8}$ alkoxyalkyl, arylalkyl, heteroarylalkyl, or —$CH_2$—$R^{4'}$, $R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring; and $R^1$ is optionally substituted aryl, heteroaryl, aryloxy, heteroaryloxy, arylalkoxy, or heteroarylalkoxy.

7. A compound of the following formula:

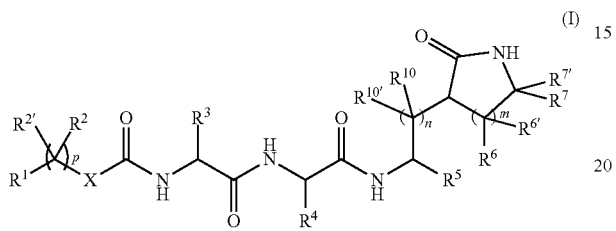

or a pharmaceutically acceptable salt thereof, wherein, $R^5$ is selected from the group consisting of

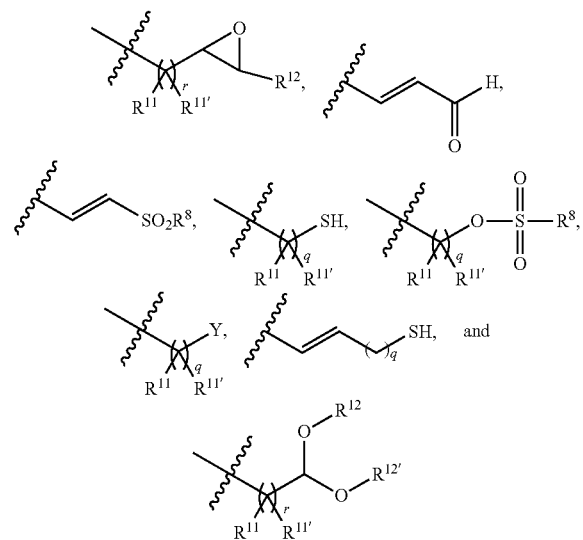

$R^2$, $R^{2'}$, $R^{10}$, $R^{10'}$, $R^{11}$ and $R^{11'}$ are, independently, hydrogen, $CF_3$, $C_{1-6}$ alkyl, $C_{1-6}$ haloalkyl, or $C_{2-6}$ alkenyl, $R^{12}$ and $R^{12'}$ are, independently, $C_{1-6}$ alkyl, $C_{1-6}$ haloalkyl, or $C_{2-6}$ alkenyl, $R^{12}$ and $R^{12'}$ can come together to form an optionally substituted $C_{3-7}$ ring, optionally containing an N, O, or S;

$R^8$ is, independently, optionally substituted $C_{1-6}$ alkyl, $C_{1-6}$ haloalkyl, $C_{2-6}$ alkenyl, aryl, or arylalkyl;

m, n, p and r are independently 0, 1, 2, 3, 4 or 5;

q is 1, 2, 3, 4 or 5,

X is O or NH,

Y is independently Cl, F, I or Br, $R^{12}$ is hydrogen, $CF_3$, $CO_2R'$, $S(O)_2R'$, $S(O)_2N(R')_2$, $P(O)(OR')^2$, $C_{2-6}$ alkenyl, $C_{2-6}$ alkynyl, $C_{3-6}$ alkoxyalkyl, $C_{1-6}$ alkyl, arylalkoxycarbonyl, $C_{1-6}$ haloalkyl, heterocyclylalkyl, or $C_{1-6}$ hydroxy alkyl;

$R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl, or $R^6$ and $R^{6'}$, together with the carbon to which they are attached, form a carbonyl;

each R' is, independently, H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl, the R' groups, and other optionally substituted groups, can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, or phosphonate;

two R' residing on the same carbon or nitrogen atom can come together to form a $C_{3-6}$ ring optionally containing an N, O, or S;

$R^6$ and $R^{6'}$ can come together to form an optionally substituted double bond, a $C_{3-6}$ ring optionally containing an N, O, or S;

$R^7$ and $R^{7'}$ are, independently, hydrogen, $CF_3$, $N(R')S(O)_2R'$, $S(O)_2R'$, $S(O)_2N(R')$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;

$R^7$ and $R^{7'}$ can come together to form an optionally substituted double bond or a $C_{3-6}$ ring optionally containing an N, O, or S;

$R^3$ is arylalkyl or heteroarylalkyl, $R^4$ is optionally substituted $C_{1-6}$ alkyl, $R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring; and $R^1$ is optionally substituted aryl, heteroaryl, aryloxy, heteroaryloxy, arylalkoxy, or heteroarylalkoxy.

8. The compound of claim 1, wherein $R^4$ is alkylaryl or alkylheteroaryl.

9. The compound of claim 1, wherein $R^1$ is optionally substituted aryl or heteroaryl.

10. The compound of claim 1, wherein m is 1.

11. The compound of claim 1, wherein m is 2.

12. The compound of claim 1, wherein $R^2$ and $R^{2'}$ are hydrogen.

13. The compound of claim 1, wherein $R^3$ is alkylaryl.

14. The compound of claim 13, wherein $R^3$ is —$CH_2$-optionally-substituted naphthyl.

15. The compound of claim 13, wherein $R^3$ is —$CH_2$-optionally-substituted phenyl.

16. A compound of the following formula:

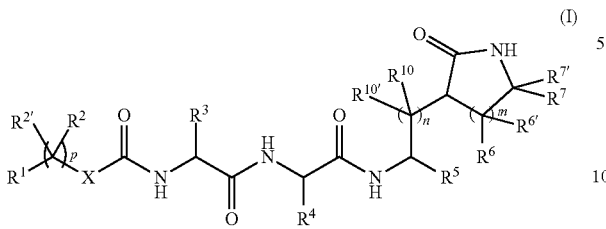
(I)

or a pharmaceutically acceptable salt thereof, wherein:
$R^5$ is selected from the group consisting of

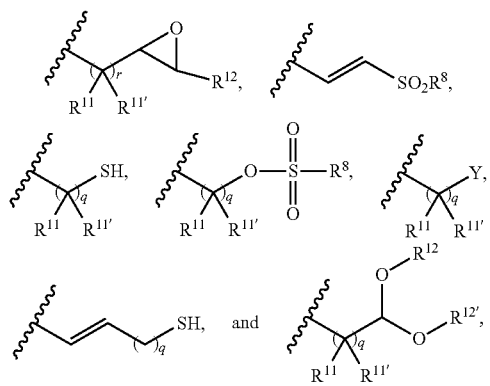

$R^2$, $R^{2'}$, $R^{10}$, $R^{10'}$, $R^{11}$ and $R^{11'}$ are, independently, hydrogen, $CF_3$, $C_{1-6}$ alkyl, $C_{1-6}$ haloalkyl, or $C_{2-6}$ alkenyl,
$R^{12}$ and $R^{12'}$ are, independently, $C_{1-6}$ alkyl, $C_{1-6}$ haloalkyl, or $C_{2-6}$ alkenyl,
$R^{12}$ and $R^{12'}$ can come together to form an optionally substituted $C_{3-7}$ ring, optionally containing an N, O, or S;
$R^8$ is, independently, optionally substituted $C_{1-6}$ alkyl, $C_{1-6}$ haloalkyl, $C_{2-6}$ alkenyl, aryl, or arylalkyl;
m, n, p and r are independently 0, 1, 2, 3, 4 or 5;
q is 1, 2, 3, 4 or 5,
X is O or NH,
Y is independently Cl, F, I or Br,
$R^{12}$ is hydrogen, $CF_3$, $CO_2R'$, $S(O)_2R'$, $S(O)_2N(R')_2$, $P(O)(OR')_2$, $C_{2-6}$ alkenyl, $C_{2-6}$ alkynyl, $C_{3-6}$ alkoxyalkyl, $C_{1-6}$ alkyl, arylalkoxycarbonyl, $C_{1-6}$ haloalkyl, heterocyclylalkyl, or $C_{1-6}$ hydroxy alkyl;
$R^6$ and $R^{6'}$ are, independently, hydrogen, halogen, $CF_3$, hydroxy, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl,
or $R^6$ and $R^{6'}$, together with the carbon to which they are attached, form a carbonyl;
each R' is, independently, H, $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, alkylaryl, or arylalkyl,
the R' groups, and other optionally substituted groups, can optionally be substituted with one or more substituents, which substituents are, independently, halo, $C_{1-6}$ haloalkyl, $C_{1-6}$ hydroxyalkyl, hydroxyl, carboxyl, acyl, aryl, acyloxy, amino, amido, carboxyl derivatives, alkylamino, dialkylamino, arylamino, alkoxy, alkoxyalkyl, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrazine, carbamate, phosphonic acid, or phosphonate;
two R' residing on the same carbon or nitrogen atom can come together to form a $C_{3-6}$ ring optionally containing an N, O, or S;
$R^6$ and $R^{6'}$ can come together to form an optionally substituted double bond, a $C_{3-6}$ ring optionally containing an N, O, or S;
$R^7$ and $R^{7'}$ are, independently, hydrogen, $CF_3$, $N(R')S(O)_2R'$, $S(O)_2R'$, $S(O)_2N(R')_2$, $C_{1-6}$ alkoxy, $C_{2-6}$ alkenyl, cyano, $C_{2-6}$ alkynyl, $C_{3-6}$ alkoxyalkyl, alkoxycarbonyl, alkoxycarbonylalkyl, $C_{1-6}$ alkyl, arylalkoxycarbonyl, carboxy, $C_{1-6}$ haloalkyl, heterocyclylalkyl, or $C_{1-6}$ hydroxyalkyl;
$R^7$ and $R^{7'}$ can come together to form an optionally substituted double bond or a $C_{3-6}$ ring optionally containing an N, O, or S;
$R^3$ is arylalkyl or heteroarylalkyl,
$R^4$ is optionally substituted $C_{1-6}$ alkyl, $C_{1-6}$ haloalkyl, $C_{2-8}$ alkoxyalkyl, arylalkyl, heteroarylalkyl, or —$CH_2$—$R^{4'}$,
$R^{4'}$ is a six-membered ring or a six-membered bridged or spiro-fused ring containing zero, one, or two heteroatoms, which are independently N, O, or S, a seven-membered bridged or spiro-fused ring containing zero, one, or two heteroatoms, which are, independently, N, O, or S, a five-membered ring containing zero, one, or two heteroatoms, which are, independently, N, O, or S; a four-membered ring containing zero, one, or two heteroatoms, which are, independently, N, O, or S, or a three membered ring; and
$R^1$ is optionally substituted aryl, heteroaryl, aryloxy, heteroaryloxy, arylalkoxy, or heteroarylalkoxy.

* * * * *

SEQUENCE LISTING

```
<160> NUMBER OF SEQ ID NOS: 6

<210> SEQ ID NO 1
<211> LENGTH: 17
<212> TYPE: DNA
<213> ORGANISM: Homo sapiens

<400> SEQUENCE: 1
tgcccgccat catccta                                                        17

<210> SEQ ID NO 2
<211> LENGTH: 21
<212> TYPE: DNA
<213> ORGANISM: Homo sapiens

<400> SEQUENCE: 2
tcctcatcgc cctcccatcc c                                                   21

<210> SEQ ID NO 3
<211> LENGTH: 23
<212> TYPE: DNA
<213> ORGANISM: Homo sapiens

<400> SEQUENCE: 3
cgtctgttat gtaaaggatg cgt                                                 23
```

```
<210> SEQ ID NO 4
<211> LENGTH: 17
<212> TYPE: DNA
<213> ORGANISM: Homo sapiens

<400> SEQUENCE: 4
gcgcggctac agcttca                                                17

<210> SEQ ID NO 5
<211> LENGTH: 19
<212> TYPE: DNA
<213> ORGANISM: Homo sapiens

<400> SEQUENCE: 5
caccacggcc gagccggga                                              19

<210> SEQ ID NO 6
<211> LENGTH: 22
<212> TYPE: DNA
<213> ORGANISM: Homo sapiens

<400> SEQUENCE: 6
tctccttaat gtcacgcacg at                                          22
```